US010658083B2

(12) United States Patent
Jordan et al.

(10) Patent No.: US 10,658,083 B2
(45) Date of Patent: *May 19, 2020

(54) GRAPHICAL USER INTERFACES INCLUDING TOUCHPAD DRIVING INTERFACES FOR TELEMEDICINE DEVICES

(71) Applicants: InTouch Technologies, Inc., Goleta, CA (US); iRobot Corporation, Bedford, MA (US)

(72) Inventors: Charles S. Jordan, Santa Barbara, CA (US); Andy Young, Santa Barbara, CA (US); Mei Sheng Ng, Santa Barbara, CA (US); Yair Lurie, Santa Barbara, CA (US); Fuji Lai, Goleta, CA (US); Timothy C. Wright, Santa Barbara, CA (US); Cody Herzog, Santa Barbara, CA (US); Blair Whitney, Santa Barbara, CA (US); Bill Rizzi, Santa Barbara, CA (US); James Ballantyne, Santa Barbara, CA (US); Yulun Wang, Goleta, CA (US); Cheuk Wah Wong, Bedford, MA (US); Justin Kearns, Somerville, MA (US); Orjeta Taka, Bedford, MA (US); Ramchandra Karandikar, Goleta, CA (US)

(73) Assignee: INTOUCH TECHNOLOGIES, INC., Santa Barbara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/045,608

(22) Filed: Jul. 25, 2018

(65) Prior Publication Data

US 2019/0066839 A1 Feb. 28, 2019

Related U.S. Application Data

(63) Continuation of application No. 15/154,518, filed on May 13, 2016, now Pat. No. 10,061,896, which is a
(Continued)

(51) Int. Cl.
*H04N 7/14* (2006.01)
*G16H 40/63* (2018.01)
(Continued)

(52) U.S. Cl.
CPC ......... *G16H 40/63* (2018.01); *G06F 3/04847* (2013.01); *G06F 3/04883* (2013.01);
(Continued)

(58) Field of Classification Search
CPC combination set(s) only.
See application file for complete search history.

(56) References Cited

U.S. PATENT DOCUMENTS

| 3,821,995 A | 7/1974 | Aghnides |
| 4,107,689 A | 8/1978 | Jellinek |

(Continued)

FOREIGN PATENT DOCUMENTS

| AU | 1216200 | 5/2000 |
| CA | 2289697 | 11/1998 |

(Continued)

OTHER PUBLICATIONS

"Google Translation of Innovations Report," From research project to television star: Care-O-bot in ZDF series, available online at http://www.innovations-report.de/specials/printa.php?id=5157, Sep. 28, 2001, 2 pages.
(Continued)

*Primary Examiner* — Duc Nguyen
*Assistant Examiner* — Assad Mohammed
(74) *Attorney, Agent, or Firm* — Kory D. Christensen

(57) ABSTRACT

The present disclosure describes various aspects of remote presence interfaces (RPIs) for use on portable electronic devices (PEDs) to interface with remote telepresence devices. An RPI may allow a user to interact with a telepresence device, view a live video feed, provide navi-
(Continued)

gational instructions, and/or otherwise interact with the telepresence device. The RPI may allow a user to manually, semi-autonomously, or autonomously control the movement of the telepresence device. One or more panels associated with a video feed, patient data, calendars, date, time, telemetry data, PED data, telepresence device data, healthcare facility information, healthcare practitioner information, menu tabs, settings controls, and/or other features may be utilized via the RPI.

13 Claims, 58 Drawing Sheets

Related U.S. Application Data continuation of application No. 14/550,750, filed on Nov. 21, 2014, now Pat. No. 9,361,021, which is a continuation of application No. PCT/US2013/031743, filed on Mar. 14, 2013.

(60) Provisional application No. 61/650,205, filed on May 22, 2012, provisional application No. 61/674,794, filed on Jul. 23, 2012, provisional application No. 61/674,796, filed on Jul. 23, 2012, provisional application No. 61/674,782, filed on Jul. 23, 2012, provisional application No. 61/766,623, filed on Feb. 19, 2013.

(51) Int. Cl.
*G06Q 10/10* (2012.01)
*G06F 3/0484* (2013.01)
*G16Z 99/00* (2019.01)
*G06F 19/00* (2018.01)
*G06F 3/0488* (2013.01)
*G16H 40/67* (2018.01)
*G06Q 50/22* (2018.01)

(52) U.S. Cl.
CPC .......... *G06F 19/00* (2013.01); *G06F 19/3418* (2013.01); *G06Q 10/10* (2013.01); *G16H 40/67* (2018.01); *G16Z 99/00* (2019.02); *H04N 7/142* (2013.01); *H04N 7/147* (2013.01); *G06Q 50/22* (2013.01)

(56) References Cited

U.S. PATENT DOCUMENTS

| | | |
|---|---|---|
| 4,213,182 A | 7/1980 | Eichelberger et al. |
| 4,413,693 A | 11/1983 | Derby |
| 4,471,354 A | 9/1984 | Smith |
| 4,519,466 A | 5/1985 | Shiraishi |
| 4,553,309 A | 11/1985 | Hess et al. |
| 4,572,594 A | 2/1986 | Schwartz |
| 4,625,274 A | 11/1986 | Schroeder |
| 4,638,445 A | 1/1987 | Mattaboni |
| 4,652,204 A | 3/1987 | Arnett |
| 4,669,168 A | 6/1987 | Tamura et al. |
| 4,679,152 A | 7/1987 | Perdue |
| 4,697,278 A | 9/1987 | Fleischer |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,953,159 A | 8/1990 | Hayden et al. |
| 4,974,607 A | 12/1990 | Miwa |
| 4,977,971 A | 12/1990 | Crane et al. |
| 5,006,988 A | 4/1991 | Borenstein et al. |
| 5,040,116 A | 8/1991 | Evans et al. |
| 5,051,906 A | 9/1991 | Evans et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,220,263 A | 6/1993 | Onishi et al. |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen et al. |
| 5,262,944 A | 11/1993 | Weisner et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnson |
| 5,400,068 A | 3/1995 | Ishida et al. |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fischer |
| 5,572,999 A | 11/1996 | Funda et al. |
| 5,594,859 A | 1/1997 | Palmer et al. |
| 5,600,573 A | 2/1997 | Hendricks et al. |
| 5,617,539 A | 4/1997 | Ludwig et al. |
| 5,619,341 A | 4/1997 | Auyeung et al. |
| 5,623,679 A | 4/1997 | Rivette et al. |
| 5,630,566 A | 5/1997 | Case |
| 5,636,218 A | 6/1997 | Ishikawa et al. |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,734,804 A | 3/1998 | Bergner |
| 5,734,805 A | 3/1998 | Isensee et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |

(56) References Cited

U.S. PATENT DOCUMENTS

| | | |
|---|---|---|
| 5,764,731 A | 6/1998 | Yablon |
| 5,767,897 A | 6/1998 | Howell |
| 5,786,846 A | 7/1998 | Hiroaki |
| 5,787,745 A | 8/1998 | Colens |
| 5,793,365 A | 8/1998 | Tang et al. |
| 5,801,755 A | 9/1998 | Echerer |
| 5,802,494 A | 9/1998 | Kuno |
| 5,836,872 A | 11/1998 | Kenet et al. |
| 5,838,575 A | 11/1998 | Lion |
| 5,844,599 A | 12/1998 | Hildin |
| 5,857,534 A | 1/1999 | Devault et al. |
| 5,867,494 A | 2/1999 | Krishnaswamy et al. |
| 5,867,653 A | 2/1999 | Aras et al. |
| 5,871,451 A | 2/1999 | Unger et al. |
| 5,872,922 A | 2/1999 | Hogan et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,140 A | 12/1999 | Carter |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,091,219 A | 7/2000 | Maruo et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,189,034 B1 | 2/2001 | Riddle |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,342,915 B1 | 1/2002 | Ozaki et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto et al. |
| 6,438,457 B1 | 8/2002 | Kokoo et al. |
| 6,445,964 B1 | 9/2002 | White et al. |
| 6,449,762 B1 | 9/2002 | Mcelvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury et al. |
| 6,691,000 B2 | 2/2004 | Nagai et al. |
| 6,693,585 B1 | 2/2004 | Macleod |
| 6,710,797 B1 | 3/2004 | Mcnelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |

(56) References Cited

U.S. PATENT DOCUMENTS

| | | |
|---|---|---|
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,856,662 B2 | 2/2005 | Glass et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling |
| 7,007,235 B1 | 2/2006 | Hussein et al. |
| 7,011,538 B2 | 3/2006 | Chang |
| 7,015,934 B2 | 3/2006 | Toyama et al. |
| 7,030,757 B2 | 4/2006 | Matsuhira et al. |
| RE39,080 E | 5/2006 | Johnston |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | Mclurkin et al. |
| 7,123,285 B2 | 10/2006 | Smith et al. |
| 7,123,292 B1 | 10/2006 | Seeger et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld et al. |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'Rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | Dirienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Goncalves et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,210 B2 | 2/2011 | Choi |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Wang et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |

(56) References Cited

U.S. PATENT DOCUMENTS

| | | |
|---|---|---|
| 8,400,491 B1 | 3/2013 | Panpaliya et al. |
| 8,401,229 B2 | 3/2013 | Hassan-Shafique et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,503,340 B1 | 8/2013 | Xu |
| 8,515,577 B2 | 8/2013 | Wang et al. |
| 8,527,094 B2 | 9/2013 | Kumar et al. |
| 8,531,502 B2 | 9/2013 | Cheng et al. |
| 8,532,860 B2 | 9/2013 | Daly |
| 8,610,786 B2 | 12/2013 | Ortiz |
| 8,612,051 B2 | 12/2013 | Normal et al. |
| 8,620,077 B1 | 12/2013 | Grundmann et al. |
| 8,639,797 B1 | 1/2014 | Pan et al. |
| 8,670,017 B2 | 3/2014 | Stuart et al. |
| 8,712,162 B2 | 4/2014 | Kirsch |
| 8,718,837 B2 | 5/2014 | Wang et al. |
| 8,726,454 B2 | 5/2014 | Gilbert et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 8,965,579 B2 | 2/2015 | Wang et al. |
| 8,983,772 B2 | 3/2015 | Lee |
| 9,098,611 B2 | 8/2015 | Pinter et al. |
| 9,147,284 B2 | 9/2015 | Keene et al. |
| 9,219,857 B2 | 12/2015 | Eldon |
| 9,224,181 B2 | 12/2015 | Pinter et al. |
| 9,323,250 B2 | 4/2016 | Wang et al. |
| 9,361,021 B2 | 6/2016 | Jordan et al. |
| 2001/0002448 A1 | 5/2001 | Wilson et al. |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0030397 A1 | 3/2002 | Tamura et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2002/0186243 A1 | 12/2002 | Ellis et al. |
| 2003/0016726 A1 | 1/2003 | Pavlidis |
| 2003/0021107 A1 | 1/2003 | Howell et al. |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0179223 A1* | 9/2003 | Ying .................. G06F 3/0482 715/702 |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | Kneifel et al. |
| 2003/0231244 A1 | 12/2003 | Bonilla et al. |
| 2003/0232649 A1 | 12/2003 | Gizis et al. |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0009138 A1 | 1/2004 | Hockley, Jr. et al. |
| 2004/0010344 A1 | 1/2004 | Hiratsuka et al. |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0140404 A1 | 7/2004 | Ohta et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |

(56) References Cited

U.S. PATENT DOCUMENTS

| | | |
|---|---|---|
| 2004/0175684 A1 | 9/2004 | Kaasa et al. |
| 2004/0176118 A1* | 9/2004 | Strittmatter ............ H04L 67/16 455/500 |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1 | 10/2004 | Prendergast |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0236830 A1 | 11/2004 | Nelson |
| 2004/0240981 A1 | 12/2004 | Dothan et al. |
| 2004/0241981 A1 | 12/2004 | Doris et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang et al. |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka et al. |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovynin |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1* | 9/2005 | Wang ....................... B25J 5/00 455/67.7 |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |
| 2005/0267826 A1 | 12/2005 | Levy et al. |
| 2005/0278446 A1 | 12/2005 | Bryant |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson |
| 2006/0161303 A1 | 7/2006 | Wang et al. |
| 2006/0164546 A1 | 7/2006 | Adachi |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0184274 A1 | 8/2006 | Sakai et al. |
| 2006/0189393 A1 | 8/2006 | Edery |
| 2006/0195569 A1 | 8/2006 | Barker |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0016328 A1 | 1/2007 | Ziegler et al. |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0061041 A1 | 3/2007 | Zweig |
| 2007/0064092 A1 | 3/2007 | Sandberg et al. |
| 2007/0070069 A1 | 3/2007 | Samarasekera |
| 2007/0078566 A1 | 4/2007 | Wang et al. |
| 2007/0093279 A1 | 4/2007 | Janik |
| 2007/0109324 A1 | 5/2007 | Lin |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0182811 A1 | 8/2007 | Rockefeller et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255115 A1 | 11/2007 | Anglin et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |

(56) References Cited

U.S. PATENT DOCUMENTS

| | | |
|---|---|---|
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0056933 A1 | 3/2008 | Moore et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1 | 5/2008 | Warner et al. |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0242220 A1 | 10/2008 | Wilson |
| 2008/0255703 A1 | 10/2008 | Wang et al. |
| 2008/0263451 A1 | 10/2008 | Portele et al. |
| 2008/0263628 A1 | 10/2008 | Normal et al. |
| 2008/0267069 A1 | 10/2008 | Thielman et al. |
| 2008/0269949 A1 | 10/2008 | Normal et al. |
| 2008/0281467 A1 | 11/2008 | Pinter |
| 2008/0285886 A1 | 11/2008 | Allen |
| 2008/0306375 A1 | 12/2008 | Sayler et al. |
| 2009/0021572 A1 | 1/2009 | Garudadri et al. |
| 2009/0022131 A1* | 1/2009 | Rusanen ............... B66B 1/468 370/338 |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1 | 3/2009 | Panda et al. |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0146882 A1 | 6/2009 | Halivaara et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177641 A1 | 7/2009 | Raghavan |
| 2009/0201372 A1 | 8/2009 | O'Doherty et al. |
| 2009/0237317 A1 | 8/2009 | Rofougaran |
| 2009/0234499 A1 | 9/2009 | Nielsen et al. |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063636 A1 | 3/2010 | Matsumoto et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1 | 4/2010 | Gale |
| 2010/0115418 A1 | 5/2010 | Wang et al. |
| 2010/0116566 A1 | 5/2010 | Ohm et al. |
| 2010/0128104 A1 | 5/2010 | Fabregat et al. |
| 2010/0131103 A1 | 5/2010 | Herzog et al. |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0217438 A1* | 8/2010 | Kawaguchi ............ B25J 9/1661 700/248 |
| 2010/0228249 A1 | 9/2010 | Mohr et al. |
| 2010/0145479 A1 | 10/2010 | Griffiths |
| 2010/0253775 A1 | 10/2010 | Yamaguchi |
| 2010/0268383 A1* | 10/2010 | Wang ..................... B25J 5/00 700/248 |
| 2010/0278086 A1 | 11/2010 | Pochiraju et al. |
| 2010/0286905 A1 | 11/2010 | Goncalves et al. |
| 2010/0287006 A1* | 11/2010 | Cannon ................ G06Q 10/06 705/3 |
| 2010/0301679 A1 | 12/2010 | Murray et al. |
| 2010/0315352 A1 | 12/2010 | Hamamura |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0107374 A1* | 5/2011 | Roberts ............... H04N 5/44543 725/46 |
| 2011/0153198 A1 | 6/2011 | Kokkas et al. |
| 2011/0167151 A1* | 7/2011 | Nishiyama ............. G06F 9/542 709/224 |
| 2011/0169832 A1 | 7/2011 | Brown et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Temby et al. |
| 2011/0218674 A1 | 9/2011 | Stuart et al. |
| 2011/0231796 A1 | 9/2011 | Vigil |
| 2011/0245973 A1 | 10/2011 | Wang et al. |
| 2011/0246015 A1 | 10/2011 | Cummings |
| 2011/0249079 A1 | 10/2011 | Santamaria et al. |
| 2011/0280551 A1 | 11/2011 | Sammon |
| 2011/0288417 A1 | 11/2011 | Pinter et al. |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0143906 A1* | 6/2012 | Sibbold ............... G06F 17/30038 707/769 |
| 2012/0176525 A1 | 7/2012 | Garin |
| 2012/0182392 A1 | 7/2012 | Kearns et al. |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0215380 A1* | 8/2012 | Fouillade ............. G05D 1/0038 701/2 |
| 2012/0215830 A1 | 8/2012 | Anguiano |
| 2012/0218374 A1 | 8/2012 | Matula et al. |
| 2012/0220372 A1 | 8/2012 | Cheung et al. |
| 2012/0291809 A1 | 11/2012 | Kuhe et al. |
| 2012/0316676 A1 | 12/2012 | Fouillade et al. |
| 2013/0097264 A1 | 4/2013 | Bangalore et al. |
| 2013/0158720 A1 | 6/2013 | Zywicki et al. |
| 2013/0179067 A1* | 7/2013 | Trowbridge ......... G01C 21/3484 701/410 |
| 2013/0198321 A1* | 8/2013 | Martin ................. G06F 16/48 709/217 |
| 2013/0250938 A1 | 9/2013 | Anandakumar et al. |
| 2013/0275922 A1 | 10/2013 | Pinter et al. |
| 2013/0304301 A1* | 11/2013 | Rakshit .............. G05D 1/0276 701/25 |
| 2013/0325244 A1 | 12/2013 | Wang et al. |
| 2014/0047022 A1 | 2/2014 | Chan et al. |
| 2014/0085543 A1 | 3/2014 | Hartley et al. |

(56) References Cited

U.S. PATENT DOCUMENTS

| | | | |
|---|---|---|---|
| 2014/0135990 A1 | 5/2014 | Stuart et al. |
| 2014/0139616 A1 | 5/2014 | Pinter et al. |
| 2014/0155755 A1 | 6/2014 | Pinter et al. |
| 2014/0207286 A1 | 7/2014 | Wang et al. |
| 2014/0267549 A1 | 9/2014 | Pinter et al. |
| 2015/0077502 A1 | 3/2015 | Jordan et al. |
| 2015/0081338 A1 | 3/2015 | Lai et al. |
| 2015/0088310 A1 | 3/2015 | Pinter et al. |
| 2015/0296177 A1 | 10/2015 | Pinter et al. |
| 2015/0314449 A1 | 11/2015 | Wang et al. |

FOREIGN PATENT DOCUMENTS

| | | | |
|---|---|---|---|
| CA | WO-2012061932 A1 * | 5/2012 | ........... B25J 19/023 |
| CN | 1404695 | 3/2003 | |
| CN | 1554193 | 12/2004 | |
| CN | 1554985 | 12/2004 | |
| CN | 1561923 | 1/2005 | |
| CN | 1743144 | 3/2006 | |
| CN | 101049017 | 10/2007 | |
| CN | 101106939 | 1/2008 | |
| CN | 101151614 | 3/2008 | |
| CN | 100407729 | 7/2008 | |
| CN | 101390098 | 3/2009 | |
| CN | 101507260 | 8/2009 | |
| CN | 101730894 | 6/2010 | |
| CN | 101866396 | 10/2010 | |
| CN | 101978365 | 2/2011 | |
| CN | 102203759 | 9/2011 | |
| EP | 466492 | 1/1992 | |
| EP | 488673 | 6/1992 | |
| EP | 981905 | 1/2002 | |
| EP | 1262142 | 12/2002 | |
| EP | 1304872 | 4/2003 | |
| EP | 1536660 | 6/2005 | |
| EP | 1573406 | 9/2005 | |
| EP | 1594660 | 11/2005 | |
| EP | 1763243 | 3/2007 | |
| EP | 1791464 | 6/2007 | |
| EP | 1800476 | 6/2007 | |
| EP | 1819108 | 8/2007 | |
| EP | 1856644 | 11/2007 | |
| EP | 1928310 | 6/2008 | |
| EP | 1232610 | 1/2009 | |
| EP | 2027716 | 2/2009 | |
| EP | 2145274 | 1/2010 | |
| EP | 2214111 | 8/2010 | |
| EP | 2263158 | 12/2010 | |
| EP | 2300930 | 3/2011 | |
| EP | 2342651 | 7/2011 | |
| GB | 2431261 | 4/2007 | |
| JP | 7-194609 | 8/1995 | |
| JP | 7-213753 | 8/1995 | |
| JP | 7-248823 | 9/1995 | |
| JP | 7-257422 | 10/1995 | |
| JP | 8-084328 | 3/1996 | |
| JP | 8-166822 | 6/1996 | |
| JP | 8-320727 | 12/1996 | |
| JP | 9-267276 | 10/1997 | |
| JP | 10-79097 | 3/1998 | |
| JP | 10-288689 | 10/1998 | |
| JP | 11-220706 | 8/1999 | |
| JP | 2000-032319 | 1/2000 | |
| JP | 2000-049800 | 2/2000 | |
| JP | 2000-079587 | 3/2000 | |
| JP | 2000-196876 | 7/2000 | |
| JP | 2001-125641 | 5/2001 | |
| JP | 2001-147718 | 5/2001 | |
| JP | 2001-179663 | 7/2001 | |
| JP | 2001-188124 | 7/2001 | |
| JP | 2001-198865 | 7/2001 | |
| JP | 2001-198868 | 7/2001 | |
| JP | 2001-199356 | 7/2001 | |
| JP | 2002-000574 | 1/2002 | |
| JP | 2002-046088 | 2/2002 | |
| JP | 2002-101333 | 4/2002 | |
| JP | 2002-112970 | 4/2002 | |
| JP | 2002-235423 | 8/2002 | |
| JP | 2002-305743 | 10/2002 | |
| JP | 2002-321180 | 11/2002 | |
| JP | 2002-355779 | 12/2002 | |
| JP | 2004-181229 | 7/2004 | |
| JP | 2004-424824 | 8/2004 | |
| JP | 2004-261941 | 9/2004 | |
| JP | 2004-289379 | 10/2004 | |
| JP | 2005-028066 | 2/2005 | |
| JP | 2005-059170 | 3/2005 | |
| JP | 2005-111083 | 4/2005 | |
| JP | 2006-35381 | 2/2006 | |
| JP | 2006-508806 | 3/2006 | |
| JP | 2006-109094 | 4/2006 | |
| JP | 2006-224294 | 8/2006 | |
| JP | 2006-246438 | 9/2006 | |
| JP | 2007-007040 | 1/2007 | |
| JP | 2007-081646 | 3/2007 | |
| JP | 2007-232208 | 9/2007 | |
| JP | 2007-316966 | 12/2007 | |
| JP | 2009-125133 | 9/2009 | |
| JP | 2010-064154 | 3/2010 | |
| JP | 2010-532109 | 9/2010 | |
| JP | 2010-246954 | 11/2010 | |
| KR | 2006-0037979 | 5/2006 | |
| KR | 2009-0012542 | 2/2009 | |
| KR | 2010-0019479 | 2/2010 | |
| KR | 2010-0139037 | 12/2010 | |
| WO | 93/06690 | 4/1993 | |
| WO | 97/42761 | 11/1997 | |
| WO | 1998/51078 | 11/1998 | |
| WO | 99/67067 | 12/1999 | |
| WO | 2000/025516 | 5/2000 | |
| WO | 2000/033726 | 6/2000 | |
| WO | 2001/31861 | 5/2001 | |
| WO | 2003/077745 | 9/2003 | |
| WO | 2004/008738 | 1/2004 | |
| WO | 2004/012018 | 2/2004 | |
| WO | 2004/075456 | 9/2004 | |
| WO | 2006/012797 | 2/2006 | |
| WO | 2006/044847 | 4/2006 | |
| WO | 2006/078611 | 7/2006 | |
| WO | 2007041295 | 4/2007 | |
| WO | 2007/041038 | 6/2007 | |
| WO | 2008/100272 | 10/2008 | |
| WO | 2009/117274 | 9/2009 | |
| WO | 2009/128997 | 10/2009 | |
| WO | 2009/145958 | 12/2009 | |
| WO | 2010/006205 | 1/2010 | |
| WO | 2010/006211 | 1/2010 | |
| WO | 2010/033666 | 3/2010 | |
| WO | 2010/047881 | 4/2010 | |
| WO | 2010/062798 | 6/2010 | |
| WO | 2010/065257 | 6/2010 | |
| WO | 2010/120407 | 10/2010 | |
| WO | 2011/028589 | 3/2011 | |
| WO | 2011/097130 | 8/2011 | |
| WO | 2011/097132 | 8/2011 | |
| WO | 2011/109336 | 9/2011 | |
| WO | 2011/149902 | 12/2011 | |
| WO | 2013/097264 | 7/2013 | |

OTHER PUBLICATIONS

"Magne Charge," Smart Power of Electric Vehicles, Aug. 26, 1997, 2 pages.
"More Online Robots: Robots that Manipulate," available on-line at http://ford.ieor.berkeley.edu/lr/robots_a2.html, Retrieived on Nov. 23, 2010, Aug. 2001, 2 pages.
"MPEG File Format Summary," available online at http://www.fileformat.info/format/mpeg/egff.htm, Feb. 1, 2001, 8 pages.
"Nomad Scout Language Reference Manual," Nomadic Technologies, Software Version 2.7, Part No. DOC00002, Jul. 12, 1999, 47 pages.
"Robart I, II, III," Spawar, Systems Center Pacific, 1998,8 pages.

(56) References Cited

OTHER PUBLICATIONS

ACM Digital Library Record, Autonomous Robots vol. II Issue 1, available online at http://dl.acm.org/citation.cfm?id=591550&picked=prox&cfid=360891374&cftoken=35225929, Jul. 2001, 2 pages.
Active Media, Inc., "Saphira Software Manual," Saphira Version 5.3, 1997, 105 pages.
Activmedia Robotics, "Pioneer 2/PeopleBot TM," Operations Manual, Version 9, Oct. 2001, 78 pages.
Adams, Chris, "Simulation of Adaptive Behavior (SAB'02)," Mobile Robotics Research Group, The Seventh International Conference, retrieved on Jan. 22, 2014, available online at http://www.dai.ed.ac.uk/groups/mrg/MG.html, Aug. 4-11, 2002, 1 page.
Al-Kassab et al., "A Review of Telemedicine," Journal of Telemedicine and Telecare, vol. 5, Supplement 1, 1999, pp. 103-106.
Ando et al., "A Multimedia Self-service Terminal with Conferencing Functions," Robot and Human Communication, Tokyo, Proceedings of $4^{th}$ IEEE International Workshop, Jul. 5-7, 1995, pp. 357-362.
Android Amusement Corp., "What Marketing Secret Renting Robots from Android Amusement Corp!", (Advertisement), 1982, 1 page.
Appeal from the U.S. District Court for the Central District of California in case No. 11-cv-9185, Judge Percy Anderson, Joint Appendix, vol. 1 of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.
Appeal from the U.S. District Court for the Central District of California in case No. 11-cv-9185, Judge Percy Anderson, Joint Appendix, vol. IV of IV, Jun. 24, 2013, pp. A15677-A18127.
Appeal from the U.S. District Court for the Central District of California in case No. 11-cv-9185, Judge Percy Anderson, May 9, 2014, pp. 1-48.
Apple Inc., "I Phone," iPhone Series, XP002696350, Sep. 21, 2012, pp. 1-29.
Applebome, Peter, "Planning Domesticated Robots for Tomorrow's Household," New York Times, available on-line at http://www.theoldrobots.com/images17/dc17.jpg, Mar. 4, 1982, pp. 21 and 23.
Bar-Cohen et al., "Virtual Reality Robotic Telesurgery Simulations Using MEMICA Haptic System," Proceedings of SPIE's $8^{th}$ Annual International Symposium on Smart Structures and Materials, Mar. 5-8, 2001, pp. 1-7.
Barrett, Rick, "Video Conferencing Business Soars as Companies Cut Travel; Some Travel Cuts are Permanent," available online at http://www.ivcl.com/international_videoconferencing_news_videoconferencing_news_19.html, May 13, 2002, 2 pages.
Bartholomew, "Pharmacy Apothecary," available at http://classes.bnf.fr/ema/grands/034.htm, retrieved on Jul. 26, 2012, 2 pages.
Bauer et al., "Remote Telesurgical Mentoring: Feasibility and Efficacy," IEEE, Proceedings of the $33^{rd}$ Hawaii International Conference on System Sciences, 2000, pp. 1-9.
Bauer, Jeffrey C., "Service Robots in Health Care: The Evolution of Mechanical Solutions to Human Resource Problems," Bon Secours Health System Inc., Technology Early Warning System (TEWS), Future of Service Robots in Health Care, Jun. 2003, pp. 1-10.
Bischoff, Rainer, "Design Concept and Realization of the Humanoid Service Robot HERMES," Field and Service Robotics, Springer, 1998, pp. 485-492.
Blackwell, Gerry, "Video: A Wireless LAN Killer App?" available online at http://www.wi-fiplanet.com/columns/article.php/1010261/Video-A-Wireless-LAN-Killer, Apr. 16, 2002 4 pages.
Blaer et al., "TopBot: Automated Network Topology Detection with a Mobile Robot", IEEE, Proceedings of the 2003 International Conference on Robotics 7 Automation, Taipei, Taiwan, Sep. 14-19, 2003, pp. 1582-1587.
Bradner, S., "The Internet Standards Process—Revision 3", Network Working Group, Request for Comments: 2026, BCP 9, Obsoletes: 1602, Category: Best Current Practice, Oct. 1996, pp. 1-36.

Brenner, Pablo, "A Technical Tutorial on the IEEE 802.11 Protocol," Breezecom Wireless Communications, 1997, pp. 1-24.
Breslow et al., "Effect of a Multiple-Site Intensive Care Unit Telemedicine Program on Clinical and Economic Outcome an Alternative Paradigm for Intensivist Staffing," Critical Care Med, vol. 32, No. 1, Jan. 2004, pp. 31-38.
Brooks, Rodney Allen, "Remote Presence," Abstracts from Flesh & Machines, How Robots Will Change Us, Feb. 2002, pp. 131-147.
Brooks, Rodney, "A Robust Layered Control System for a Mobile Robot," IEEE, Journal of Robotics and Automation, vol. 2, No. 1, Mar. 1986, pp. 14-23.
Celi et al., "The eICU: It's Not Just Telemedicine," Critical Care Medicine, vol. 29, No. 8 (Supplement), Aug. 2001, pp. 183-189.
Cheetham et al., "Interface Development for a Child's Video Conferencing Robot," available online at www.ryerson.ca/pebbles/publications/paper-lea200htes-last.pdf, 2000, 4 pages.
Christensen et al., "BeeSoft User's Guide and Reference," Robots for the Real Word™, Real World Interface, Inc., Sep. 26, 1997, 203 pages.
Chu et al., "Detection of Target Mobile Signal Strength," Technical Development, Motorola Inc., Jan. 1999, pp. 205-206.
Civil Minutes-General: Case No. CV 11-9185PA (AJWx), *InTouch Tech.*, v. *VGO Commons, Inc.*, Sep. 10, 2012, 7 pages.
Cleary et al., "State of the Art in Surgical Robotics: Clinical Applications and Technology Challenges," Feb. 24, 2002, pp. 1-26.
CMU Course 16X62, "Robot User's Manual," (describing the Nomad Scout), Carnegie Mellon University, Feb. 1, 2001, 11 pages.
CNN, "Floating 'Droids' to Roam Apace Corridors of the Future," Available online at http://edition.cnn.com/2000/TECH/space/01/12/psa, Jan. 12, 2000, 3 pages.
cnn.com, "Paging Dr. Robot: Machine Helps Doctors with Patients," Sep. 30, 2003, 3 pages.
Crowley, Susan L., "Hello to Our Future," AARP Bulletin, Jan. 2000, 12 pages.
Dalton, Barnaby, "Techniques for Web Telerobotics," PhD Thesis, University of Western Australia, 2001, 243 pages.
Dario et al., "A Robot Workstation for Diagnosis and Physical Therapy," IEEE Catalog No. $88^{th}$0234-5, 1989, pp. 67-72.
Davies, Brian, "Robotics in Minimall Invasive Surgery," IEE Colloquium on Through the Keyhold: Microengineering in Minimally Invasive Surgery, 1995, pp. 1-2.
Davis, Erik, "Telefriend, Meet iRobot, the Smartest Webcam on Wheels," Wired Magazine, Issue 8.09, Available online at http://www.wired.com/wired/archive/8.09/irobot.html?pg=1&topic=&topic_set+, Sep. 200, 3 pages.
Dean et al., "1992 AAAI Robot Exhibition and Competition," Articles, Al Magazine, vol. 14, No. 1, 1993, 15 pages.
Defendant VGO Communications, Inc.'s Invalidity Contentions Pursuant to the Feb. 27, 2012 Civil Minutes Order, May 2, 2012, 143 pages.
Defendant-Counterclaimant VGO Communications, Inc,'s Supplemental Invalidity Contentions Pursuant to the Feb. 27, 2012 Civil Minute Order, May 14, 2012, 228 pages.
Digiorgio, James, "Is Your Emergency Department of the Leading Edge," Chicago Hospital News, vol. 2, No. 12, 2005, 3 pages.
Dudenhoeffer et al., "Command and Control Architectures for Autonomous Micro-Robotic Forces," FY00 Project Report, Idaho National Engineering and Environmental Laboratory Human Systems Engineering and Sciences Department, Idaho Falls, Apr. 2001, 32 pages.
Elhajj et al., "Real-Time Haptic Feedback in Internet-Based Telerobotic Operation," IEEE International Conference on Electro/information Technology, available online at http://www.egr.msu.edu~ralab-web/cgi_bin/internet-teleoperation.php, Jun. 2000, 10 pages.
Elhajj et al., "Supermedia in Internet-Based Telerobotic Operaitons," Management of Multimedia on the Internet Lecture Notes in Computer Science, Springer-Verlag Berlin Heidelberg, vol. 2216, Oct. 29-Nov. 1, 2001, pp. 359-372.
Elhajj et al., "Synchronization and Control of Supermedia Transmission via the Internet," Proceedings of 2001 International Symposium on Intelligent Multimedia and Speech Processing, May 2-4, 2001, pp. 320-323.

(56) References Cited

OTHER PUBLICATIONS

Ellison et al., "Telerounding and Patient Satisfaction Following Surgery," vol. 199, No. 4, Oct. 2004, pp. 523-530.
Evans et al., "The Trackless Robotic Courier," PYXIS HelpMate®, 2007, 3 pages.
Fels et al., "Developing a Video-Mediated Communication System for Hospitalized Children," Telemedicine Journal, vol. 5, No. 2, 1999, 30 pages.
Fetterman et al., "Videoconferencing Over the Internet," 2001, 8 pages.
Fiorini et al., "Health Care Robotics: A Progress Report," IEEE International Conference on Robotics and Automation, Apr. 20-25, 1997, pp. 1271-1276.
Fong, Terrance, "Collaborative Control: A Robot-Centric Model for Vehicle Teleoperation," Doctoral Dissertation Technical Report CMU-RI-TR-01-34, Robotics Institute, Carnegie Mellon University, Nov. 2001, 197 pages.
Fulbright et al., "SWAMI: An Autonomous Mobile Robot for Inspection of Nuclear Waste of Storage Facilities," Autonomous Robots, vol. 2, 1995, pp. 225-235.
Gaidioz et al. "Synchronizing Network Probes to Avoid Measurement Intrusiveness with the Network Weather Service," Proceedings of the Ninth International Symposium on High-Performance Distributed Computing, 2000, pp. 137-154.
Garner et al., "The Application of Telepresence in Medicine," BT Technology Journal, vol. 15, No. 4, Oct. 1, 1997, pp. 181-187.
Ghiasi et al., "A Generic Web-based Teleoperations Architecture: Details and Experience," Proceedings of SPIE, Telemanipulator and Telepresence Technologies VI, vol. 3840, No. 234, Sep. 19, 1999, 14 pages.
Goldberg et al., "Collaborative Teleoperation via the Internet," IEEE International Conference on Robotics and Automation (ICRA), vol. 2, 2000, pp. 2019-2024.
Goldberg et al., "Desktop Teleoperation via the Word Wide Web," IEEE International Conference on Robotics and Automation, vol. 1, May 21-27, 1995, pp. 654-659.
Goldenberg et al., "Telemedicine in Otolaryngology," American Journal of Otolaryngology, vol. 23, No. 1, 2002, pp. 35-43.
Goldman, Lea, "Machine Dreams," available online at http://www.forbes.com/global/2002/0527/043.html, May 27, 2002, 5 pages.
Gostai, "Gostai Jazz, Robotic Telepresence," available online at http://www.robotshop.com/media/files/gostal-jass-information-sheet.pdf, 4 pages.
Gump, Michael D., Robot Technology Improves VA Pharmacies, U.S. Medicine Informational Central, Jul. 2001, 3 pages.
Han et al., "Construction of an Omnidirectional Mobile Robot Platform Based on Active Dual-Wheel Caster Mechanisms and Development of a Control Simulator," Journal of Intelligent and Robotic Systems, vol. 29, Issue 3, Nov. 2000, pp. 257-275.
Handley et al., "RFC 2327—SDP: Session Description Protocol," available online at http://www.faqs.org/rfcs/rfc2327.html, Apr. 1998, 22 pages.
Hanebeck et al., "ROMAN: A mobile Robotic Assistant for Indoor Service Applications," IEEE/RSJ International Conference on Intelligent Robots and Systems, vol. 2, Sep. 7-11, 1997, pp. 518-525.
Harmo et al., "Moving Eye-Interactive Telepresence Over Internet with a Ball Shaped Mobile Robot," available online at http://automation.tkk.fi/files/tervetaas/Moving_Eye4.pdf, 2000, 6 pages.
Haule et al., Control Scheme for Delayed Teleoperation Tasks, IEEE Pacific Rim Conference on Communications, Computers, and Signal Processing, May 17-19, 1995, pp. 157-160.
Hees, William P., "Communications Design for a Remote Presence Robot," CSCI E-131b, Final Project, Jan. 14, 2002, 12 pages.
Herias et al., "Flexible Virtual and Remote Laboratory for Teaching Robotics," Current Developments in Technology—Assisted Education, Jun. 2006, pp. 1959-1963.
Holmberg et al., Development of a Holonomic Mobile Robot for Mobile Manipulation Tasks, International Journal of Robotics Research, vol. 19, No. 11, Nov. 2000, pp. 1066-1074.
Ishiguro et al., "Integrating a Perceptual Information Infrastructure with Robotic Avatars: A Framework for Tele-Existence," IEEE-RSJ International Conference on Intelligent Robots and Systems, vol. 2, 1999, pp. 1032-1038.
Ishihara et al., "Intelligent Microrobot DDS (Drug Delivery System) Measured and Controlled by Ultrasonics," Intelligent Robots and Systems '91, Intelligence for Mechanical Systems, IEEE/RSJ International Workshop, vol. 2, Nov. 3-5, 1991, pp. 1145-1150.
ITU, "Call Completion Supplementary Services for H.323," ITU-T, Telecommunication Standardization Sector of ITU, H.450.9, Series H: Audiovisual and Multimedia Systems, Nov. 2000, 63 pages.
ITU, "Call Intrusion Supplementary Services for H.323," ITU-T, Telecommunication Standardization Sector of ITU, H.450.11, Series H: Audiovisual and Multimedia Systems, Mar. 2001, 59 pages.
ITU, "Packet-Based Multimedia Communications System," ITU-T, Telecommunication Standardization Sector of ITU, H.323, Series H: Audiovisual and Multimedia Systems, Feb. 1998, 128 pages.
ITU, "Transmission of Non-Telephone Signals: A Far End Camera Control Protocol for Videoconferences Using H.224," ITU-T, Telecommunication Standardization Sector of ITU, H.281, Nov. 1994, 12 pages.
Ivanov, Natali, "Master's Thesis: Internet Based Interface for Control of a Mobile Robot," Department of Numerical Analysis and Computer Science, 2003, 59 pages.
Jacobs et al., "Applying Telemedicine to Outpatient Physical Therapy," AMIA, Annual Symposium Proceedings, 2002, 1 page.
Jenkins et al., "Telehealth Advancing Nursing Practice," Nursing Outlook, vol. 49, No. 2, Mar. 2001, pp. 100-105.
Johanson, Mathias, "Supporting Video-Mediated Communication Over the Internet," Department of Computer Engineering, Chalmers University of Technology, Gothenburg, Sweden, 2003, 222 pages.
Jouppi et al., "BiReality: Mutually-Immersive Telepresence," Proceedings of the 12th Annual ACM International Conference on Multimedia, Oct. 10-16, 2004, pp. 860-867.
Jouppi et al., "First Steps Towards Mutually-Immersive Mobile Telepresence," Proceedings of the 2002 ACM Conference on Computer Supported Cooperative Work, Nov. 16-20, 2002, pp. 354-363.
Kanehiro et al., "Virtual Humanoid Robot Platform to Develop Controllers of Real Humanoid Robots without Porting," IEEE/RSJ International Conference on Intelligent Robots and Systems, vol. 2, 2001, pp. 1093-1099.
Kaplan et al., "An Internet Accessible Telepresence," Multimedia Systems Journal, vol. 5, 1996, 7 pages.
Keller et al., "Raven Interface Project," The National Aviary's Teleconferencing Carnegie Mellon University Robot, Interaction and Visual Interface Design, School of Design, Carnegie Mellon University, 2001, 8 pages.
Khatib et al., "Robots in Human Environments," Proceedings International Conference on Controll, Automation, Robotics, and Vision ICRACV2000, 1999, 15 pages.
Knight et al., "Active Visual Alignment of a Mobile Stereo Camera Platform," IEEE International Conference on Robotics and Automation, vol. 4, Apr. 24-28, 2000, pp. 3203-3208.
Koenen, Rob, "MPEG-4: a Powerful Standard for Use in Web and Television Environments," (KPN Research), available online at http://www.w3.org/Architecture/1998/06/Workshop/paper26, Jul. 1. 2998, 4 pages.
Kurlowicz et al., Can the GestureCAM Be a Surrogate? Proceedings of the fourth European Conference on Computer-Supported Cooperative Work, 1995, pp. 181-196.
Lane, Earl, "Automated Aides," Available online at http://222.cs.com.edu/nursebot/web/press/nd4380.htm, Oct. 17, 2000, 4 pages.
Lee et al., "A Novel Method of Surgical Instruction: International Telementoring," World Journal of Urology, vol. 16, No. 6, Dec. 1998, pp. 367-370.
Leifer et al., "VIPRR: A Virtually in Person Rehabilitation Robot," Proceedings of 1997 International Conference on Rehabilitation Robotics, Apr. 14-15, 1997, 4 pages.
Lemaire, Edward, "Using Communication Technology to Enhance Rehabilitation Services: A Solution Oriented User Manual," Institute of Rehabilitation Research and Development, Terry Fox Mobile Clinic, The Rehabilitation Centre, Ottawa, Ontario, Canada, Version 2.0, available online at http://www.irrd.ca/telehealth/distfile/distman_v2_1.pdf, 104 pages.
Library of Congree, "008-Fixed-Length Data Elements (NR)," MARC 21 Format for Classification Data, available online at http://loc.gov/marc/classification/cd008.html, Jan. 2000, pp. 1-14.

(56) References Cited

OTHER PUBLICATIONS

Lim et al., "Control to Realize Human-Like Walking of a Biped Humanoid Robot," IEEE International Conference on Systems, Man, and Cybernetics, 2000, vol. 5, 2000, pp. 3271-3276.
Linebarger et al., "Concurrency Control Mechanisms for Closely Coupled Collaboration in Multithreaded Virtual Environments," Department of Computer Science and Engineering, Lehigh University, vol. 13, 2004, 40 pages.
Long, William F., "Robot Navigation Technology," available online at http://www.atp.nist.gov/eao/sp950-1/helpmate.htm, Mar. 1999, 3 pages.
Luna, Nancy, "Robot a New Face on Geriatric Care," ocregister.com, Aug. 6, 2003, 3 pages.
Mack, Michael J., "Minimally Invasive and Robotic Surgery," The Journal of the American Medical Association, vol. 285, No. 5, 2001, pp. 568-572.
Mair, G.M., "Telepresence—The Technology and its Economic and Social Implications," Technology and Soceity, 1997, Technology and Society at a Time of Sweeping Change, Proceedings, 1997, International Symposium, Jun. 20-21, 1997, pp. 118-124.
Martin, Anya, "Brighter Days Ahead," Assisted Living Today, vol. 9, Nov./Dec. 2002, pp. 19-22.
McCardle et al., "The Challenge of Utilizing New Technology in Design Education," Loughborough University, IDATER 2000, 2000, pp. 122-127.
Meng et al., "E-Service Robot in Home Healthcare," Proceedings of the 2000 IEEE-RSJ, International Conference on Intelligent Robots and Systems, 2000, pp. 832-837.
Metz, Cade, "HP Labs," available online at http://www.pcmag.com/article2/0.2817.1130820.00.asp, Jul. 1, 2003, 4 pages.
Michaud, Anne, "Introducing Nursebot," available online at http://www.cs.cmu.edu/nursebot/web/press/globe_301/index.html, 2001, 4 pages.
Microsoft Corporation, Inc. "Microsoft NetMeeting 3 Features excerpt from Official Microsoft NetMeeting 3.0 Book," available online at http://technet.microsoft.com/en-us/library/cc723477.aspx, 2012, 6 pages.
Minsky, Marvin, "Telepresence," OMNI Magazine, Jun. 1980, 6 pages.
Montemerlo, Reddy Whittaker, "Telepresence: Experiments in Next Generation Internet," available online at http://www.ri.cmu.edu/creative/archives.htm, Oct. 20, 1998, 3 pages.
Murphy, Robin R., "Introduction to A1 Robotics," A Bradford Book, The MIT Press, Cambridge Massachusetts, London, England, 2000, 487 pages.
Nakajima et al., "A Multimedia Teleteaching System Using an Electronic Whiteboard for Two Way Communication of Motion Videos and Chalkboards," 2nd IEEE International Workshop on Robot and Human Communication, 1993, pp. 436-441.
Nakazato et al., "Group-Based Interface for Content-Based Image Retrieval," Proceedings of the Working Conference on Advanced Visual Interfaces, 2002, pp. 187-194.
Nakazato et al., "ImageGrouper: A Group-Oriented User Interface for Content-Based Image Retrieval and Digital Image Arrangement," Journal of Visual Languages & Computing, vol. 14, No. 4, Aug. 2003, pp. 45-46.
Nersc, "Berkeley Lab's RAGE Telepresence Robot Captures R&D100 Award," Available online at http:/www.nersc.gov/news-publications/news/nersc-center-news/2002/berkley-lab-s-race-telepresence-robot-captures-r-and-d100-award/, Jul. 2, 2002, 2 pages.
Nomadic Technologies Inc., "Nomad XR4000 Hardware Manual," Release 1.0, Mar. 1999, 34 pages.
Noritsugu et al., "Application of Rubber Artificial Muscle Manipulator as a Rehabilitation Robot," Mechatronics, IEEE/ASME Transactions, vol. 2, No. 4, Dec. 1997, pp. 259-267.
North, Michael, "Telemedicine: Sample Script and Specifications for a Demonstration of Simple Medical Diagnosis and Treatment Using Live Two-Way Video on a Computer Network," Greenstar Corporation, 1998, 5 pages.
Ogata et al., "Development of Emotional Communication Robot: WAMOEBA-2R-Experimental Evaluation," Proceedings of the 2000 IEEE/RSJ International Conference on Intelligent Robots and Systems, vol. 1, 2000, pp. 175-180.
Ogata et al., "Emotional Communication Robot: WAMOEBA-2R— Emotion Model and Evaluation Experiments," Proceedings of the International Conference on Humanoid Robots, 2000, pp. 1-16.
Oh et al., "Autonomous Battery Recharging for Indoor Mobile Robots," Proceedings of Australian Conference on Robotics and Automation, 2000, pp. 1-6.
Ojha, Anand K., "An Application of Virtual Reality in Rehabilitation," Proceedings of the 1994 IEEE Southeastcon 94. Creative Technology Transfer—A Global Affair, Apr. 1994, pp. 4-6.
Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.
Osborn, Jim, "Quality of Life Technology Center," QoLT Research Overview: A National Science Foundation Engineering Research Center, Carnegie Mellon University of Pittsburgh, 2 pages.
Panusopone et al., "Performance Comparison of MPEG-4 and H.263+ for Streaming Video Applications," Circuits Systems Signal Processing, vol. 20, No. 3, 2001, pp. 293-309.
Paulos et al., "A World Wide Web Telerobotic Remote Environment Browser," Available online at http://www.w3.org/Conferences/WWW4/Papers/326/, 1995, 15 pages.
Paulos et al., "Designing Personal Tele-Embodiment," Proceedings of IEEE International Conference on Robotics and Automation, vol. 4, May 16-20, 1998, pp. 3173-3178.
Paulos et al., "Personal Tele-Elebodiment," Chapter 9 in Goldberg, et al., ed. "Beyond Webcams," MIT Press, Jan. 4, 2002, pp. 155-167.
Paulos et al., "PRoP: Personal Roving Presence," ACM:CHI Proceedings of CHI '98, 1998, 8 pages.
Paulos et al., "Social Tele-Embodiment: Understanding Presence," Autonomous Robots, vol. 11, Issue 1, Kluwer Academic Publishers, Jul. 2001, pp. 87-95.
Paulos et al., "Ubiquitous Tele-Embodiment: Applications and Implications," International Journal of Human Computer Studies, vol. 46, No. 6, Jun. 1997, pp. 861-877.
Paulos, Eric J., "Personal Tele-Embodiment," Dissertation, Doctor of Philosophy in Computer Science in the Graduate Division of the University of California at Berkeley, 2001, 282 pages.
Paulos, Eric John Canny, "Video of PRoP 2 at Richmond Field Station," www.prop.org Printout of Home Page of Website and two-page transcript of the audio portion of said PRoP Video, May 2001, 2 pages.
Paulos, Eric John, "Personal Tele-Embodiment," Introductory and cover pages from 2201 Dissertation including Contents table, together with emails relating thereto from UC Berkeley Libraries, as shelved at UC Berkeley Engineering Library (Northern Regional Library Facility), May 8, 2002, 25 pages (including 4 pages of emails).
Paulos, Eric John, "Personal Tele-Embodiment," OskiCat Catalog Record, UCB Library Catalog, 2001, 3 pages.
PictureTel Adds New Features and Functionality to Its Award-Winning Live200 Desktop Videoconferencing System, PR Newswire Association, LLC, Gale, Cengage Learning, Jun. 13, 1997, 5 pages.
Picturetel Corporation, "PictureTel Live200 for Windows NT Product Guide," 1997, 63 pages.
Pin et al., "A New Family of Omnidirectional and Holonomic Wheeled Platforms for Mobile Robots," IEEE Transactions on Robotics and Automation, vol. 10, No. 4, Aug. 1994, pp. 480-489.
Piquepaille, Roland, "This Blog and its RSS Feed are Moving," Roland Piquepaille's Technology Trends, How new technologies are modifying our way of life, Oct. 31, 2004, 2 pages.
Radvision, "Making Sense of Bandwidth the Netsense Way," Network Congestion in Unmanaged networks Bandwidth Estimation and Adaptation Techniques, White Paper, Radvision's Netsense Technology, 2010, 7 pages.
Reply Brief for Defendant-Appellee VGO Communications, Inc., Appeal from the U.S. District Court for the Central District of California, in Case No. 2:11-cv-9185, Judge Percy Anderson, May 28, 2013, 75 pages.

(56) References Cited

OTHER PUBLICATIONS

Reply Brief for Plaintiff-Appellant InTouch Technologies, Inc., Appeal from the U.S. District Court for the Central District of California, in Case No. 11-cv-9185, Judge Percy Anderson, Jun. 14, 2013, 39 pages.

Reynolds et al., "Review of Robotic Telemedicine Utilization in Intensive Care Units (ICUs)," 11th Annual ATA Symposium, Tampa, Florida, 2011, 1 page.

Roach, Adam, "Automatic Call back Service in SIP," Internet Engineering Task Force, Internet Draft, Category: Informational, Mar. 2000, 8 pages.

Rovetta et al., "A New Telerobotic Application: Remote Laparaoscopic Surgery Using Satellites and Optical Fiber Networks for Data Exchange," International Journal of Robotics Research, vol. 15, No. 3, Jun. 1, 1996, pp. 267-279.

Roy et al., "Towards Personal Service Robots for the Elderly," Workshop on Interactive Robots and Entertainment (WIRE 2000), available online at <http:www.ri.cmu.edu/pb_files/pub2/roy_nicholas_2000_1.pdf>, vol. 25, Apr. 30-May 1, 2000, 7 pages.

Sachs et al., "Virtual Visit: Improving Communication for Those Who Need it Must," Studies in Health Technology asn Informatics, vol. 94, Medicine Meets Virtual Reality 11, 2003, pp. 302-308.

Salemi et al., "MILO: Personal Robot Platform," IEEE-RSJ International Conference on Intelligent Robots and Systems, Aug. 2005, pp. 4089-4094.

Sandt et al., "Perceptions for a Transport Robot in Public Environments," Proceedings of the 1997 IEEE/RSJ International Conference on Intelligent Robots and Systems, vol. 1, Sep. 7-11, 1997, pp. 360-365.

Sawyer, Robert J., "Inventing the Future: 2000 years of Discovery," available online at http://www.sfwriter.com/pritf.htm, Jan. 2, 2000, 2 pages.

Schaeffer et al., "Care-O-BotTM: The Concept of a System for Assisting Elderly or Disabled Persons in Home Enviornments," Proceedings of the 24th Annual Conference of the IEEE Industrial Electronics Society, vol. 4, 1998, pp. 2476-2481.

Schraft et al., "Care-O-bot™: The Concept of a System for Assisting Elderly or Disabled Persons in Home Environments," IEEE Proceedings of the 24th Annual Conference of the Industrial Electronics Society, IECON '98, Aug. 31-Sep. 4, 1998, pp. 2476-2481.

Schultz et al., "Web Interfaces for Mobile Robots in Public Places," IEEE Robotics & Automation Magazine, vol. 7, No. 1, Mar. 2000, pp. 48-56.

Screenshot Showing Google Date for Lemaire Telehealh Manual, screenshot retrieved on Dec. 18, 2014, 1 page.

Shimoga et al., "Touch and Force Reflection for Telepresence Surgery," Proceedings of the 16th Annual International Conference of the IEEE Engineering in Medicine and Biology Society, Nov. 1994, pp. 1049-1050.

Siegwart et al., "Interacting Mobile Robots on the Web," Proceedings of the 1999 IEEE International Conference on Robotics and Automation, May 1999, pp. 1-7.

Simmons et al., "Xavier: An Autonomous Mobile Robot on the Web," IEEE Robotics and Automation Magazine 1999, pp. 43-48.

Stephenson, Gary, "Dr. Robot Tested at Hopkins," available online at http://www.hopkinsmedicine.org/press/2003/august/030805.htm, Aug. 5, 2003, 2 pages.

Stoianovici et al., "Robotic Tools for Minimally Invasive Urologic Surgery," Complications of Urologic Laparoscopic Surgery: Recognition, Management and Prevention, Dec. 2002, 17 pages.

Suplee, Curt, "Mastering the Robot," The Washington Post, Washington Post Staff Writer, Sep. 17, 2000, 5 pages.

Tahboub et al., "Dynamics Analysis and Control of a Holonomic Vehicle with Continuously Variable Transmission," Transactions of the ASME, Journal of Dynamic Systems, Measurement and Control, vol. 124, Mar. 2002, pp. 118-126.

Telepresence Research, Inc., "The Telepresence Mobile Robot System," available online at http://www.telepresence.com/telepresence-research/TELEROBOT/, Feb. 20, 1995, 3 pages.

Tendick et al., "Human-Machine Interfaces for Minimally Invasive Surgery," Proceedings of the 19th Annual International Conference of the IEEE Engineering in Medicine and Biology Socieity, Oct. 30-Nov. 2, 1997, pp. 2771-2776.

Theodosiou et al., MuLVAT: A Video Annotation Tool Based on XML-Dictionaries and Shot Clustering, 19th International Conference, Artificial Neural Networks—ICANN 2009, Part II, Sep. 14-17, 2009, pp. 913-922.

Thrun et al., "Probabilistic Algorithms and the Interactive Museum Tour-Guide Robot Minerva," International Journal of Robotics Research, vol. 19, 20000, pp. 1-35.

Time, Lists, "Office Coworker Robot," Bestr Inventions of 2001, available online at http://content.time.com/time/specials/packages/article/0,28804.136165_1936255_1936640.00.html, Nov. 19, 2001, 2 pages.

Tipsuwan et al., "Gain Adaptation of Networked Mobile Robot to Compensate QoS Deterioration," 28th Annual Conference of the Industrial Electronics Society, vol. 4, Nov. 5-8, 2002, pp. 3146-3151.

Tsui et al., "Exploring Use Cases for Telepresence Robots," 6th ACM/IEEE International Conference on Human-Robot Interaction (HRI), Mar. 2011, pp. 11-18.

Tyrrell et al., "Teleconsultation in Psychology: The Use of Videolinks for Interviewing and Assessing Elderly Patients," Age and Ageing, vol. 30, No. 3, May 2001, pp. 191-195.

Tzafestas et al., "VR-Based Teleoperation of a Mobile Robotic Assistant: Progress Report," Technical Report DEMO 2000/13, Institute of Informatics and Telecommunications, National Center for Scientific Research "Demokritos," Nov. 2000, pp. 1-23.

Umass Lowell Robotics Lab, "Robotics Lab @ UMASS Lowell," Borchure, 2011, 2 pages.

Urquhart, Kim, "InTouch's Robotic Companion 'Beams Up' Healthcare experts," Medical Device Daily, vol. 7, No. 39, Feb. 27, 2003, pp. 1, 4.

Using Your Infrared Cell Phone Camera, available online at http://www.calsdomain.com/xray/about.htm, Courtesy of Internet Wayback Machine, Jan. 30, 2010, 4 pages.

Video Middleware Cookbook, "H.350 Directory Services for Multimedia," 2 pages.

Weaver et al., "Monitoring and Controlling Using the Internet and Java," Proceedings of the 25th Annual Conference of the IEEE Industrial Electronics Society, vol. 3, 1999, pp. 1152-1158.

Weiss et al., "PEBBLES: A Personal Technology for Meeting Education, Social and Emotional Needs of Hospitalised Children," Personal and Ubiquitous Computing, vol. 5, No. 3, Aug. 2001, pp. 157-168.

Weiss et al., "Telework and Video-Mediated Communication: Importance of Real-Time, Interactive Communication for Workers with Disabilities," available online at http://www.telbotics.com/research_3.htm retrieved on Nov. 23, 2010, 3 pages.

West et al., "Design of Ball Wheel Mechanisms for Omnidirectional Vehicles with Full Mobility and Invariant Kinematics," Journal of Mechanical Design, vol. 119, Jun. 1997, pp. 153-161.

Yamasaki et al., "Applying Personal Robots and Active Interface to Video Conference Systems," International Conference on Human Computer Interaction, vol. B, 1995, pp. 243-248.

Yamauchi, Brian, "PackBot: A Versatile Platform for Military Robotics," Proceedings of SPIE for Military Robotics, 2004, pp. 228-237.

Yong et al., "Robot Task Execution with Telepresence Using Virtual Reality Technology," 1998 International Conference on Mechatronic Technology, Nov. 30-Dec. 2, 1998, pp. 1-8.

Zambroski, James, "CMU, Pitt Developing Nursebot," available online at http://www.cs.cmu.edu/~nursebot/web/press/tribunereview.html, Oct. 27, 2000, 3 pages.

Zamrazil, Kristie, "Telemedicine in Texas: Public Policy Concerns," Focus Report, House Research Organization, Texas House of Representatives, No. 76-22, May 5, 2000, pp. 1-16.

Zipperer, Lorri, "Robotic Dispensing System," ISMP Medical Safety Alert!, vol. 4, No. 17, Aug. 25, 1999, 2 pages.

Zorn, Benjamin G., "Ubiquitous Telepresence," Department of Computer Science, University of Colorado, 1996, 13 pages.

* cited by examiner

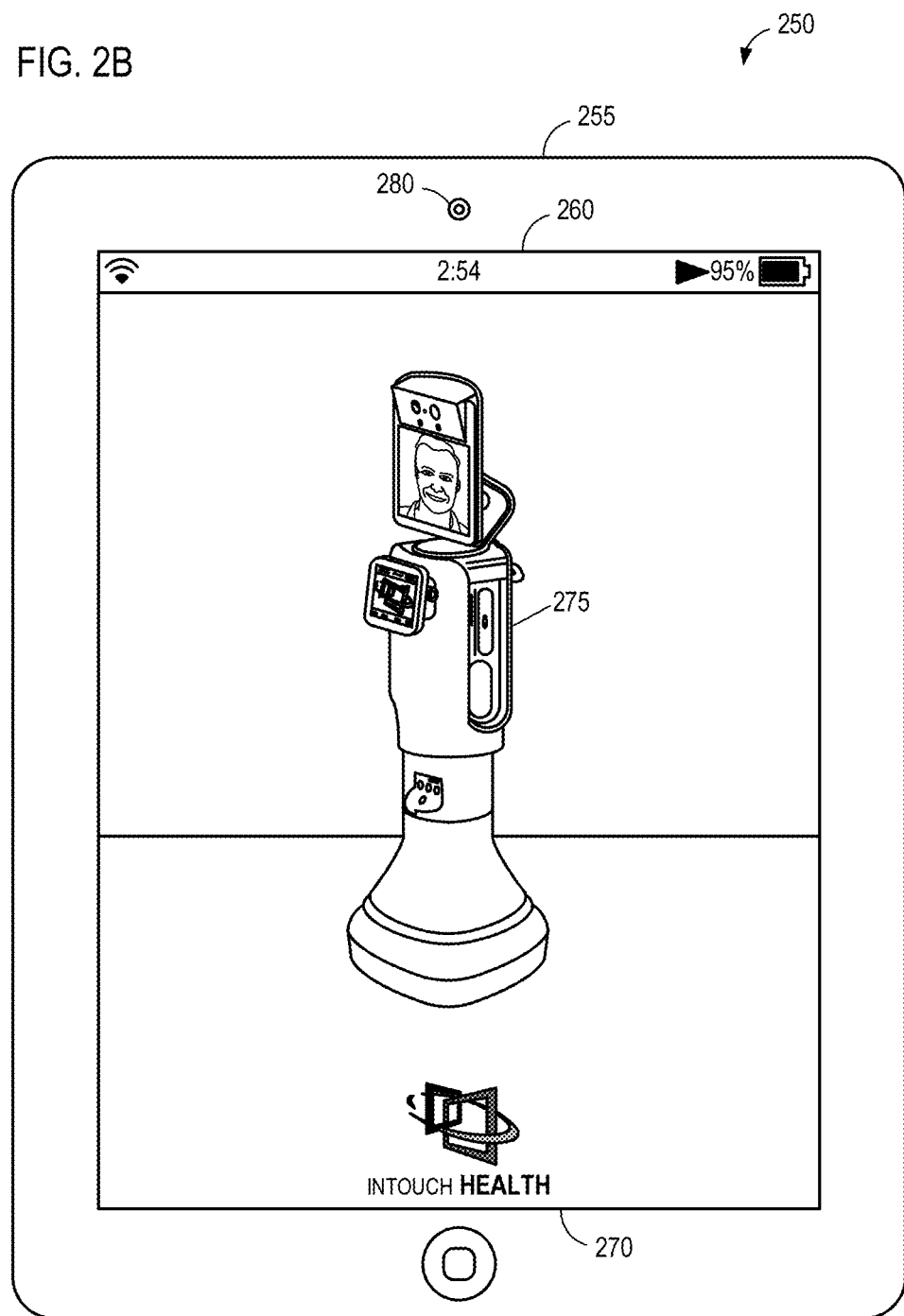

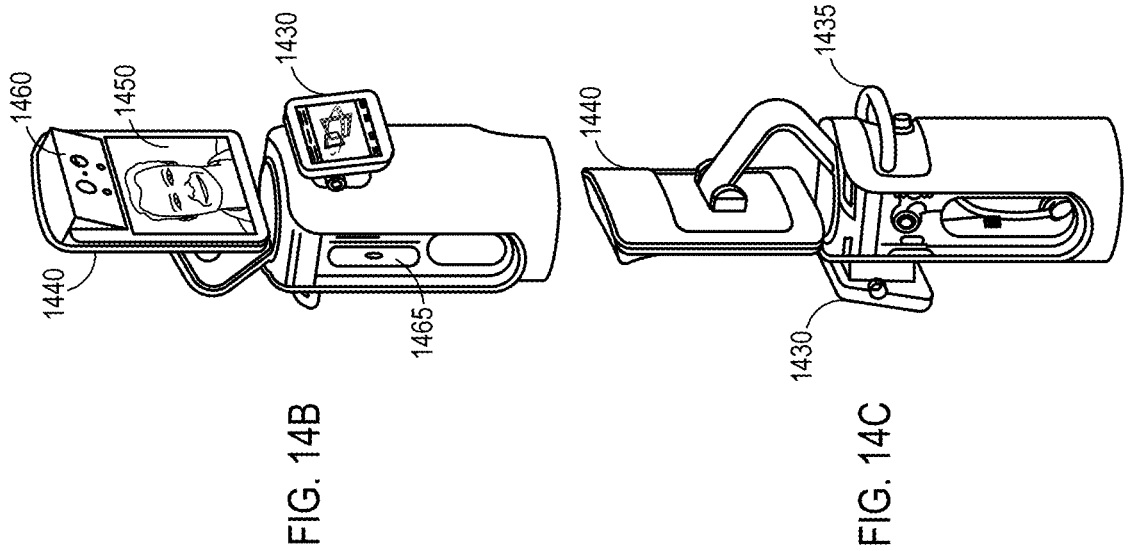
FIG. 14B
FIG. 14C
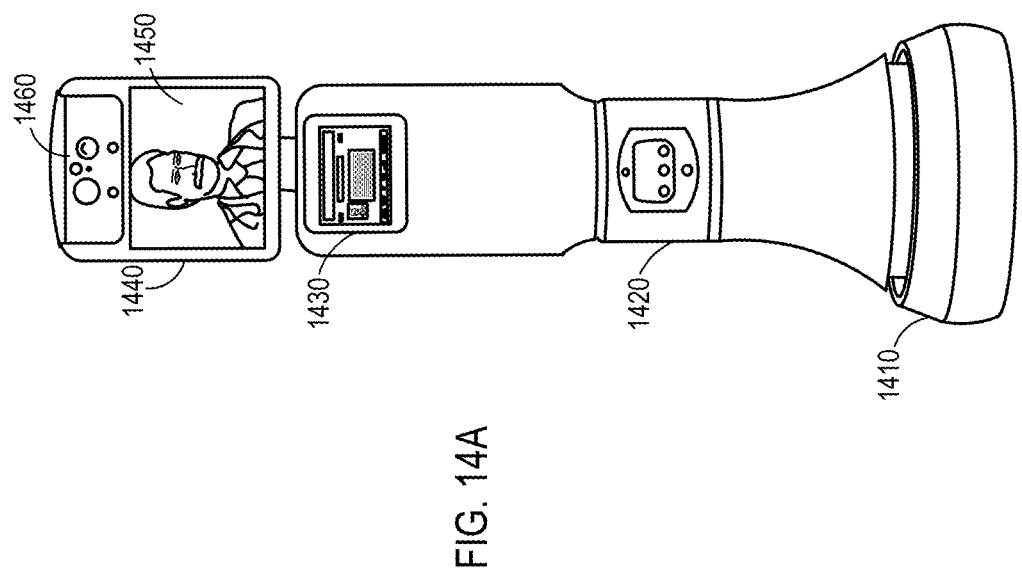
FIG. 14A

GRAPHICAL USER INTERFACES INCLUDING TOUCHPAD DRIVING INTERFACES FOR TELEMEDICINE DEVICES

RELATED APPLICATIONS

This U.S. Patent Application is a continuation of U.S. patent application Ser. No. 15/154,518, filed May 13, 2016, titled "Graphical User Interfaces Including Touchpad Driving Interfaces for Telemedicine Devices," which is a continuation of U.S. patent application Ser. No. 14/550,750 filed Nov. 21, 2014, titled "Graphical User Interfaces Including Touchpad Driving Interfaces For Telemedicine Devices," which is a continuation of PCT Application No. PCT/US2013/031743 (the "PCT Application"), and claims priority under 35 U.S.C. § 119(e) to: U.S. Provisional Application No. 61/650,205 filed May 22, 2012, titled "Remote Presence Interface and Patient Data Integration;" U.S. Provisional Application No. 61/674,794 filed Jul. 23, 2012, titled "Graphical User Interfaces Including Touchpad Driving Interfaces for Telemedicine Devices;" U.S. Provisional Application No. 61/674,796 filed Jul. 23, 2012, titled "Clinical Workflows Utilizing Autonomous and Semi-Autonomous Telemedicine Devices;" U.S. Provisional Application No. 61/674,782 filed Jul. 23, 2012, titled "Behavioral Rules For a Telemedicine Robot To Comply With Social Protocols;" U.S. Provisional Application No. 61/766,623 filed Feb. 19, 2013, titled "Graphical User Interfaces Including Touchpad Driving Interfaces for Telemedicine Devices;" which applications are all hereby incorporated by reference in their entireties.

TECHNICAL FIELD

This disclosure relates to interactive and display interfaces for telepresence devices in healthcare networks. More specifically, this disclosure provides various graphical user interfaces and interactive interfaces for remote presence devices.

BRIEF DESCRIPTION OF THE DRAWINGS

Non-limiting and non-exhaustive embodiments of the disclosure are described herein, including various embodiments of the disclosure illustrated in the figures listed below.

FIG. 2B illustrates an embodiment of an initial launch page for an RPI or other application associated with a telepresence device intended to induce a user to orient a PED in a portrait orientation.

FIGS. 14A-C illustrate exemplary embodiments of a telepresence device.

Figure 1:
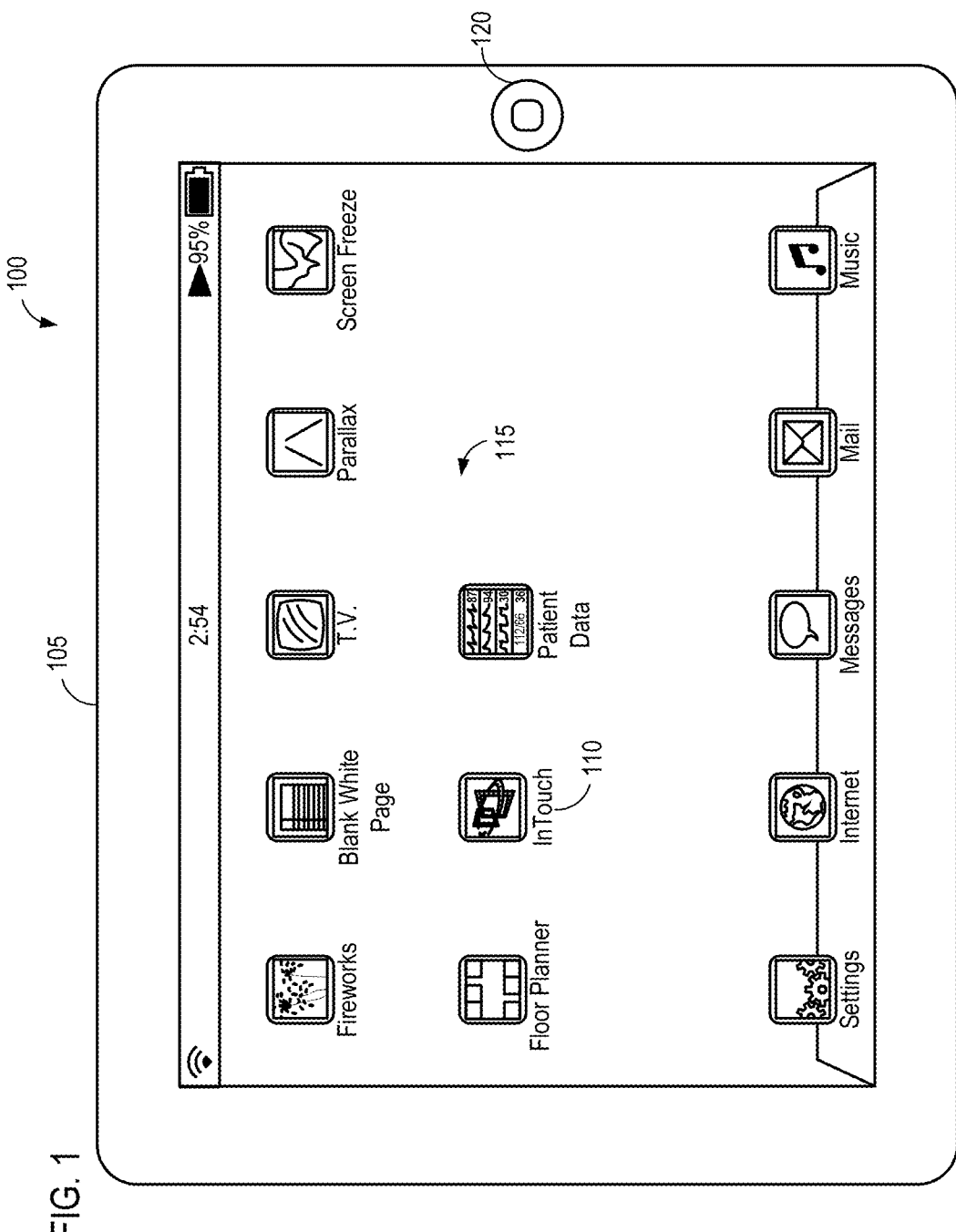
FIG. 1 illustrates an embodiment of a home page of a portable electronic device (PED), including an application providing a remote presence interface (RPI) for interacting with a telepresence device.

The described features, structures, and/or characteristics of the systems and methods described herein may be combined in any suitable manner in one or more alternative embodiments, and may differ from the illustrated embodiments.

DETAILED DESCRIPTION

Healthcare facilities may include telemedicine technologies, such as telepresence devices in a telepresence network, that allow remote healthcare practitioners to provide services to patients and/or other healthcare practitioners in remote locations. For example, a remote healthcare practitioner may be a neurologist practicing in a relatively large hospital who may, via a telepresence device, provide services and consultations to patients and/or other medical professionals in a relatively small hospital that may otherwise not have a neurologist on staff.

The present disclosure provides various interfaces for visualizing, controlling, and driving telepresence devices. In a remote presence (RP) system, a telepresence device, such as an autonomous or semi-autonomous robot, may communicate with an interfacing device via a communications network. In various embodiments, a portable electronic device (PED) may be used to run a remote presence interface (RPI) adapted to provide various telepresence functions.

In various embodiments, an RPI application may be executed on a device configured as a stand-alone PED configured to solely run the RPI application. Alternatively, the RPI application may be executed by any of a wide variety of PEDs configured as multi-purpose PEDs, such as the Apple iPad®. In various embodiments, a user may launch an RPI application and login using login credentials. The login process may utilize any of a wide variety of encryption algorithms and data protection systems. In various embodiments, the login process may meet or exceed standards specified for Health Insurance Portability and Accountability Act (HIPAA) compliance.

A user may select one or more endpoint telepresence devices via the RPI. Once a secure connection is established, the RPI may display a video feed from the telepresence device on the PED. In addition, the RPI may include any number of navigational panels, setting controls, telemetry data displays, map views, and/or patient information displays.

In some embodiments, the RPI may allow a user to manually, semi-autonomously, or autonomously control the movement of the telepresence device. The RPI may allow a user to specify movement (i.e., a location within a healthcare facility or a physical movement, such as a head turn, of the telepresence device) using a destination selection panel, an arrow, a physical or virtual joystick, a touch pad, click-to-destination, vector based driving, mouse-based vector driving, and/or other navigational control.

For example, a user may provide a navigation input by selecting a location within a live video feed (e.g., via a click or a touch). The navigation input may be used to transmit navigation instructions to a remote telepresence device. For instance, in a click drive mode, the selection of a location within the live video feed may be used to navigate the telepresence device to the selected location. The selection of a location on a floor or hallway may result in navigation instructions that cause the telepresence robot to autonomously or semi-autonomously navigate to the selected location.

In some embodiments, an operator may input a navigation input in the form a navigation vector provided (e.g., drawn, traced, mapped) with respect to the live video feed. The navigation vector may include a length on the display and/or other input device (e.g., touchpad) and an angle with respect to plane of the display and/or other input device. As an example, a plane of the display and/or other input device may be described with a Cartesian coordinate system as having an x-axis and a y-axis. The navigation vector may be provided with respect to the display plane and described as having an x-axis component (horizontal direction) and a y-axis component (vertical direction).

According to various embodiments, a navigation input provided as a navigation vector may be decomposed into a horizontal (x-axis) component and a vertical (y-axis) component. The length and sign (i.e., positive or negative value) of the horizontal component of the navigation vector may be used to determine a magnitude and direction of a rotational velocity and/or an angular displacement of a telepresence device. The length of the vertical component of the navigation vector may be used to determine the magnitude of a forward velocity and/or a forward displacement of a telepresence device.

The length of the horizontal component may be used to determine the magnitude of the rotational velocity and/or angular displacement using a scaling function. The scaling function may be constant, linear, and/or non-linear. Thus, using a non-linear scaling function, a first horizontal component twice as long as a second horizontal component may not result in a first rotational velocity double that of the second rotational velocity. Similarly, the length of the vertical component may be used to determine the magnitude of the forward velocity and/or forward displacement using a scaling function. Again, the scaling function may be constant, linear, and/or non-linear. The scaling function used to translate the horizontal component may be different than the scaling function used to translate the vertical component.

Alternatively, selectively, and/or in a different navigation mode, the selection of a location within the live video feed may be used to generate a navigation vector, where the length of the vector corresponds to the velocity at which the telepresence device should navigate and/or the distance the telepresence device should navigate, and the angle of the vector corresponds to the direction the telepresence device should navigate. For instance, a navigation input may be in the form of a vector drawn as either a final endpoint selection or as a vector including a beginning point and an end point. The end point of the vector may represent the location to which the telepresence device should navigate (i.e., a desired navigation point). Navigation instructions may be generated based on the current location of the telepresence device and the endpoint of the vector within the live video feed. According to some embodiments, the vector's image pixel endpoint may be mapped via a lookup table to one or more translate and rotate commands to cause the telepresence device to navigate to the selected location. In some embodiments, the length of the vector may correspond to the desired distance to move the telepresence device, a desired acceleration of the telepresence device, and/or a desired velocity of the telepresence device.

As an example, a navigation input may be received that directs a telepresence device to navigate forward (with respect to the live video feed) 3 meters and to the right 2 meters. Any of a wide variety of navigation instructions may be possible to correctly navigate the telepresence device. For instance, the navigation instructions may direct the telepresence device to navigate approximately 3.6 meters at a 34 degree angle relative to the video feed. Alternatively, the navigation instructions may direct the telepresence device to navigate 3 meters forward and then 2 meters to the right. As will be appreciated, any number of navigations routes and corresponding navigation instructions may be possible. The navigation input may be translated into navigation instructions as a plurality of drive forward commands coupled with rotate commands.

In various embodiments, the navigation instructions are derived from a navigation input indicating a desired direction and/or location and the current location of the telepresence device. In some embodiments, the live video feed may be delayed slightly due to network and/or processing limitations. For example, a live video feed may be delayed by a few tenths of a second or even by a few seconds. This video latency may result in inaccurate navigation instructions. Accordingly, the navigation input may be adjusted based on the known video latency and the velocity and direction of the robot.

Returning to the example above, if the telepresence device were traveling at 1.25 meters per second in a forward direction relative to the live video feed and the video latency was 0.8 seconds, then the telepresence device will have already traveled 1 of the desired 3 meters when the selection is made. Accordingly, the selection of a location 3 meters ahead and 2 meters to the right, may be translated or mapped to navigation instructions that cause the telepresence device to travel 2 meters forward and 2 meters to the right (or 2.8 meters at a 45 degree angle) to compensate the movement of the telepresence device. Thus, the navigation instructions may be adjusted based on the latency of the video feed.

In various embodiments, a navigation input in the form of a vector (such as a vector provided in a mouse-based vector input mode) may be translated into navigation instructions through the use of a lookup table. In some embodiments, the lookup table may include values that compensate for latency. That is, the navigation instructions returned by the lookup table may be based on the navigation input and the current or recent average video latency.

Various alternative navigation systems, methods, and processing steps may be used in conjunction with the presently described remote presence interface, including those described in U.S. Pat. No. 6,845,297, titled "Method and System for Remote Control of Mobile Robot," filed on Jan. 9, 2003, and European Patent No. 1279081, titled "Method and System for Remote Control of Mobile Robot," filed on May 1, 2001, which applications are hereby incorporated by reference in their entireties.

The RPI may provide various notifications associated with the network connection, the PED, a patient, a healthcare facility, a healthcare practitioner, a telepresence device, and/or the like. The RPI may include a media management module configured to allow a user to record and/or store audio and/or visual data for subsequent use. A settings panel may allow settings on the PED and/or the telepresence device to be adjusted. In some views, multiple windows may provide quick access to various panels of information. For example, one or more panels associated with a video feed, patient data, calendars, date, time, telemetry data, PED data, telepresence device data, healthcare facility information, healthcare practitioner information, menu tabs, settings controls, and/or other features may be displayed simultaneously and/or individually in a full-screen mode.

The RPI may utilize a camera of the PED to capture an image of the user of the PED and project the image on a screen on the telepresence device. In some embodiments, the image on the screen of the telepresence device may be modified and/or enhanced. In one embodiment, an avatar representing the user of the PED is displayed on the PED. In some embodiments, the RPI may encourage or induce a user to utilize the PED with a front-facing camera at or above eye-level. Similarly, the RPI may encourage or induce a user to utilize the PED with a front-facing camera approximately centered on a user's face. For instance, on an Apple iPad®, the RPI may encourage a user to utilize the iPad® in a portrait mode for many tasks in order to maintain a more natural perspective of the user for projection via the screen on the telepresence device.

In various embodiments, the RPI may facilitate conference sessions with more than two people interacting via a combination of PEDs and/or telepresence devices. For example, multiple healthcare practitioners may participate in a remote consultation. In such an example, each healthcare practitioner may utilize an RPI on a PED to access a telepresence device at a bedside of a patient. The remote presence system, via the network, servers, RPIs, and/or telepresence devices, may facilitate the multi-user experience.

The RPI may incorporate sub-applications and/or provide access to related applications, such as a StrokeRESPOND application configured to provide one or more functions and/or workflow processes described in U.S. patent application Ser. No. 12/362,454, titled "DOCUMENTATION THROUGH A REMOTE PRESENCE ROBOT," filed on Jan. 29, 2009, which application is hereby incorporated by reference in its entirety.

As described herein and illustrated in various embodiments, the display of a PED may be utilized by the RPI to display any combination of video feed panels, informational panels, data panels, setting control panels, navigation panels, and/or panels providing access to any of various functions made accessible via the RPI. The RPI may be configured to maintain a "stateful" connection at the application layer, such that a session and/or variables may be continued and/or maintained in the event that the connection is lost or dropped. The RPI application may attempt to re-establish a disconnected session using saved or logged variables in the event a connection is lost or dropped. The PED and/or RPI application may have settings that enable a user to maximize frame rate or image quality at the expense of the battery life of the device, or vice versa.

The RPI may include an information bar ("status bar") that displays various status information related to the PED, including battery life, wireless connection strength, wireless connection name or SSID, or the current time. The RPI may include one or more toolbars. A toolbar may be disposed along the top edge of the upper pane of the RPI. The toolbar may be manually hidden by touching or selecting an icon or a specified area of the display, or the toolbar may auto-hide after a period of time. Once hidden, the user may un-hide the toolbar by touching, selecting, or otherwise moving an input device on or around an icon or specified area of the display.

The RPI may include a "Picture-in-Picture" region or window that displays local video or image data currently being captured by the camera of the PED. The local video feed may be captured from a camera either incorporated within or otherwise in communication with the PED. The user may resize the local video window, reposition it within the display, and/or remove it. The local video window may be displayed in a lower pane of the GUI, while the remote video is displayed in the upper pane, or vice versa.

The RPI may include an in-video interface that enables the user to control the endpoint device by interacting with the live video feed. For example, when the user touches, taps, clicks, or otherwise selects a point in the live video feed, the endpoint may change a mechanical pan or tilt, or digital pan or tilt, or both, such that the point selected by the user is centered in the live video feed. The user may also adjust an optical or digital zoom, or both, of the live video feed. For example, a user may adjust an optical and/or digital zoom by pinching together or spreading apart two or more fingers on the surface of a touch sensitive display of the PED. As another example, the user may control all or some of a mechanical or digital pan, tilt, or zoom of the live video feed by pressing and dragging a finger on the surface of the display to specify a diagonal or other dimension of a zoom region. After a period of time or upon releasing his or her finger, the endpoint may mechanically or digitally pan, tilt, or zoom to match a dimension of the zoom region to a dimension of the live video feed, and/or to match a center of the zoom region to a center of the live video feed. In one embodiment, a user may zoom out to a default zoom (which may be fully zoomed out) by performing a double-tap in the live video feed, or by double-clicking or right-clicking a mouse cursor within the live video feed.

In one embodiment, the user may direct movement of a telemedicine device (or other telepresence device) to a particular location within the live video feed by performing a "touch-hold-tap," where the user touches a location on the screen, holds his or her finger on that location for a brief interval until a cursor appears on the screen under the user's finger, positions the cursor (which now follows the user's finger) at a point in the remote video window representing the desired destination, and subsequently taps his or her finger once again to confirm the location as the desired destination. The telepresence device may then proceed to a position in the live video feed corresponding to the location selected by the user.

Additional functionalities available via the RPI through a touch screen interface may include a two-finger swipe to display video from one or more auxiliary video sources, such as a video camera, still camera, endoscope, ultrasound device, radiological imaging device, magnetic resonance imaging device, or other medical imaging device.

A toolbar may be shrunken and/or expanded (vertically or horizontally, or both), or hidden and unhidden, by touching or tapping an icon disposed at the top of the screen. For example, an icon may have the appearance of an arrow or triangle that points "up" when the toolbar is fully expanded or unhidden, and may point "down" when the toolbar is shrunken or hidden. The icon itself may shrink or expand with the toolbar. Alternatively, the toolbar may be unhidden by the user "pulling down" or making a downward swipe from the top (or other edge) of the screen. The toolbar may again be hidden by "pushing up" or making a swipe toward the top (or other edge) of the screen.

Additional functions or applications may be accessed from the toolbar. Each function or application may have a distinctive icon in the toolbar indicative of the underlying functionality. If there are more functions/icons available than can be displayed on the toolbar, the toolbar may be configured to scroll icons onto and off of the toolbar with a swipe of the user's finger in the toolbar. The icons may scroll continuously in a carousel fashion, or the scrolling may be disabled in a particular direction when there are no further icons to be displayed, thus informing the user of this fact. Alternatively, the toolbar may not scroll available icons, but instead show only a specified set of icons. In this case, additional functions or applications would be exposed to the user via additional menu levels, windows, or pop-overs, accessible via one or more icons contained in the toolbar or elsewhere in the RPI.

The toolbar may provide access to various functions of the RPI such as activating or deactivating a headset or handset (which may be coupled to the telepresence device, in either a wired or wireless fashion) when additional privacy is desired in communicating with the remote user (i.e., the user at the control station/PED); activating or deactivating a stethoscope for monitoring a patient; creating a still image or snapshot from a camera (still or video) on or otherwise coupled to the telepresence device or any auxiliary input; starting or stopping recording video from a camera on or coupled to the telepresence device or any auxiliary input; navigation features; opening or bringing up a map or list of destinations (e.g., people's names associated with a device or location); reversing local camera view (toggle local video to come from front of the PED or back of the PED); activating or deactivating remote pointer (cursor on remote display follows or mirrors cursor position on local display, which is positioned by the user tapping or touching the desired location on the display); activating or deactivating a laser pointer on the remote device (a laser pointer may be positioned on the telepresence device so as to correspond to a position of tap or touch within the live video feed); muting or un-muting a microphone of the PED; opening the settings panel; disconnecting; and/or other features, options, and/or settings.

From the lower pane of the RPI, the user may initiate a vector drive mode for controlling a telepresence device. For example, a mouse click, touch-drag motion, or other action may be used to "draw" or otherwise input a vector for controlling the motion of a telepresence device. For example, a user may touch two fingers in the lower pane and drag them a desired distance and direction on the screen to send a drive command with a respective velocity and heading to the mobile telepresence device.

The interface may further include a mechanism for deactivating an obstacle detection/obstacle avoidance (ODOA) system, such that the user may operate in a "nudge mode" and continue to slowly move the telepresence device despite the telepresence being in contact with or close proximity to another object. This mechanism may automatically time-out such that the ODOA system is re-engaged after a period of inactivity. Placing the telepresence device in nudge mode may cause a camera of the telepresence device to be automatically positioned to look down around the body of the telepresence device and either in the direction of drive command issued by the user or in the direction of an object closest to or in contact with the telepresence device (so that the user may see what obstacle he or she is commanding the telepresence device to nudge). Alternatively, the ODOA system may be entirely deactivated. In one embodiment, the ODOA system may be deactivated so long as the telepresence device is driven or moved below a specified velocity.

The RPI may be configured for deployment on any of a wide variety of PEDs, including the Apple iPad®, iPod®, and iPhone®. The RPI may be configured for deployment on any of a wide variety of PEDs, such as mobile phones, computers, laptops, tablets, and/or any other mobile or stationary computing device. In some embodiments, the RPI may be presented via a plug-in or in-browser application within a standard web browser.

In some embodiments, the RPI may allow for varying feature sets depending on the type of PED utilized. For example, on a larger tablet-sized PED, the RPI may include any combination of the numerous features described herein. While on a smaller PED, such as an Apple iPhone®, the available features may be limited to suit a particular context or use-case. In one embodiment, the RPI may allow a user, such as nurse or hospital staffer, to control the movement of a telepresence device without establishing a telepresence audio/video session. In other embodiments, for example, a remote family member of a patient may conduct a two-way voice and video telepresence with his or her iPhone, but may not have permission to drive or otherwise control the movement of the telepresence device. Any number of features or combination of features may be included and/or excluded for a particular PED.

As an example scenario, a nurse may utilize an RPI on a PED with limited functionality, such as an Apple iPhone®, to request a cardiac consult for a patient. A telepresence system in contact with the RPI submits the request to a telepresence device. The telepresence device may begin navigating to the patient while simultaneously initiating a connection with a cardiac doctor. For example, the telepresence device may call an appropriate cardiac doctor (e.g., the cardiologist on call, the nearest cardiologist, the patient's specific cardiologist, etc.) on one or more PEDs belonging to the doctor. Given that the nurse is using a PED with limited functionality, the nurse may be allowed to control the telepresence device and/or participate in an audio-only telepresence session, but may be provided a limited feature set. Accordingly, the nurse may be able to communicate with the doctor as the telepresence device navigates to the patient.

In some embodiments, the nurse or a patient may request a doctor (or a specific type of doctor) via an RPI or via a display interface directly on a telepresence device. The RPI, the telepresence device, and/or a corresponding telepresence system may intelligently call a specific doctor as described herein. Alternatively, the RPI, the telepresence device, and/or a corresponding telepresence system may call a plurality of doctors. In such a scenario, the first doctor to attend may be connected via an RPI to a telepresence device to service the request of the nurse or patient. The call routing and telepresence session may be managed in a network cloud, a telepresence network, and/or via some other suitable computing device.

Throughout the specification, various functions, features, processing, and/or other computing actions are described as being performed by at least one of an RPI, a PED, a telepresence system, and/or other computing device. It will be appreciated that in many instances, the actual processing, calling, function implementation, recording, and/or other computer-performed actions may be executed on a local device, a remote device, and/or via networked or cloud device.

Reference throughout this specification to "one embodiment" or "an embodiment" means that a particular feature, structure, or characteristic described in connection with the embodiment is included in at least one embodiment. Thus, the appearances of the phrases "in one embodiment" and "in an embodiment" in various places throughout this specification are not necessarily all referring to the same embodiment. In particular, an "embodiment" may be a system, an article of manufacture (such as a computer-readable storage medium), a method, and/or a product of a process.

The phrases "connected to" and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

Types of telepresence devices include, but are not limited to, remote telepresence devices, mobile telepresence units, and/or control stations. For example, a remote telepresence device may include a telepresence robot configured to move within a medical facility and provide a means for a remote practitioner to perform remote consultations. Additionally, telepresence devices may comprise any of a wide variety of endpoint devices, such as those described in U.S. patent application Ser. No. 13/360,579 filed on Jan. 27, 2012, titled "INTERFACING WITH A MOBILE TELEPRESENCE ROBOT," which application is hereby incorporated by reference in its entirety. Telepresence devices may also comprise any of the endpoint devices described in U.S. patent application Ser. No. 13/360,590 filed on Jan. 27, 2012, titled "INTERFACING WITH A MOBILE TELEPRESENCE ROBOT," which application is hereby incorporated by reference in its entirety.

A "portable electronic device" (PED) as used throughout the specification may include any of a wide variety of electronic devices. Specifically contemplated and illustrated are tablet-style electronic devices, including, but not limited to, electronic readers, tablet computers, tablet PCs, cellular phones, interactive displays, video displays, touch screens, touch computers, and the like. Examples of PEDs include the Apple iPad®, iPod®, and iPhone®, the Hewlett Packard Slate®, the Blackberry Playbook®, the Acer Iconia Tab®, the Samsung Galaxy®, the LG Optimus G-Slate®, the Motorola Xoom,® the HP touchpad Topaz®, the Dell Streak®, and the like.

Throughout this description, a tablet-style touch-screen PED is used as an exemplary PED; however, any of a wide variety of PEDs and/or other electronic devices may be used instead. For instance, tablet computing devices, cellular phones, computers, laptops, etc., could be used in place of the illustrated and described touch-screen tablet devices. It will be appreciated by one of skill in the art that operations and functions performed on or by a PED may also be performed on a stationary portable electronic device, such as a desktop computer or server.

The embodiments of the disclosure may be understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations and/or components are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless otherwise specified.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware. Accordingly, the various components, modules, systems, and/or features described herein may be embodied as modules within a system. Such a system may be implemented in software, firmware, hardware, and/or physical infrastructure.

Embodiments may also be provided as a computer program product including a non-transitory machine-readable medium having stored thereon instructions that may be used to program or be executed on a computer (or other electronic device, such as a PED) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable media suitable for storing electronic instructions.

FIG. 1 illustrates an embodiment 100 of a home page of a portable electronic device (PED) 105. The PED 105 may include one or more physical buttons, such as button 120, and a display screen. The display screen may be a touch-screen configured to allow a user to provide input via the touch screen. The PED 105 may be configured to display various icons 115 to launch corresponding applications. In various embodiments, a remote presence interface (RPI) icon 110 may be used to launch an RPI application for interfacing with a telepresence device. An RPI according to any of the various embodiments described herein may alternatively be utilized on any of a wide variety of computing platforms and using any of a wide variety of programming tools and languages.

Figure 2A:
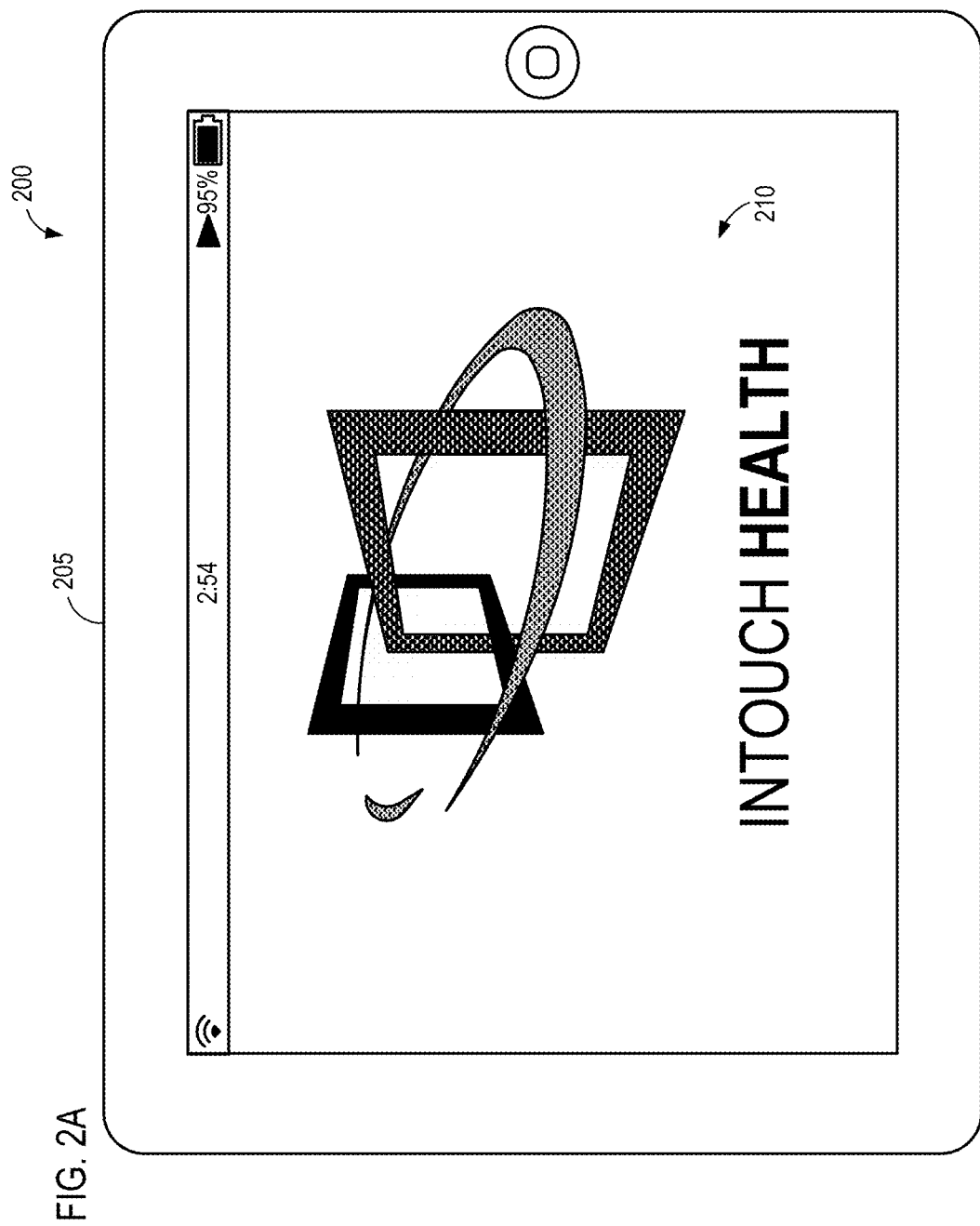
FIG. 2A illustrates an embodiment of an initial launch page for an RPI or other application associated with a telepresence device.

FIG. 2A illustrates an embodiment 200 of an initial launch page 210 for an RPI or other application associated with a telepresence device. As illustrated, a PED 205 may display the initial launch page 210 until the RPI fully loads. Alternative logos, graphics, informational displays and/or other content may be displayed. For example, a general greeting or specific greeting may be displayed on/during launch. In some embodiments an icon or object may indicate the progress or timeframe until loading is complete. In some embodiments, a cancel button or settings configuration may be available within the initial launch page 210.

FIG. 2B illustrates embodiment 250 of an alternative initial launch page 270 including an image of a telepresence device 275. The launch page 270 may be oriented such that it induces or encourages a user to align the PED 255 such that camera 280 is oriented in about the middle of a user's face and at or above an eye level of a user's face. In the illustrated embodiment, if a user had been holding the PED 255 in a landscape orientation, the image of the telepresence device 275 in the portrait orientation may encourage the user to rotate the PED 255 to the portrait orientation with the camera 280 in the top middle. An information bar 260 may provide information such as battery power, time, and/or connection strength. The initial launch page 270 may be unique to each PED on which it is utilized. For example, the RPI may detect that a PED with a camera positioned for a landscape orientation is being used and reorient the displayed launch page 270 accordingly.

Figure 2C:
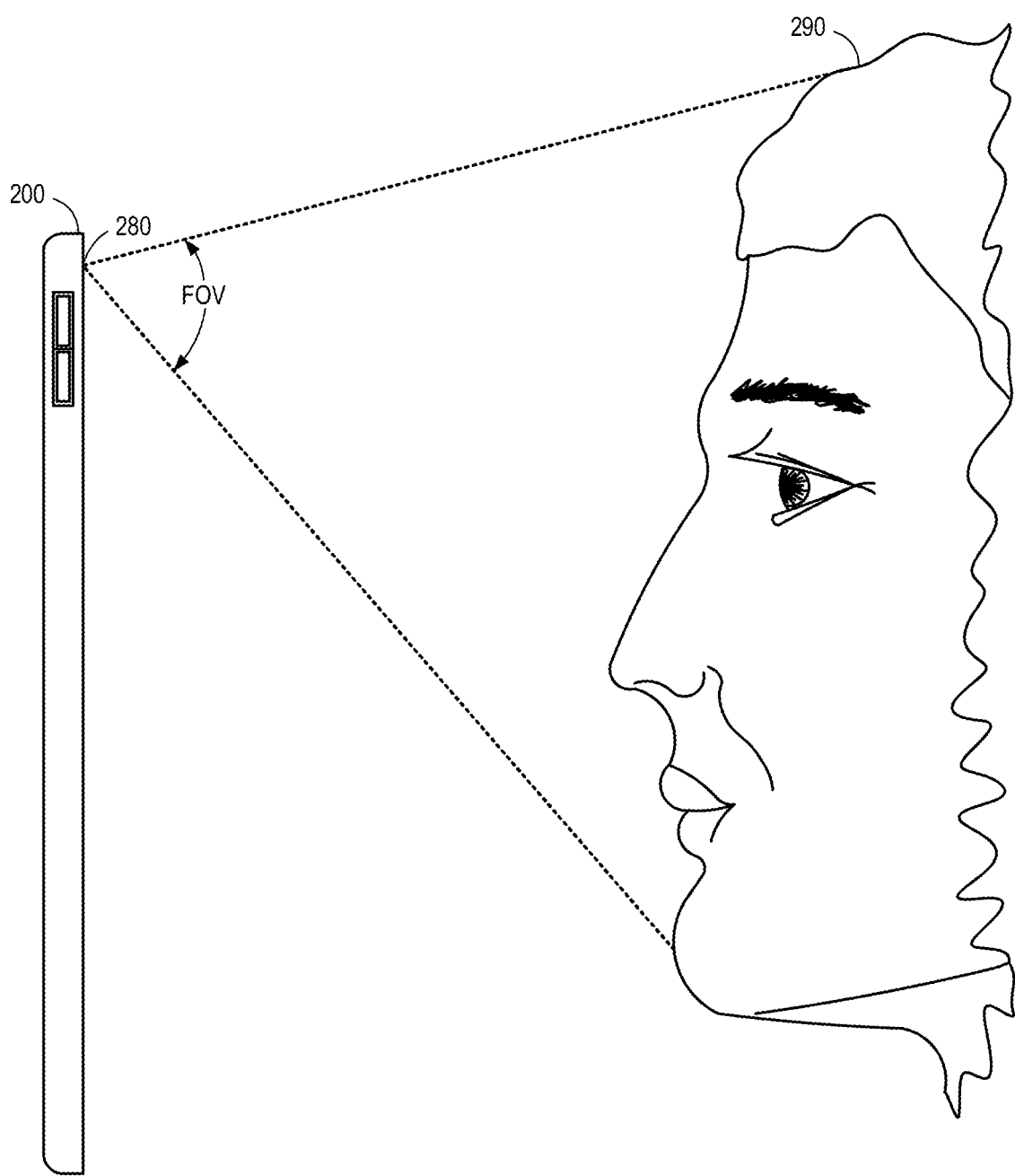
FIG. 2C illustrates a front-facing camera located near the top of a PED in a portrait orientation capturing an image of a healthcare practitioner.

FIG. 2C illustrates a front-facing camera 280 of the PED 200. The camera 280 is illustrated as located on the top of the PED 200 for capturing an capturing an image of a healthcare practitioner just above eye level in a portrait orientation. This location of the camera 280 relative to the face of a healthcare practitioner 290 may facilitate the capture of an aesthetically pleasing image of the healthcare practitioner 290 for display on a screen of a telepresence device. Accordingly, a patient or other person viewing the screen on the telepresence device may view a natural image of the healthcare practitioner 290 using the RPI on the PED 200, rather than an un-aesthetically pleasing perspective of the healthcare practitioner 290. For example, a side-captured or bottom-captured image of a healthcare practitioner 290 may not be aesthetically pleasing.

According to various embodiments, the RPI may automatically adjust the field of view (FOV) of the camera 280. In some embodiments, the healthcare practitioner 290, or other user, may manually adjust the field of view of the camera 280. Additionally, any number of compositional and exposure variables of the camera may be automatically or manually adjusted/adjustable. The RPI or the healthcare practitioner 290 may automatically or manually select which camera to use in the event a PED has multiple cameras. A user may, in some embodiments, select which camera is used during a session.

Figure 3A:
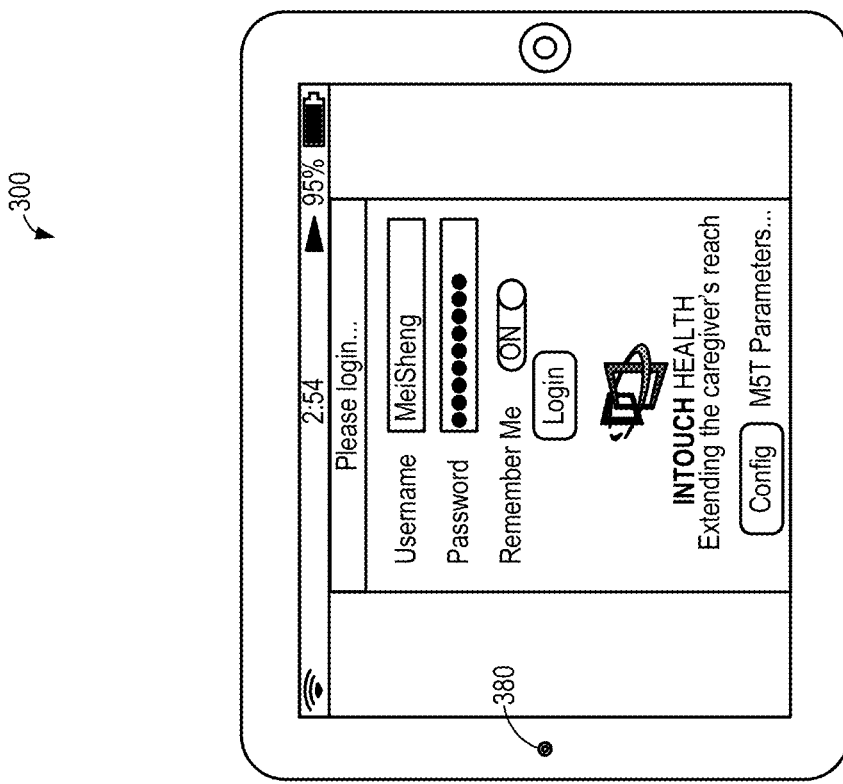
FIGS. 3A and 3B illustrate embodiments of a login page for the RPI.
Figure 3B:
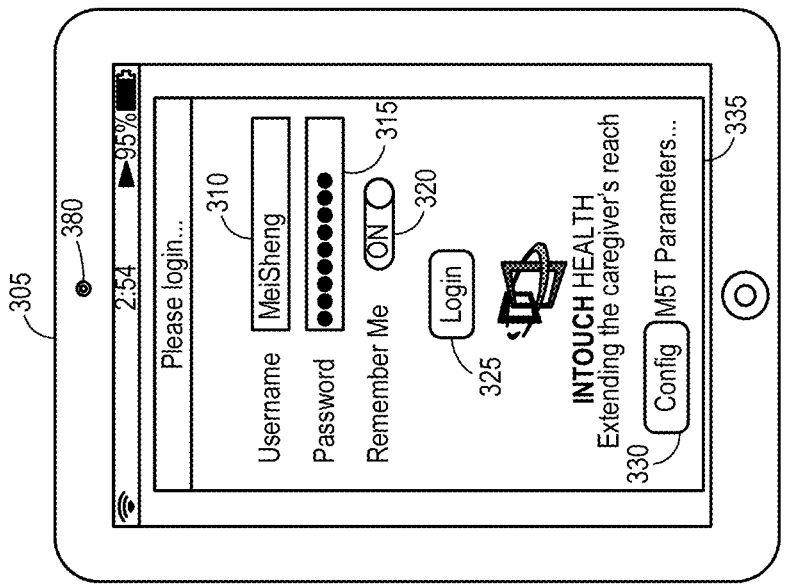

FIGS. 3A and 3B illustrate embodiments of a login page 325 on a PED 305 for accessing a telepresence device or telepresence network via an RPI, respectively. Any of a wide variety of login credentials 310 and 315 and/or security technologies may be employed. In some embodiments, a username, handle, and/or password may be provided on a different settings page. In some embodiments, the username, handle, and/or password may be maintained in a configuration file. The login page may include a button 330 or link that opens a settings or configuration page. Accordingly, a "remember me" 320 option may be provided to a user.

Figure 4:
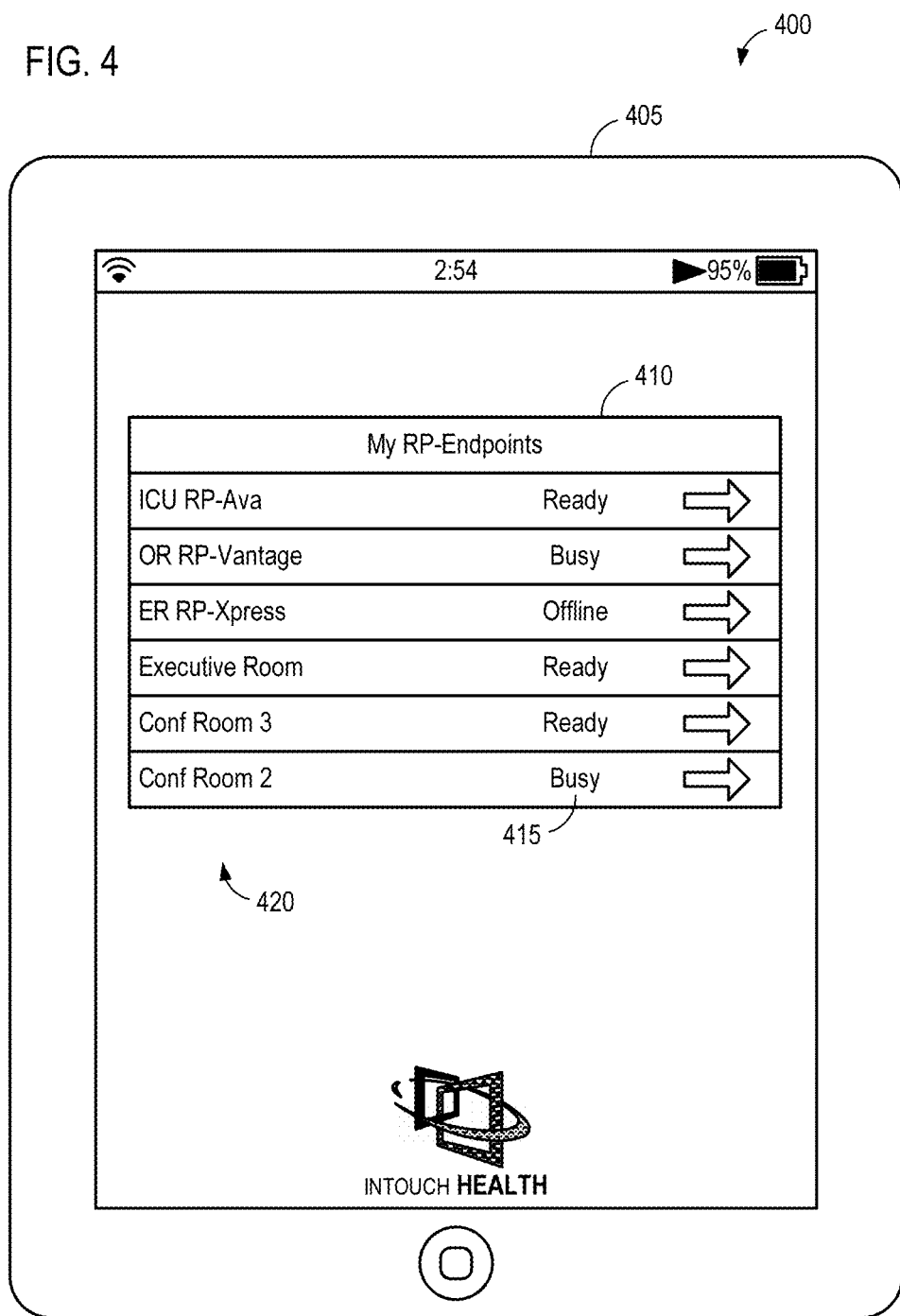
FIG. 4 illustrates an embodiment of an endpoint list of various telepresence devices and their connectivity state.

FIG. 4 illustrates an embodiment 400 of an endpoint list 410 generated by the RPI running on the PED 405. The endpoint list 410 may include various telepresence devices 420 and their respective connectivity states 415. A user may indicate (via a touch, a click, using a stylus, and/or by speaking) to which of the available endpoints he or she would like to connect. Where an ADT (Admissions, Discharges, and Transfers) data source is available, patients may also be listed. Selecting a particular patient may initiate a connection to an endpoint device (telemedicine device) that is assigned to, associated with, and/or in proximity to the selected patient. A telemedicine device in proximity to the patient could be a telemedicine device nearest a location of the selected patient, the same bed, room, or floor number. Where multiple autonomous or semi-autonomous endpoint devices (telemedicine devices) are present and capable of navigating to the selected patient, the RPI may automatically determine an optimal endpoint device to dispatch to the patient.

Factors involved in determining the optimal endpoint device could be distance or estimated travel time to the selected patient or remaining battery life of respective telepresence devices. Additionally, the RPI may dispatch the endpoint device that can reach the selected patient while minimizing travel through areas with poor wireless connectivity, confined spaces/areas, high-traffic areas, sensitive and/or secure areas, dangerous areas, and/or otherwise undesirable zones.

The endpoint list may also include doctors, nurses, staff, or any other persons that may currently (or for a scheduled period of time) be associated with a particular location and/or patient to which the endpoint can navigate. The endpoint list may be searchable and/or filterable. In some embodiments, the endpoint list may be implemented with a text box, in a window, or in separate tabs. As the user enters alphanumeric characters into the text box, the list may be instantaneously filtered to exclude endpoints whose names do not match the character string currently contained in the text box.

Other filtering parameters may be specified, such as endpoint type, manufacturer, status, facility, building, floor, room, customer, and/or any other grouping. Logical, arbitrary, or otherwise customized groupings of endpoints may be created by a user or administrator, and these groupings may additionally be used to filter or otherwise search the list of endpoints. In some embodiments, each endpoint in the list may have an associated status indicator, which informs the user whether a device is ready, busy, offline, in a private session, and/or in a multi-presence session (which the user may join to receive session audio, video, images, or potentially control the some or all functions of the endpoint).

Figure 5:
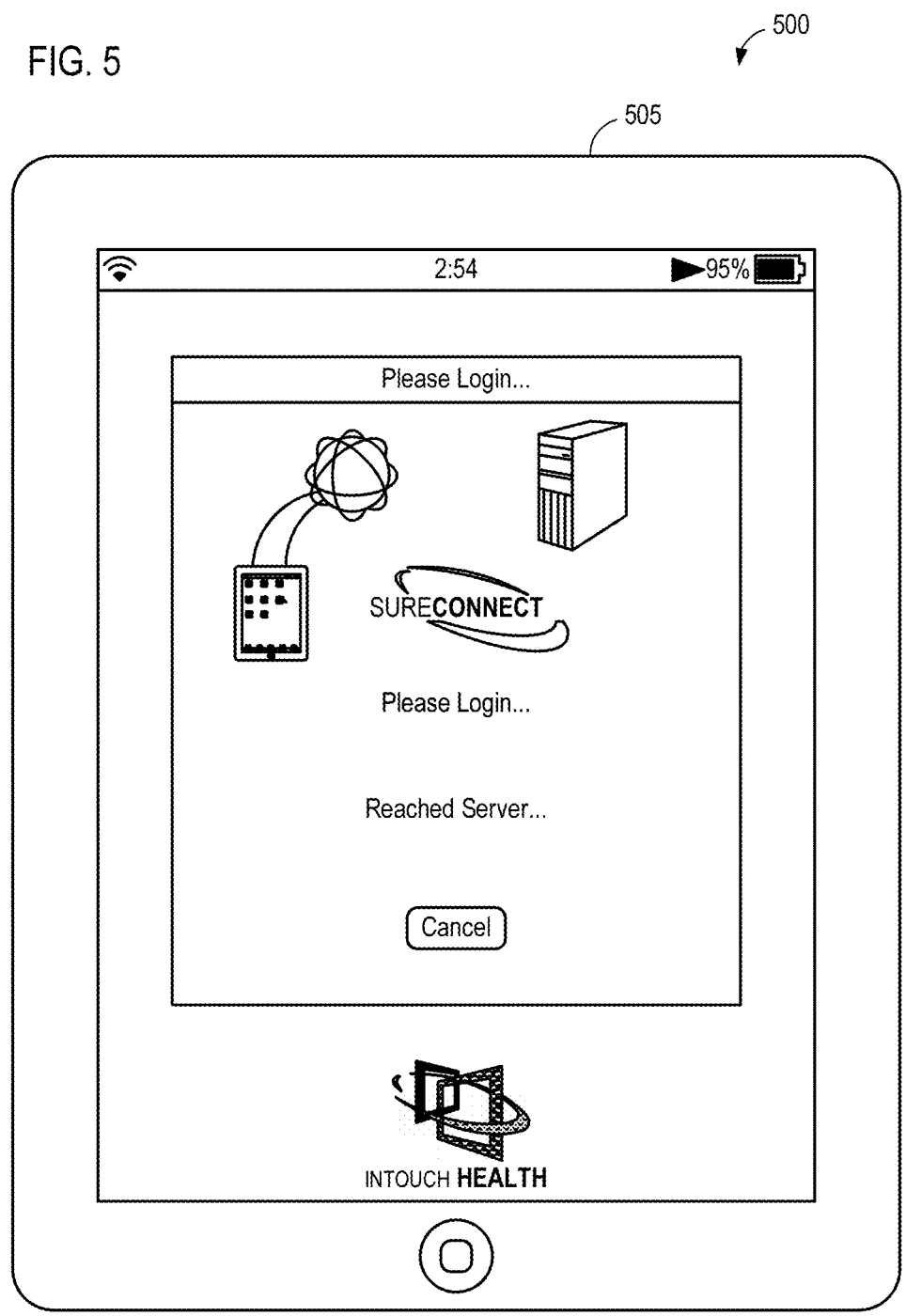
FIG. 5 illustrates a connection wizard configured to facilitate the connection of a user to a telepresence network.

FIG. 5 illustrates an embodiment 500 of a PED 505 displaying a connection wizard page as a user is connected to a telepresence network and/or telepresence device. The connection wizard may facilitate the connection of a user to a telepresence network, a specific telepresence device, and/or other operators of RPIs. In various embodiments, the displayed connection wizard page may be purely a placeholder image displayed while a connection is established. In other embodiments, the connection wizard may enable or allow a user to select various connection parameters and/or settings.

Figure 6:
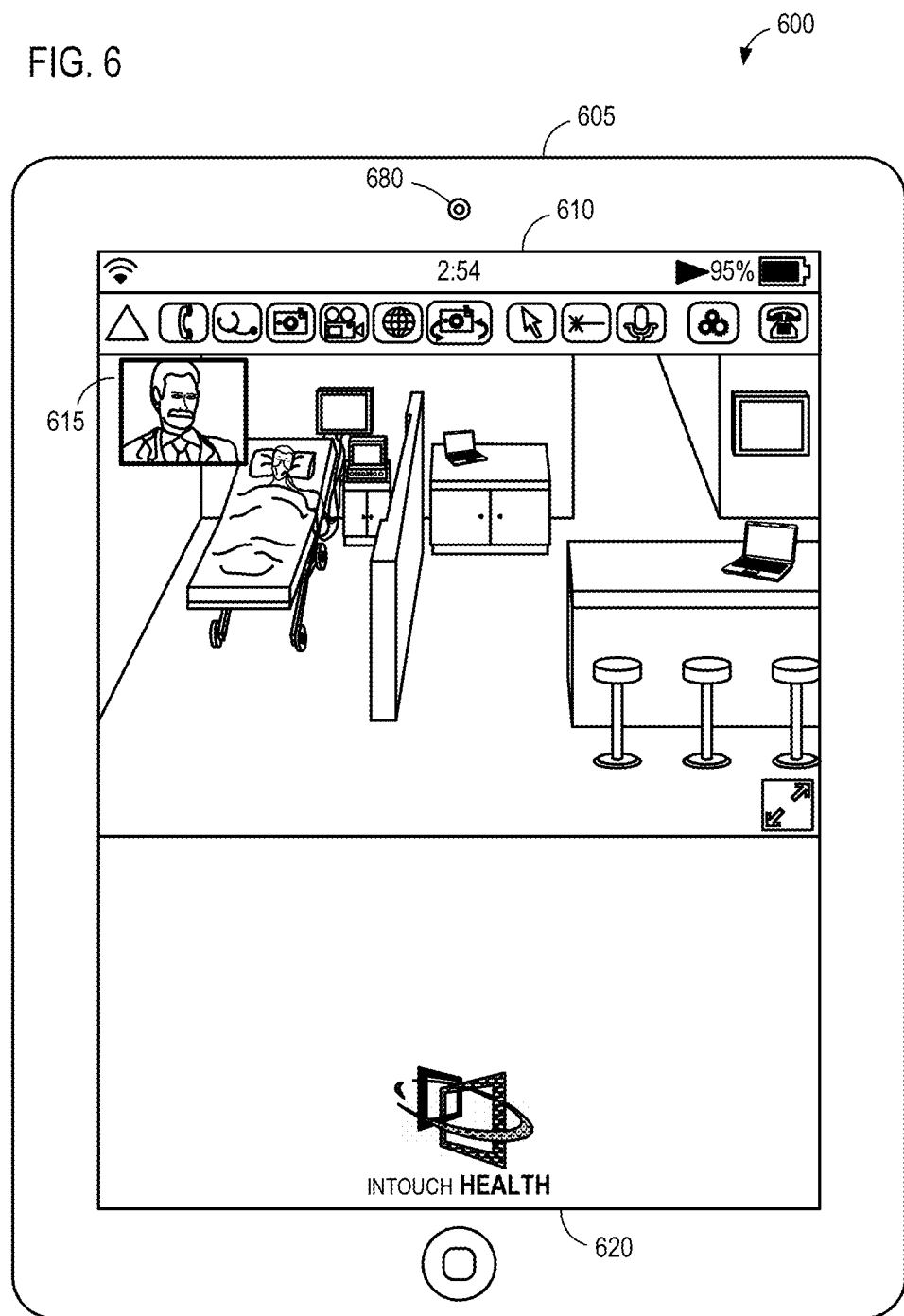
FIG. 6 illustrates an exemplary embodiment of a module within the RPI configured to provide visual and interactive control of a telepresence device.

FIG. 6 illustrates an exemplary embodiment 600 of a module within the RPI configured to provide visual and interactive control of a telepresence device. As illustrated, the RPI may be divided into an upper panel 610 and a lower panel 620. The upper panel 610 may include a video window 615 showing the user of the PED 605 what the camera 680 is capturing. The upper panel 610 may display a video feed originating from a camera on the remote telepresence device. The upper panel 610 may further include various informational items and/or control panels, described in greater detail in conjunction with subsequent figures. The lower panel 620 may be used to display additional information and/or to receive inputs from a user of the PED.

Figure 7:
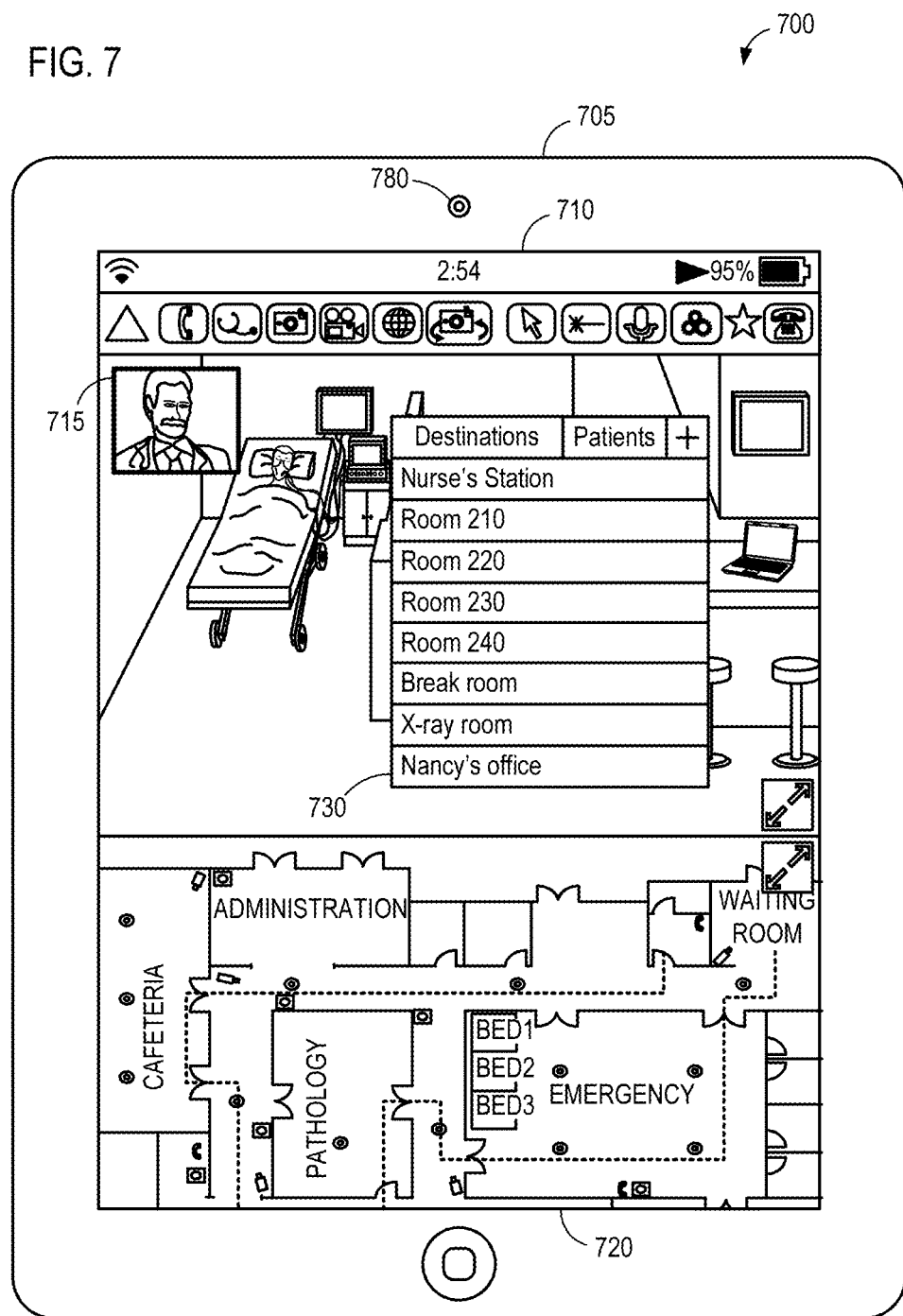
FIG. 7 illustrates an embodiment of a map and navigation module of the RPI.

FIG. 7 illustrates an embodiment 700 of an RPI on a PED 705 including a map 720 and a navigation module 710. The map 720 may display a plan view map of a healthcare facility. An image captured by the camera 780 may be displayed in a window 715. A list of destinations 730 may be displayed in an upper panel. According to various embodiments, a user may select a destination by selecting a room within the healthcare facility, or by selecting a patient within a patient tab. The selection of a room may be considered a navigation input. The selection may then be translated into one or more navigation instructions to guide the telepresence robot, autonomously or semi-autonomously to the selected location.

Once a destination, patient, or other person is selected, the RPI may communicate the desired destination to the telepresence device via navigation instructions. The navigation instructions may allow for the telepresence device to be manually navigated, semi-autonomously navigated, or autonomously navigated to the desired destination. Systems and methods for manual, semi-autonomous, and autonomous navigation are described in U.S. patent application Ser. No. 13/360,579, previously incorporated by reference.

Figure 8:
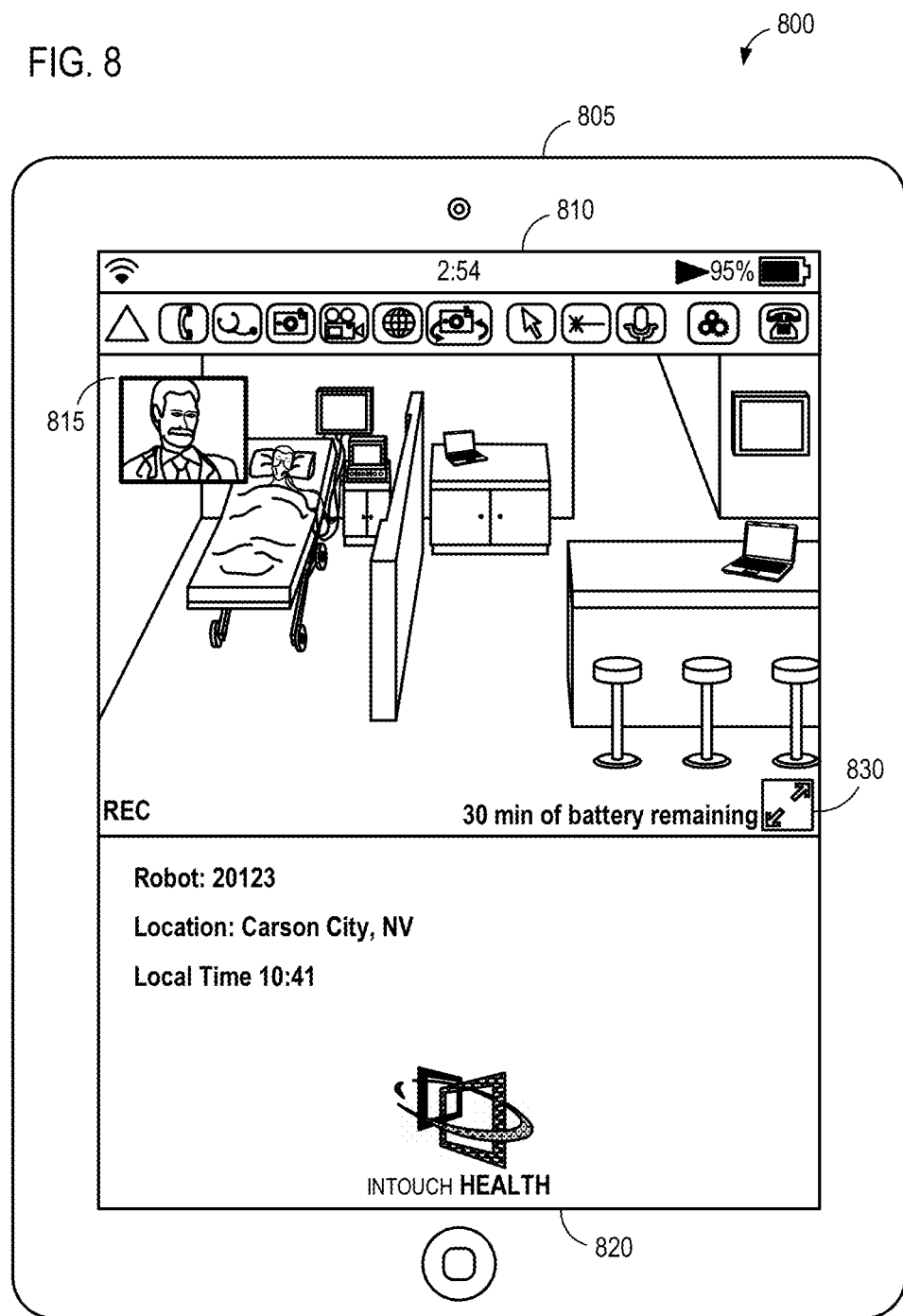
FIG. 8 illustrates an example of a notification that may be displayed to a user via the RPI.

FIG. 8 illustrates an embodiment 800 of a notification 820 generated or received by the RPI. The notification 820 may be displayed on a PED 805 in a lower panel or an upper panel. As illustrated, the notification 820 may include the remaining battery life of the telepresence robot, the robot number, the location of the robot, and/or the local time. As in previous embodiments, a window 815 may show the image currently being captured by a camera. An upper panel 810 may be maximized, or shown in a full-screen mode, by selecting a full-screen icon 830. In some embodiments, the notifications 820 may be displayed as overlays when the upper panel 810 is maximized or is in a full-screen mode.

The RPI may be designed to provide a user with notifications regarding various states of a device (e.g., the PED 805 or the telepresence device), a connection, or a session. For instance, the RPI may display indications of whether video or audio recording is active and/or enabled or if a laser pointer or remote pointer is active, a battery level or remaining time available based on the current battery level, related to network performance, and/or a wireless signal strength.

In one embodiment, the RPI may provide a message to the user (who may be moving around) if the PED loses (or detects a decrease in strength of) a communication signal (e.g., a WiFi or 4G signal) as the result of the user's movement and/or as a result of the telepresence device leaving a good WiFi zone, or some loss, outage, or failure elsewhere in the link. The message provided to the user may distinguish whether the loss, outage, or drop in strength has occurred locally, remotely, or elsewhere in the link.

In some embodiments, the RPI may be configured to provide notifications or alerts using various display modifications, annotations, or overlays. For example, the screen may pulsate with a partially translucent overlay to indicate that a battery of the telepresence device is dying and/or that connectivity is below a predetermined level. For example, the screen may pulsate with a red glow, possible with a vignette such that it is increasingly translucent toward the center of the display, to indicate that a battery is dying.

In one embodiment, a notification may include one or more pop-up dialogue boxes to bring critical information to the attention of the user of the RPI. For example, if the connectivity falls below a level considered clinically viable, the RPI may request that a user of the RPI acknowledge the current limitation in order to continue the telepresence session. As another example, the RPI may request that a user acknowledge anomalous conditions associated with the RPI, the patient, and/or the telepresence device. The RPI may request that a user acknowledge that they are aware of or have noticed patient conditions considered outside of predetermined ranges. For example, the telepresence device and/or the RPI may recognize that a patient's heart rate is below a threshold level and request that a remote user of the RPI acknowledge awareness of the condition.

Figure 9:
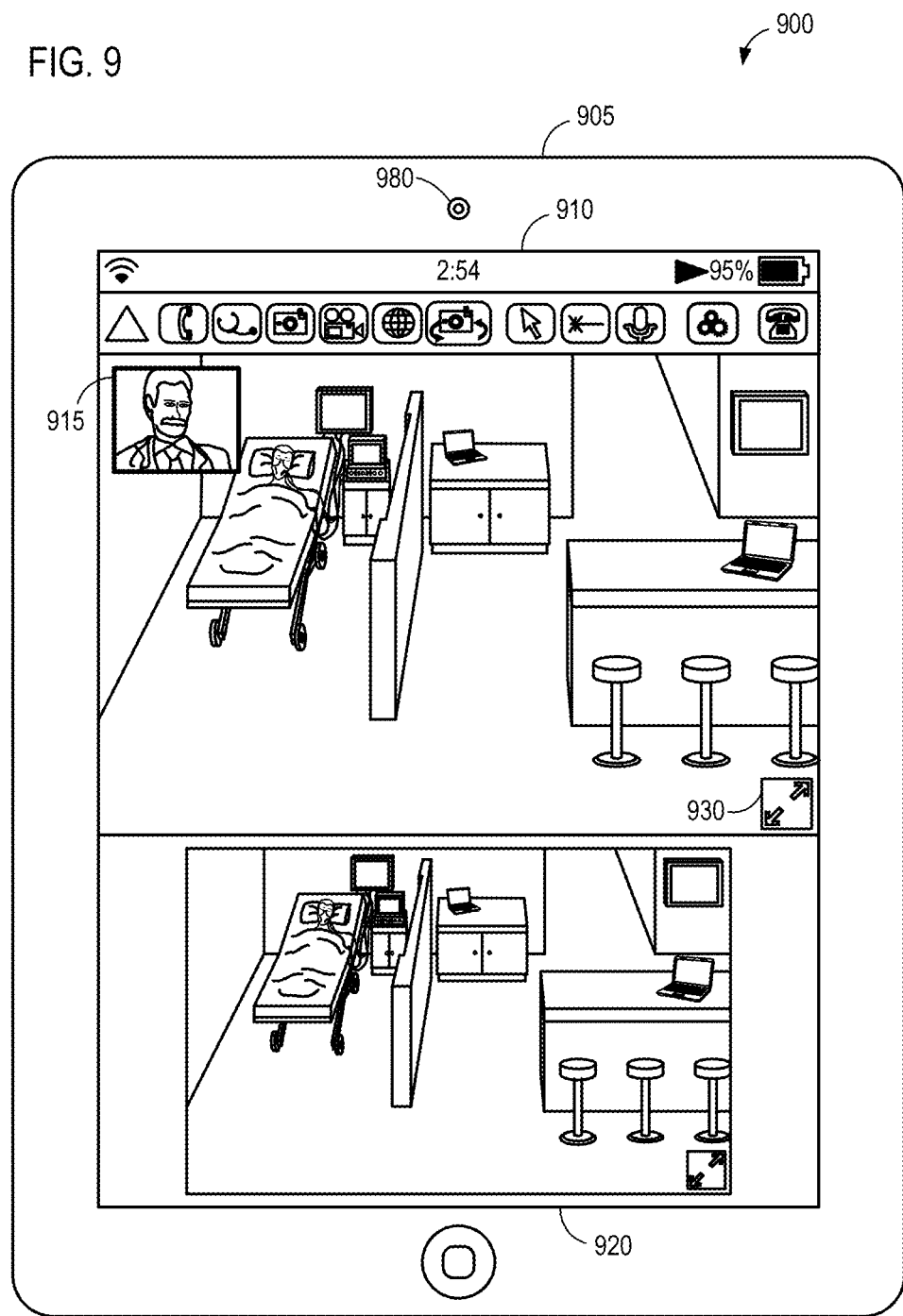
FIG. 9 illustrates an embodiment of a media manager module of the RPI configured to allow a user to capture and manage audiovisual media from the telepresence device.

FIG. 9 illustrates an embodiment 900 of a media manager module 920 of the RPI configured to allow a user to capture and manage audio and/or visual media from the telepresence device. As illustrated, the upper panel 910 of the PED 905 may include a live video feed from the telepresence device. The live video feed in the upper panel 910 may be expanded to full-screen via the full-screen icon 930. The lower panel may include a media manager module 920 adapted to capture still images, audio, video, and/or a combination thereof from the telepresence device. Additionally, the media manager module 920 may allow for editing, playback, trimming, storing, emailing, and/or other functions.

For example, when a user taps the video or movie projector icon in a toolbar, the RPI may display the native video controls of the PED overlaid above the live video feed, along a toolbar across the upper panel 910 or a lower panel, or elsewhere on the screen. Additionally, a library of network-accessible or locally stored video clips or movies may be made accessible in the lower panel. The user may navigate the video clip library by swiping left or right, which may cause successive clips to be visually cycled from completely obscured to partially obscured to fully visible (and selectable/playable), to partially obscured again, and so on. Once the user locates a desired video, the user may drag and drop the video from the media manager module to the upper panel 910 to cause the video to be displayed on a screen on the telepresence device.

The RPI may enable playback to be controlled from the PED and/or the telepresence device. Once a video is selected, the RPI may enable the user to navigate or skip through an index of key frames contained in the video. The RPI may additionally enable the user to delete a video using a flicking gesture. For security and privacy, videos may be stored in an encrypted format. In another example, when the user taps the camera icon in a toolbar, the interface may display a cover-flow image library in the lower pane. Images may be searched, browsed, displayed on the PED, or displayed at the remote endpoint in the same manner as described above with respect to video files in the media manager.

Figure 10:
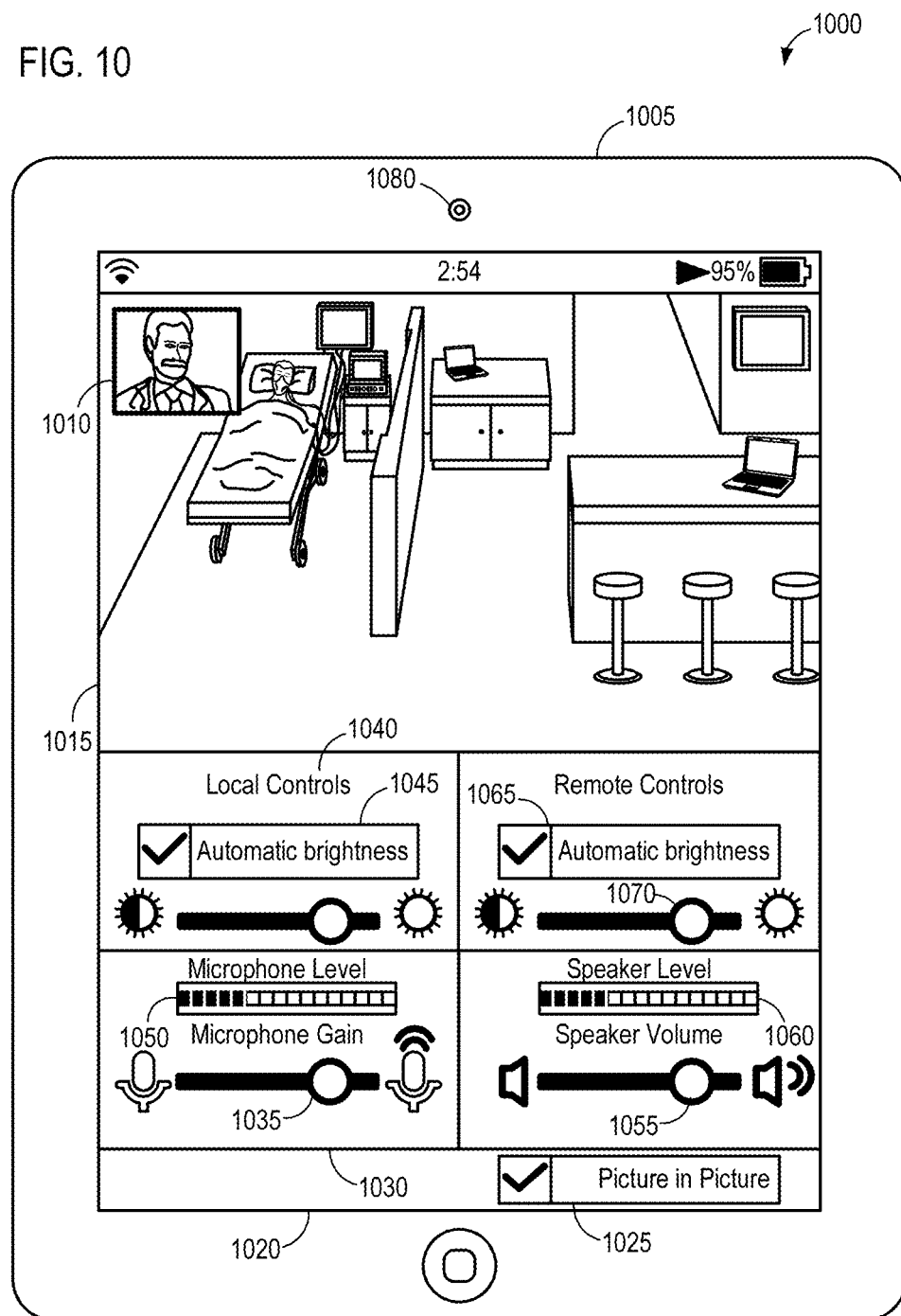
FIG. 10 illustrates an embodiment of menu of the RPI allowing a user to modify various settings on the local PED and/or the remote telepresence device.

FIG. 10 illustrates an embodiment 1000 of menu 1040 of the RPI allowing a user to modify various settings on the local PED 1005 and/or a remote telepresence device. As illustrated, a window 1010 may show the user what is currently being captured by the camera 1080. The upper panel 1015 may display a live video feed generated by the telepresence device. The menu 1040 in the lower panel 1030 may contain settings for local brightness control 1045, remote brightness control 1065, microphone levels 1035, speaker levels 1055, and/or any of a wide variety of other features.

A lower bar 1020 may also include one or more management tools. As illustrated, a picture-in-picture selection may allow a user to selectively disable the picture-in-picture window 1010. An auto-brightness feature 1045 may be enabled via a checkbox. The control settings may further include a microphone level meter 1050 to indicate a volume or sound pressure level relative to a maximum specified input or clipping level. Additionally, the settings control may include a microphone gain slider 1035 to allow adjustment of a microphone gain to a desired level. Similarly, a speaker level meter 1060 may graphically illustrate the current volume or sound pressure level relative to a maximum specified output or slipping level. The remote controls may include a picture-in-picture checkbox to enable the user to toggle a picture-in-picture display of the remote video view at the remote endpoint.

Figure 11:
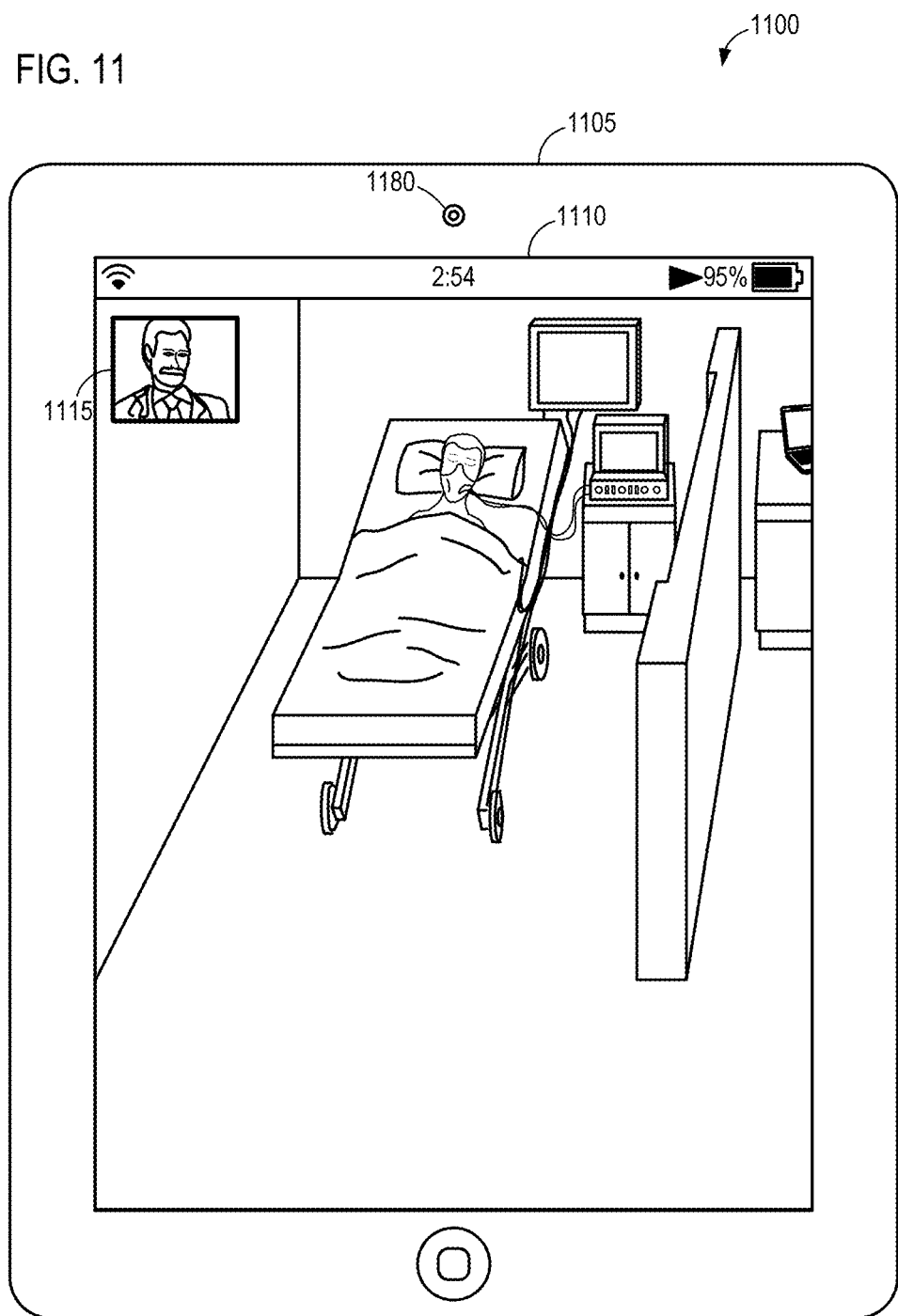
FIG. 11 illustrates an embodiment of the RPI in full-screen video mode.

FIG. 11 illustrates an embodiment 1100 of the RPI in full-screen video mode. As illustrated, a window 1115 may show a picture-in-picture of the image captured by camera 1180. The upper panel 1110 may display a full-screen live video feed captured by a telepresence device.

Figure 12:
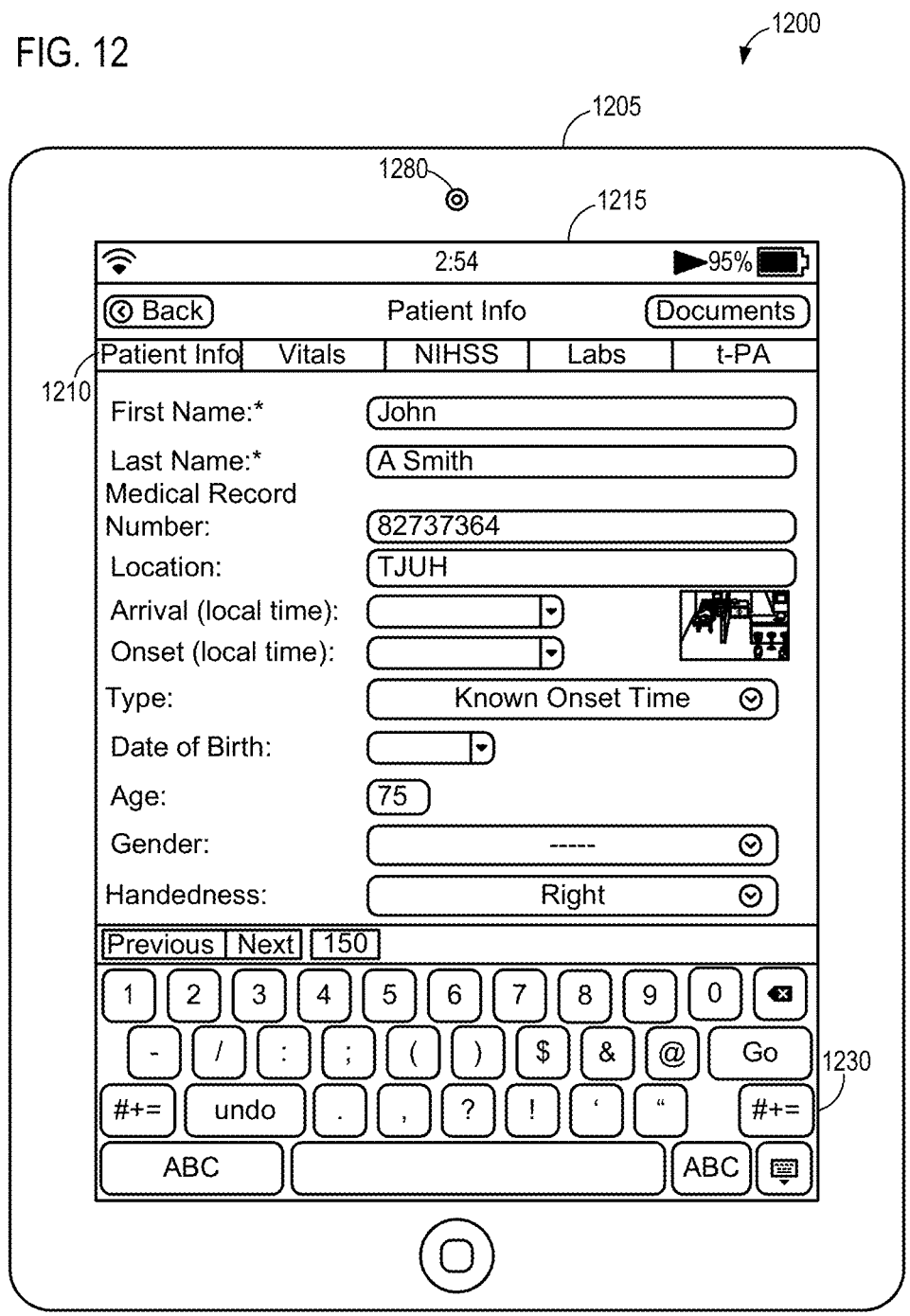
FIG. 12 illustrates an embodiment of the RPI in full-screen data mode.

FIG. 12 illustrates an embodiment 1200 of the RPI in full-screen data mode. In the illustrated embodiment, the image captured by camera 1280 may not be displayed in a picture-in-picture window to make more room for data entry and/or visualization. In some embodiments, the image captured displayed by the telepresence device that is normally the image captured by the camera 1280 may display a no signal or screensaver image, or a previous image of the healthcare practitioner may be "frozen" on the screen.

The PED 1205 may allow data to be entered via the touch screen using keyboard 1230. As illustrated, the RPI may display a single data panel 1215 in a full-screen mode by removing the upper panel typically used to display the live video feed from the telepresence device. Various tabs 1210 may toggle the screen between various data input and/or visualization modes. In some embodiments, the remote video view may continue to be displayed in a small window or panel.

Figure 13:
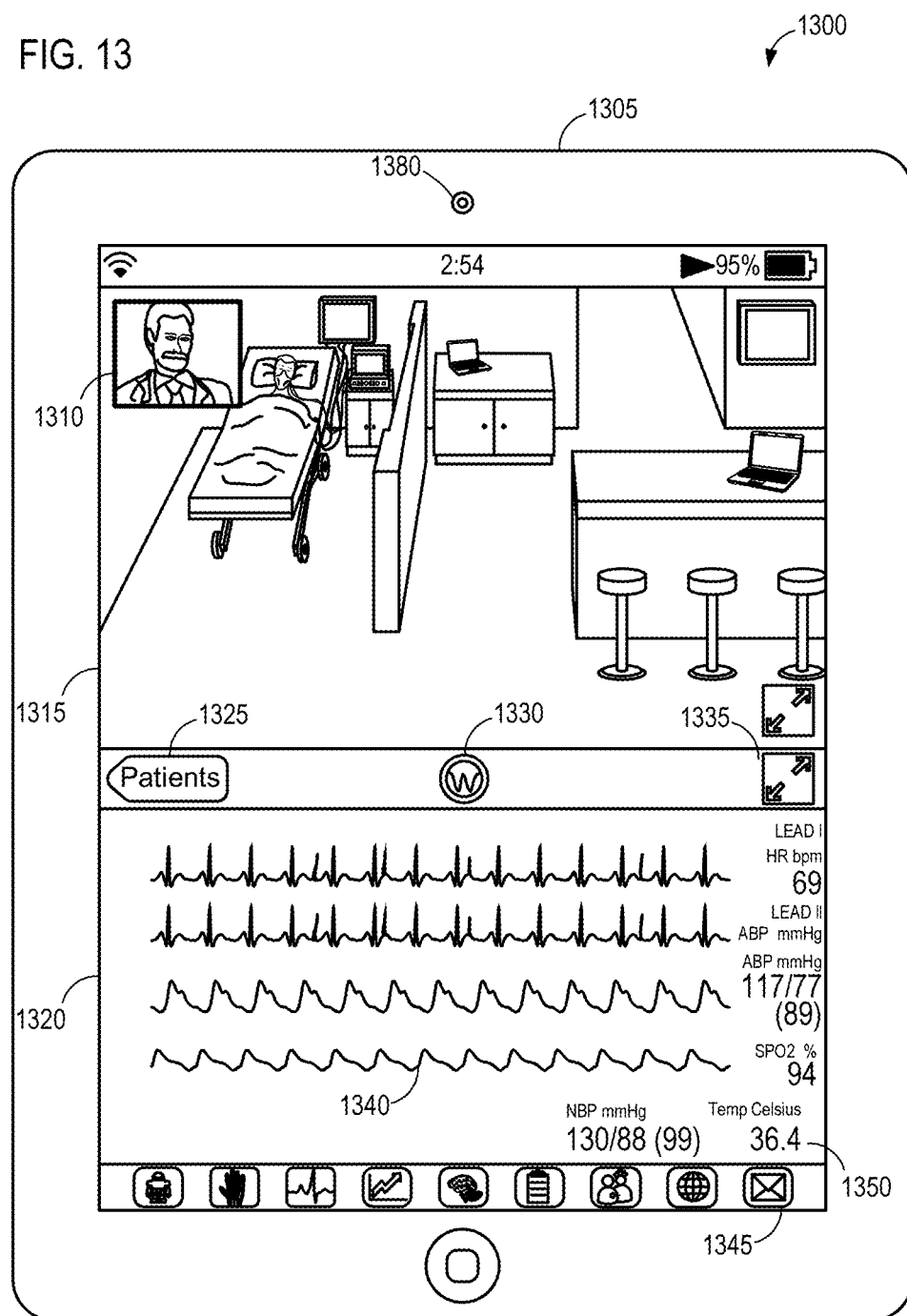
FIG. 13 illustrates an embodiment of the RPI including a visual representation of patient telemetry data.

FIG. 13 illustrates an embodiment 1300 of the RPI including a visual representation of patient telemetry data 1350 displayed in a lower panel 1320. The PED 1305 may again include a camera 1380 and a window 1310 may be displayed by the RPI to show a user what is currently being captured by the camera 1380. As illustrated, full-screen icons 1335 may be available in the RPI to transition either of the lower panel 1320 or the upper panel 1315 to a full-screen mode. A software button 1330 may allow the telemetry data to be toggled, changed, scrolled, and/or otherwise manipulated. A patient icon 1325 may allow a user to select a telepresence device and/or telemetry data associated with a different patient. The telemetry data 1350 may be displayed as numerical values and/or in graphical form 1340.

FIGS. 14A-C illustrate exemplary embodiments of a telepresence device. As illustrated in each of FIGS. 14A-C, a telepresence device may comprise a base 1410 capable of being manually driven, semi-autonomously driven, and/or autonomously driven. Various display features, connection features, and/or data ports 1420, 1430, and 1465 may be available on a mid-section of the telepresence device. The telepresence device may also include a handle 1435. A head portion 1440 of the telepresence device may include one or more cameras 1460, speakers, and/or microphones. In addition, the head portion 1440 may include one or more two- or three-dimensional depth sensors, such as LADARs, LIDARs, or structured light projectors/scanners. Multiple cameras 1460 may be useful to render 3D images, and multiple microphones and/or speakers may be useful for rendering and/or generating directional sound. The head portion may also include a display 1450 configured to display, for example, an image captured using an RPI on a PED.

The display 1450 and/or the interface 1430 may comprise a touch screen or other interface to receive inputs. In some embodiments, if a telepresence device is an autonomous mobile telepresence device, the display 1450 and/or the interface 1430 may provide a list of destinations, healthcare practitioners, and/or patients to which, as described herein, the telepresence device can be sent or connected. The display 1450 and/or the interface 1430 may also enable a person to stop the telepresence device when it is autonomously navigating and, likewise, enable the telepresence device to resume autonomous navigation to its destination. The display 1450 and/or the interface 1430 may additionally have a button or menu option that instructs the telepresence device to autonomously navigate to an out of the way location (e.g., a wall, corner, etc.), a dock, a storage location, and/or a charging station. The display 1450 and/or the interface 1430 may include buttons or menu options for various settings or to page or notify support personnel of a problem with or question regarding the operation of the telepresence device.

Figure 15:
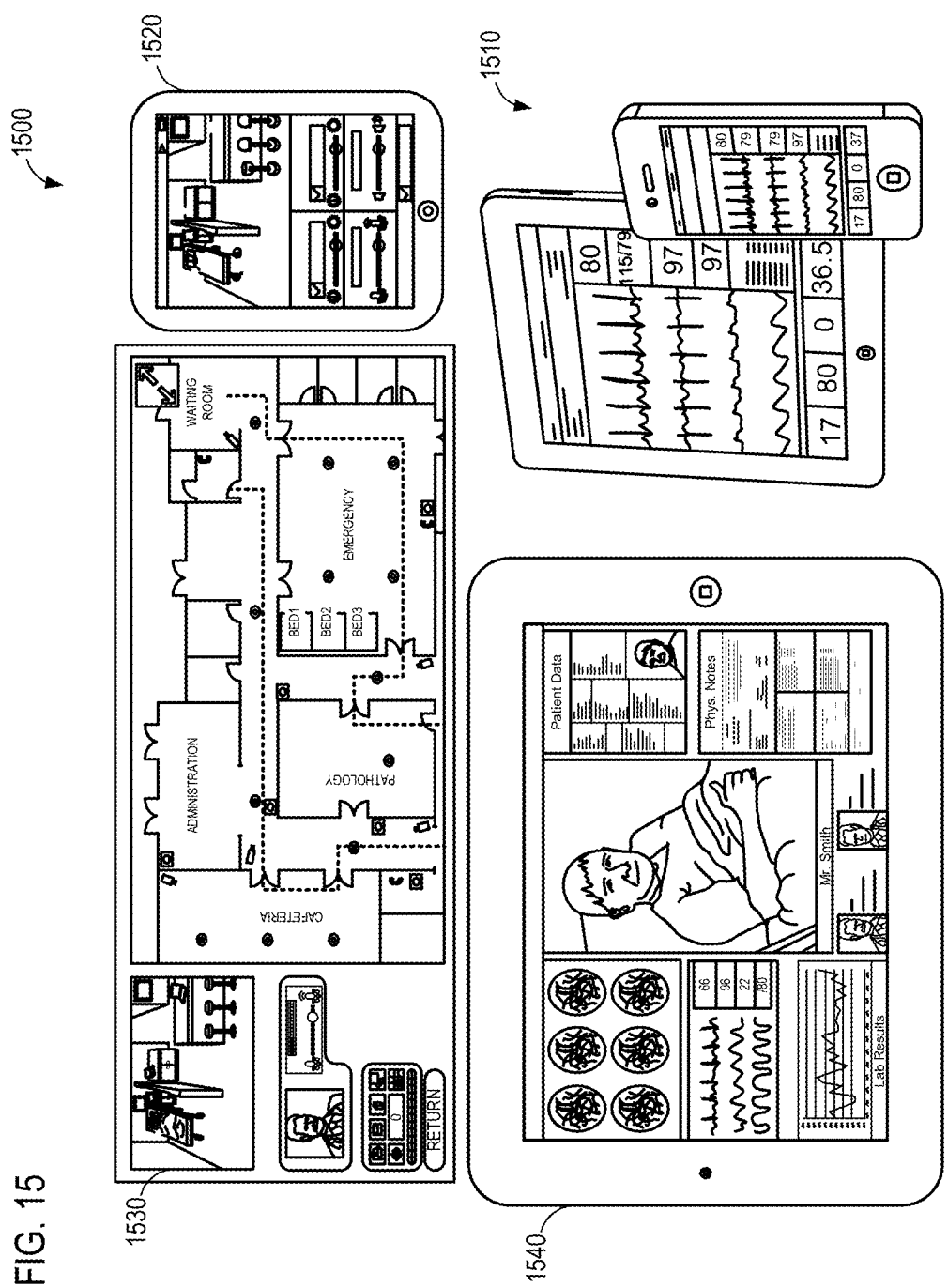
FIG. 15 illustrates an RPI configured to provide patient visualization, remote settings control, navigation control, and access to patient data integration.

FIG. 15 illustrates a panel 1530 including a plan map view, a video feed window, and various settings panels. The panel 1530 may be displayed in various forms and configurations via an RPI on a PED, such as the PEDs 1510, 1520, and 1540. Each of the PEDs 1510, 1520, and 1540 illustrate examples of panel arrangements generated by the RPI to maximize the useable screen space for various tasks performed using the RPI. It will be appreciated by one of skill in the art that a larger display may accommodate more panels or larger panels. Similarly, devices with multiple displays may accommodate one or more panels on each display. For example, a desktop version of the RPI may utilize multiple monitors connected to the desktop to display one or more panels.

Figure 16:
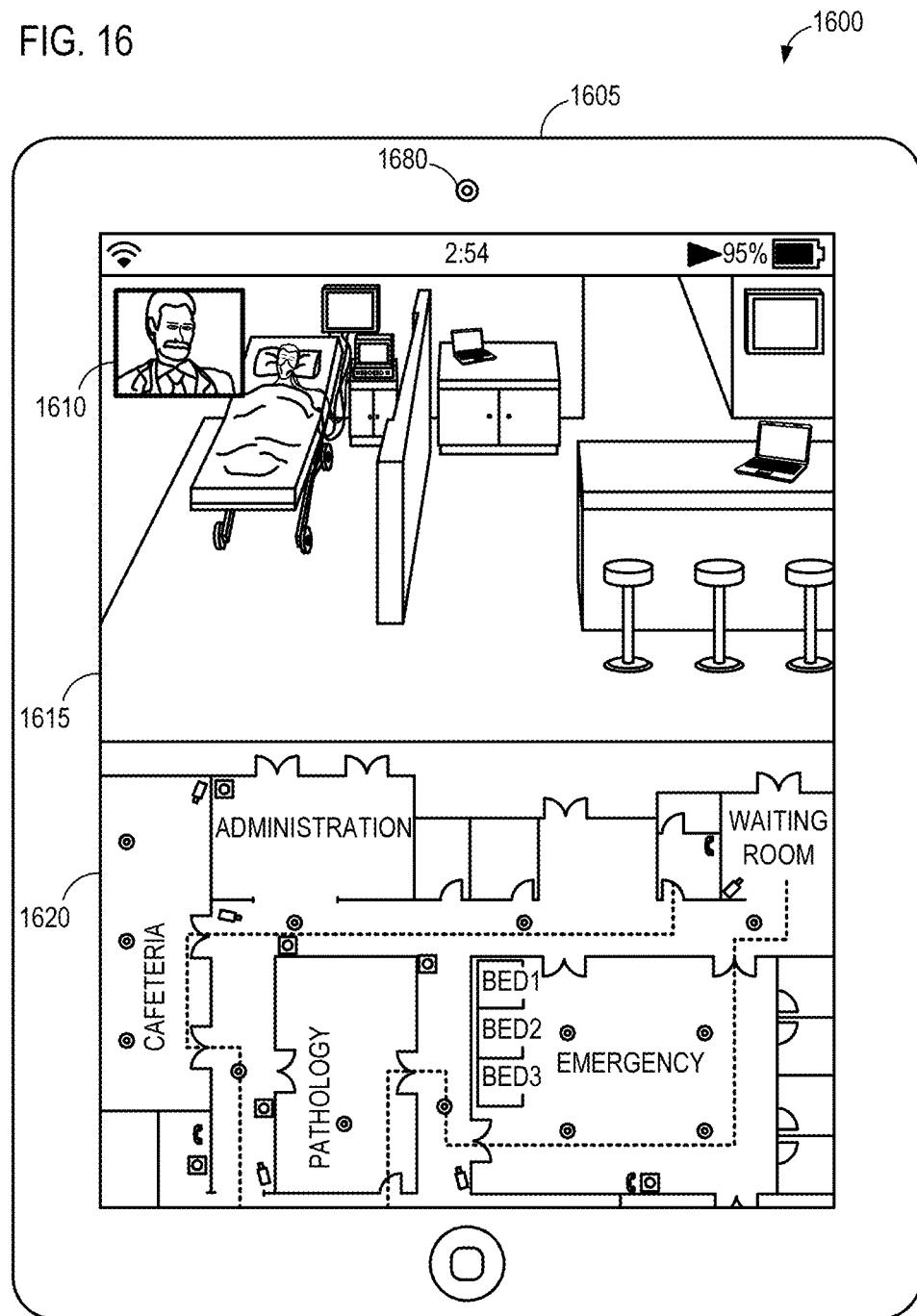
FIG. 16 illustrates a navigation module within the RPI configured to allow a user to navigate a telepresence device using one or more navigational techniques.

FIG. 16 illustrates an embodiment 1600 of an RPI on a PED 1605. The RPI may utilize the camera 1680 to transmit an image of the user to a telepresence device. The image captured by the camera 1680 may be displayed in a picture-in-picture window 1610. The upper panel 1615 of the RPI may display a live video feed received from the telepresence device. The lower panel 1620 may display a plan map view. In some embodiments, the plan map view may show a current location of the telepresence device within a healthcare facility (or other locale). The user may manually navigate the telepresence device using the live video feed and the plan view map. Alternatively or additionally, the user may select a location within the plan view map and the telepresence device may autonomously or semi-autonomously navigate to the selected location.

The input intended to direct the telepresence device to a new location may be considered a navigation input. For example, the selection of a room, patient, healthcare practitioner, location within a video feed, and/or other selection or input intended to cause the telepresence robot to navigate may be considered a navigation input. The navigation input may then be translated into one or more navigation instructions to guide the telepresence robot, autonomously or semi-autonomously, to the selected location.

Figure 17:
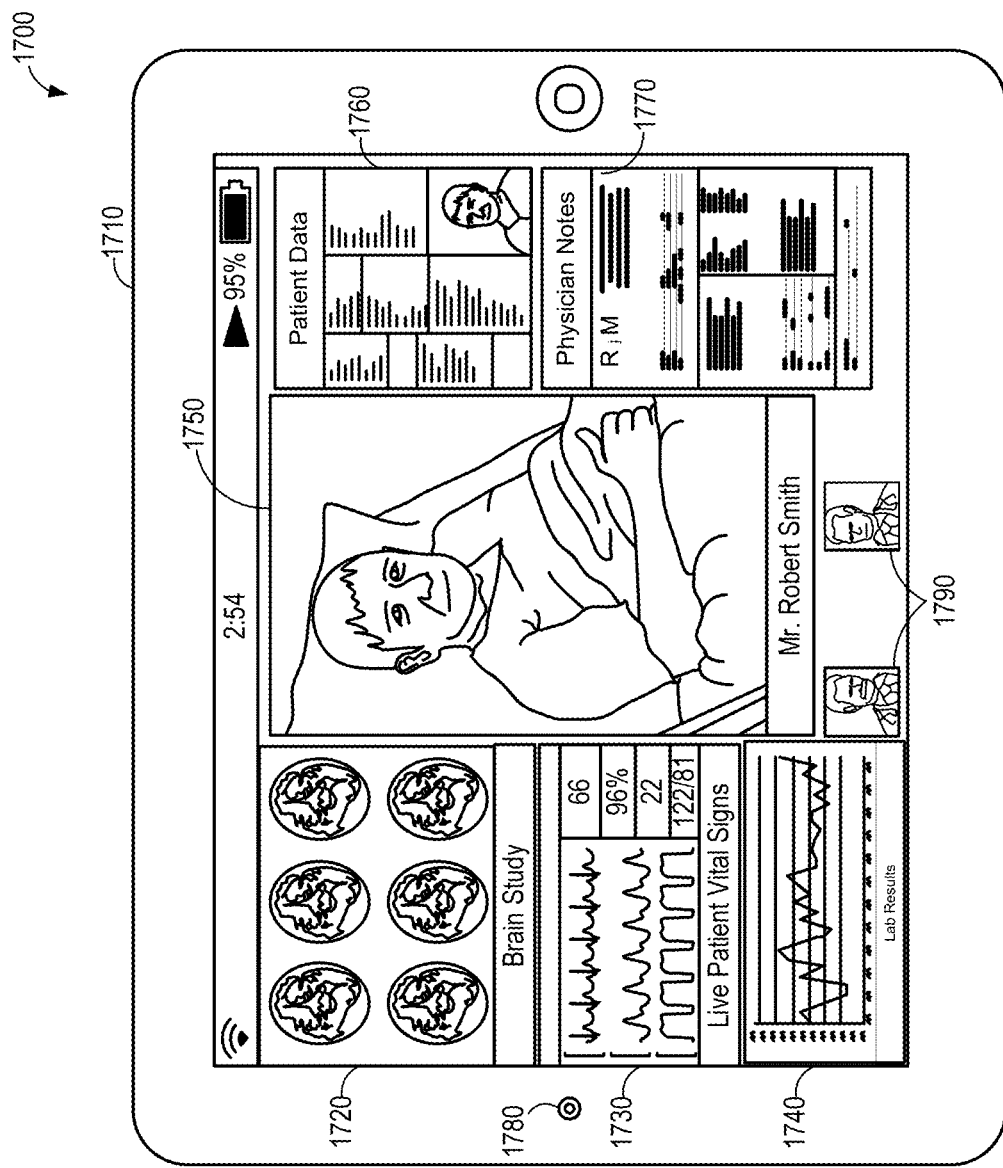
FIG. 17 illustrates the RPI displaying a video of a patient, associated telemetry data, and associated records.

FIG. 17 illustrates an embodiment 1700 of an RPI on a PED 1710 displaying multiple panels. As illustrated, a radiography panel 1720 may display images associated with a patient displayed in a live video feed 1750. Telemetry data 1730, lab results 1740, patient data 1760, and physician notes 1770 may be displayed in various other panels on the PED 1750 via the RPI. In a multi-user telepresence conference each of the participating users may be displayed in a panel 1790. According to various embodiments, each of the panels 1720, 1730, 1740, 1750, 1760, 1770, and 1790 may be moved, enlarged, merged with another panel, removed, and/or captured (recorded), intelligently based on decisions made by the RPI, based on usage history, based on relevancy, and/or based on user selection. A camera 1780 may be selectively enabled or disabled by the user.

The RPI may enable complete integration of patient data monitoring with the remote telepresence session, thereby adding a dimension of data-driven functionality uniquely valuable in telepresence applications. The user may select an icon from a toolbar or other panel to activate a patient bedside data monitoring app, such as those offered by any of a variety of real-time patient data monitoring application providers. Upon selecting the appropriate icon, a patient data monitoring window may appear in the RPI. The user may expand this pane to a full-screen view, reposition the pane, and/or resize the pane as described above. The RPI may show any number of real-time or archived patient biometrics or waveforms, such as temperature, heart rate, pulse, blood pressure, oxygen saturation, etc.

Using the touch-screen interface, the user may pause and resume real-time, time-delayed, or archived patient data. The user may move back and forth through time-based patient data using dragging or swiping gestures, or the user may zoom or scale the waveform or metric along an amplitude axis and/or time axis. The application may further allow the user to set markers along a waveform to measure variations in amplitude or time associated with various features of the patient data, such as peaks, valleys, maxima or minima (global or local), global averages, running averages, threshold crossings, or the like.

The data may be collected from bedside monitors or other monitoring devices in real-time and archived for a period of time (or indefinitely) in a server or database. The monitoring app may be a separate application and/or integrated within the RPI. The monitoring app may retrieve the relevant data and provide it to the RPI through an application programming interface (API) and/or the RPI may independently retrieve the data from a database.

The data may also be collected by the telepresence device by, for example, directing a camera of the telepresence device to the display of a monitoring device, and either recording video of the monitor display or performing image analysis on the video image to extract the patient data. The user and/or telepresence device may annotate the data and store the annotations with the data, either locally or in a remote server, for later retrieval. The monitoring app may enable alarms, alerts, notifications, or other actions or scripted activities set to take place in response to certain events in the data.

Further, the interface may integrate available ADT with patient bedside or biometric data. For example, if a patient's vitals or other biometrics trigger an alert or alarm condition, the telepresence device may be configured to autonomously navigate to the bed or room number of that patient, and send a notification or invitation to a doctor, caregiver, or specialist to begin a telepresence session with the patient. Additionally, when a healthcare practitioner initiates a session with a telepresence device and selects either a location, destination, or patient to visit with the autonomous telepresence device, the bedside or biometric data for a patient associated with the selected location, destination, or patient may be automatically retrieved and used to populate a "dashboard" of patient data that the healthcare practitioner can then review, annotate, or otherwise interact with as discussed above and depicted in FIG. 17.

Moreover, an autonomous mobile telepresence device may be used to conduct patient rounds in a healthcare facility. As the telepresence device moves from one location to the next, the location of the telepresence device may be used to retrieve the name and/or other data of a patient(s) associated with that location. For example, the telepresence device may retrieve patient biometrics, bedside data, electronic medical records, and/or other patient data to populate a patient dashboard on a display of the PED. In one embodiment, this information may be retrieved from a health level 7 (HL7) compliant server associated with the facility, healthcare practitioner, and/or patient.

In addition, an autonomous mobile telepresence device may be scripted or scheduled to make scheduled stops at various beds, rooms, locations, or patients. The RPI may retrieve the names or contact info of people (such as doctors, nurses, students, family members, etc.) associated with a scheduled or upcoming stop at a particular patient or location, and send a notification via SMS, email, etc., to the associated people inviting them to join the telepresence session by receiving audio and/or video from the session on a PED via the RPI.

To accommodate a time interval that may be necessary or convenient to allow others to join the session, the telepresence device may send invitations, notifications, and/or reminders to join the session a predetermined amount of time prior to the time the session is scheduled to begin. Repeated or reminder notifications may be sent to each party at regular or decreasing intervals to remind them of an upcoming session. The notifications may contain a hyperlink to follow to join the session, a link to the RPI, an app notification or badge for display on the PED, or the address or phone number of another device address to connect to. The notification may further include a username, password, pin and/or other credential(s) that the invitees may provide to join the session. The length of the session may be at least partially based on the number of users connected and/or their priority levels.

Figure 18B:
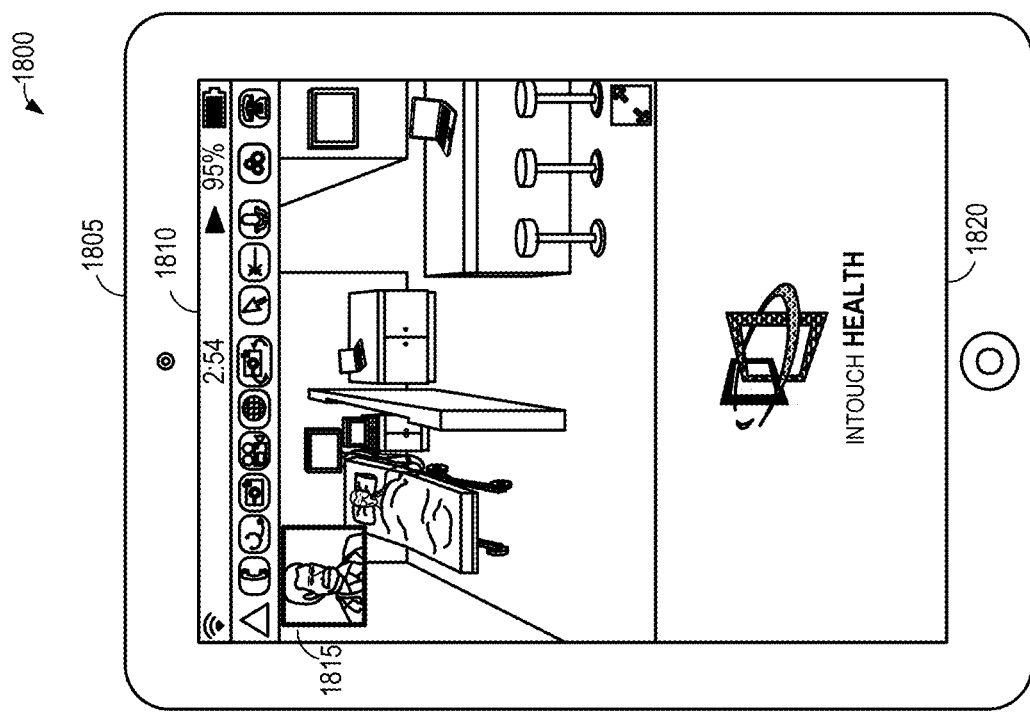
FIGS. 18A and 18B illustrate embodiments of what may be displayed during a consult on a telepresence device and via an RPI on a PED, respectively.
Figure 18A:
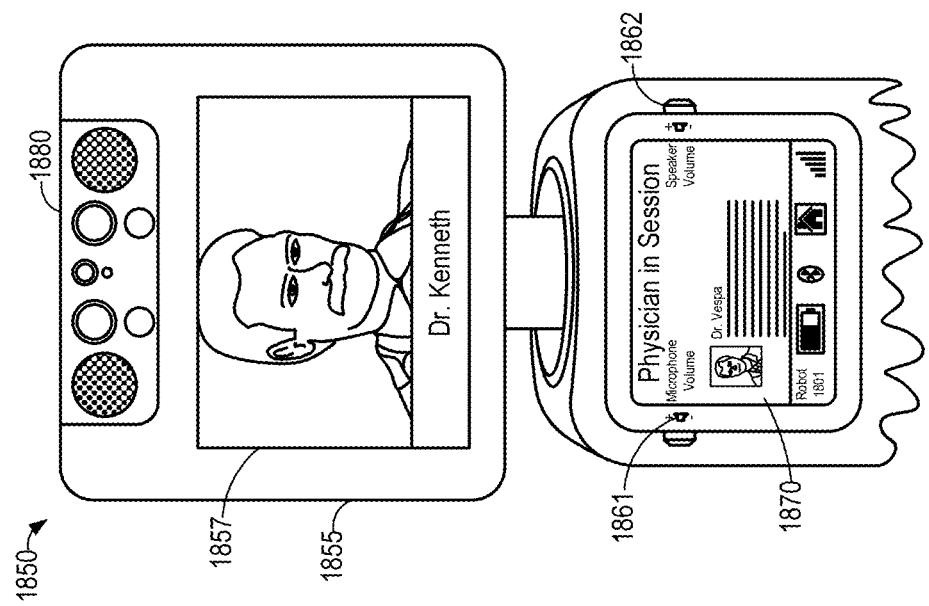

FIGS. 18A and 18B illustrate an embodiment 1800 of what may be displayed during a consult on a telepresence device 1850 and via an RPI on a PED 1805, respectively. As illustrated, the telepresence device 1850 may include audio and/or visual equipment 1880 to capture images and/or audio for display on the PED 1805. PED 1805 may include a camera to capture an image 1815 for display on a screen 1857 of a head portion 1855 of the telepresence device 1850. A lower portion of the telepresence device may include adjustment knobs for the microphone volume 1861 and/or the speaker volume 1862. Additionally, a screen 1870 may provide additional information about the user of the PED 1805. Accordingly, a patient being cared for via the telepresence device 1850 may see a healthcare practitioner using the RPI on the PED 1805. Similarly, the healthcare provider may see and interact with the patient via the telepresence device using the RPI on the PED 1805.

Figure 19:
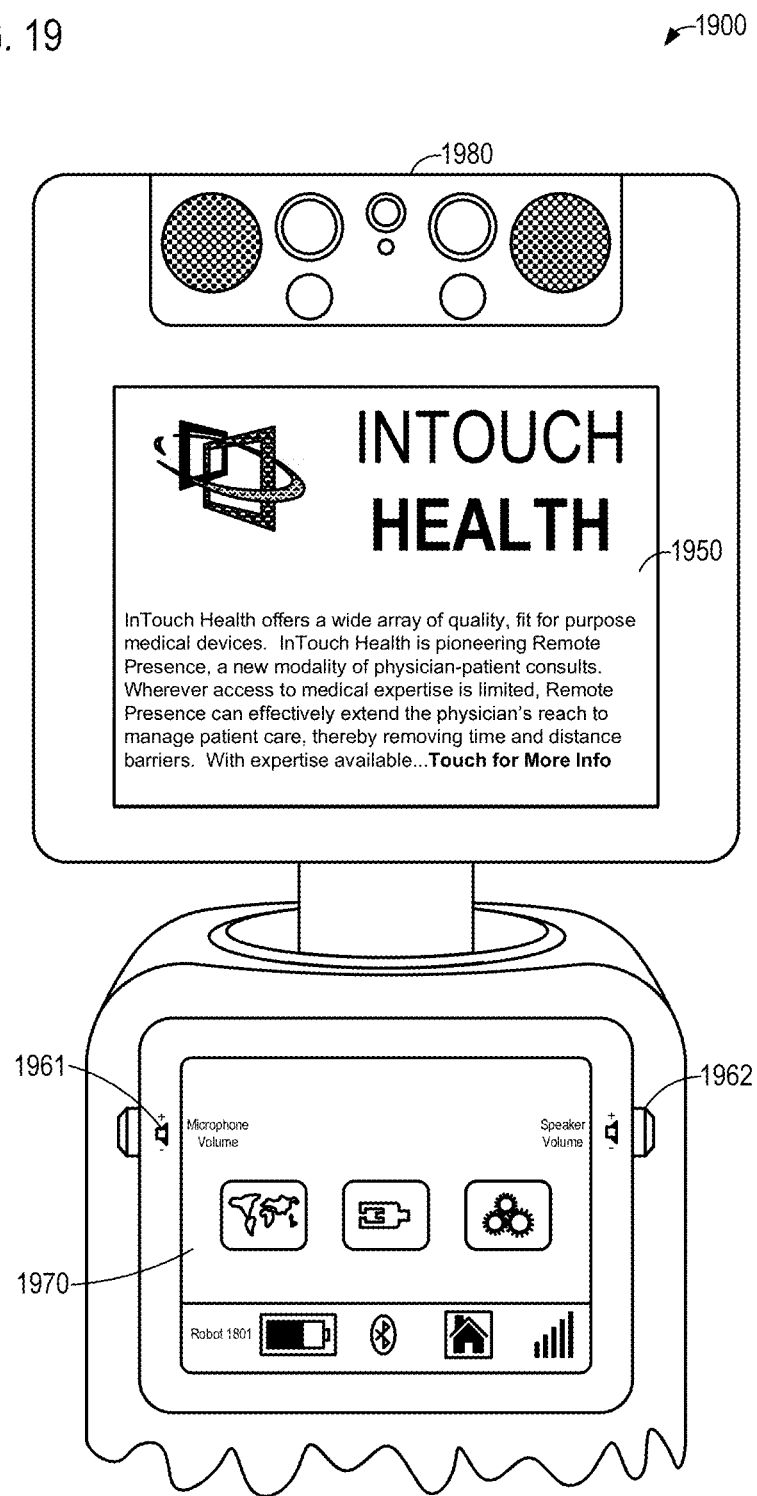
FIG. 19 illustrates an embodiment of a telepresence device in a screensaver mode.

FIG. 19 illustrates an embodiment of a telepresence device 1900 including audio and/or visual instruments 1980, controls 1961 and 1962, and displays 1950 and 1970. In a screensaver mode, the upper display 1950 may preserve the screen by displaying information about a company, the healthcare facility, medical facts, and/or other information associated with healthcare in general. A lower display 1970 may also enter an independent screen saver mode, and/or allow for user inputs associated with the telepresence device and/or the information displayed via the upper display 1950.

Figure 20:
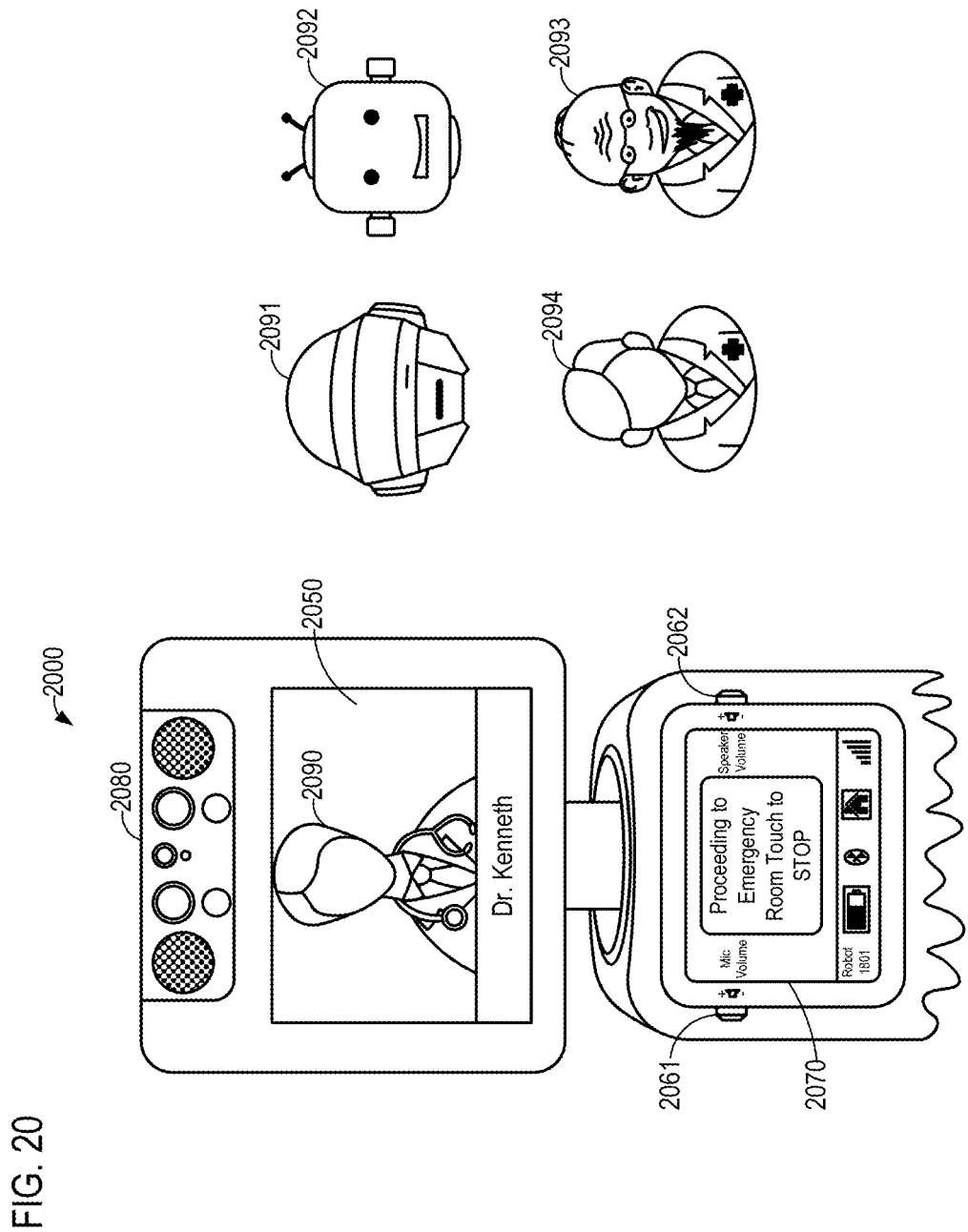
FIG. 20 illustrates various embodiments of avatars and/or personalities that may be assigned or used by a medical practitioner and/or telepresence device.

FIG. 20 illustrates various embodiments of avatars 2091, 2092, 2093, and 2094 and/or personalities that may be assigned or used by a healthcare practitioner and/or telepresence device. For instance, while the image 2090 displayed on the display 2050 may normally be associated with the image captured by a camera of a PED via the RPI, any of a wide variety of characters, avatars, cartoons, licensed caricatures, and/or other images may be used in place of an image received from the camera on the PED. The avatars 2091, 2092, 2093, and 2094 may be particularly useful to give human-like traits to the telepresence device. The telepresence device may, as previously described, include controls 2061 and 2062 for audio and a touch sensitive screen 2070.

Figure 21:
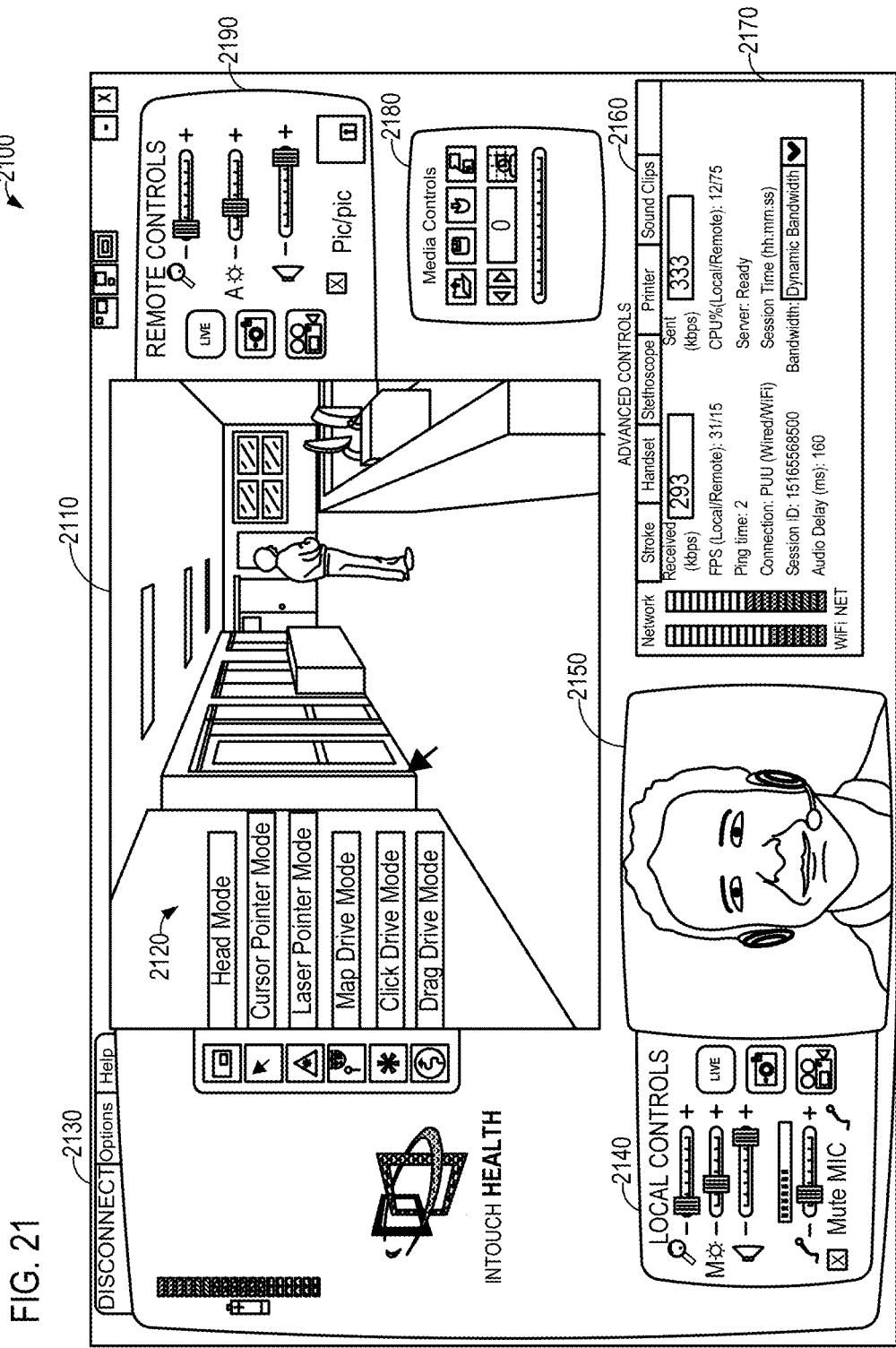
FIG. 21 illustrates an RPI configured to utilize various pointer-based navigational modes for navigating a telepresence device.

FIG. 21 illustrates an RPI that can be displayed on a PED including various informational, control, video, and settings panels 2120, 2130, 2140, 2150, 2160, 2170, 2180, and 2190. As illustrated, a live video feed may be displayed in a panel 2110. Remote brightness, zoom, and volume controls may be accessible via a panel 2190. Media management controls may be accessible via a panel 2180. Advanced controls with various tabs 2160 may be available via a panel 2170. A current image captured by a camera on the PED may be displayed in a panel 2150. Local zoom, brightness, volume, and microphone controls may be accessible via a panel 2140. Additional controls and tabs of control icons may be accessible via a panel 2130.

In the illustrated embodiment, a user of the RPI may select a navigation mode via a selection panel 2120. Inputs for selecting the navigation mode and/or inputs to direct the actual navigation may be performed using any of a wide variety of inputs, including, but not limited to, a voice input, a keyboard, a mouse, a touch input, a stylus, and/or via another peripheral input device. In each of the navigation modes 2120, a user may provide a navigation input in one or more manners. The navigation input may then be translated (processed, lookup table, etc) to generate and transmit navigation instructions to the telepresence robot to guide the telepresence robot, autonomously or semi-autonomously, to a desired location.

Figure 22:
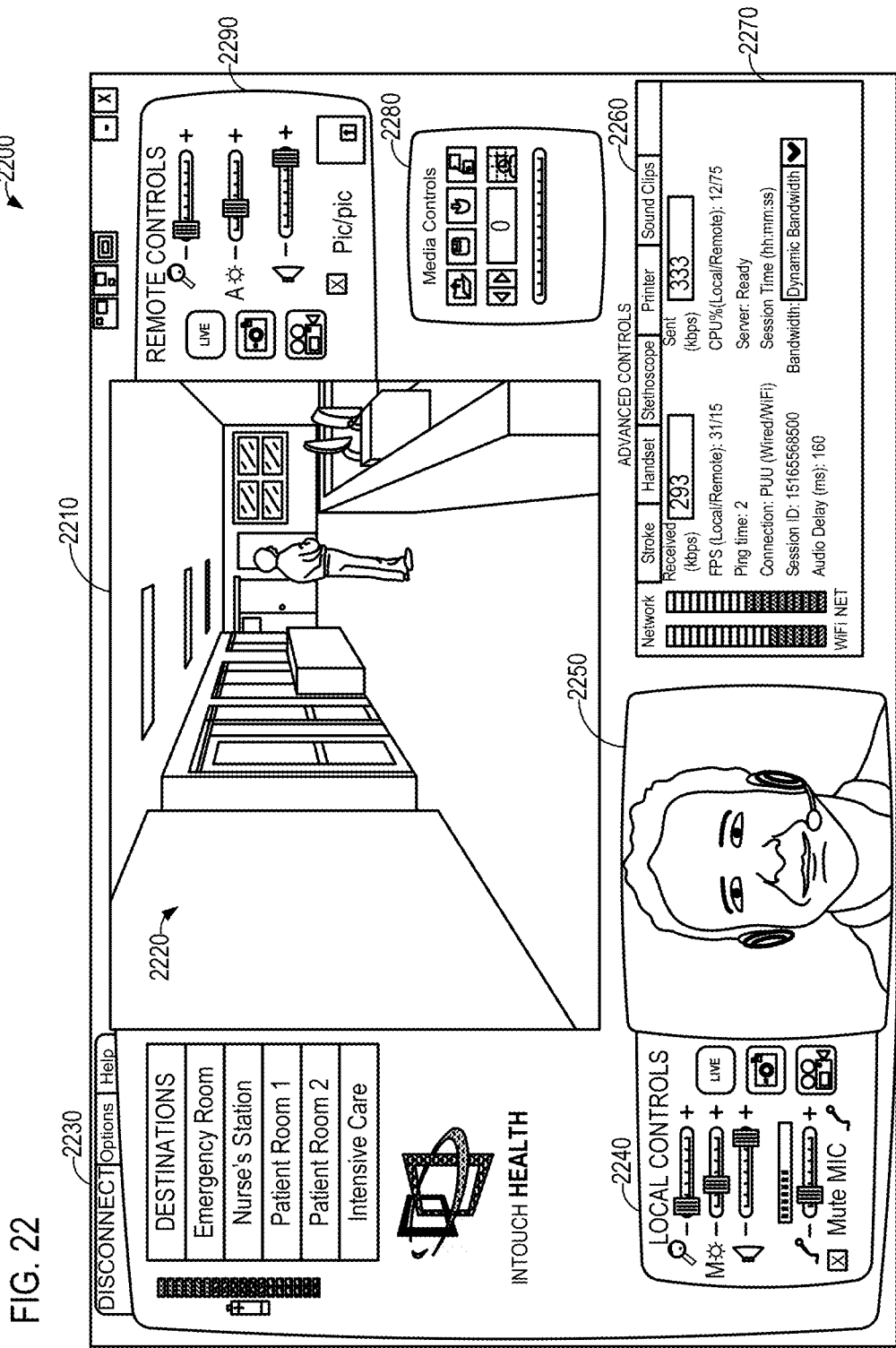
FIG. 22 illustrates an RPI configured to utilize destination-based navigational modes for navigating a telepresence device.

FIG. 22 illustrates an embodiment 2200 of an RPI configured to utilize destination-based navigational modes for navigating a telepresence device. As illustrated, a centralized panel 2210 may display a live video feed 2220. Various remote settings controls may be available in a panel 2290.

Another panel 2240 may provide similar audiovisual setting controls for a PED. A window 2250 may display the image currently captured by a camera on the PED. Advanced controls may be available in a panel 2270, and multiple tabs 2260 may provide for additional informational and/or control panels. The illustrated embodiment 2220 includes a destination navigation panel 2230 configured to allow a user to select from a list of destinations. Once a destination is selected, the RPI may facilitate communication with the telepresence device to direct the telepresence device to the selected destination. The telepresence device may be manually driven to the selected destination or may autonomously (or semi-autonomously) navigate to the selected destination.

According to various embodiments, the destinations may include various locations within a healthcare facility, specific patient names, and/or the names of various healthcare practitioners. In some embodiments, the locations of healthcare practitioners may be determined using cameras within the healthcare facility, global positioning systems, local positioning systems, radio frequency identification (RFID) tags, and/or the like.

Figure 23:
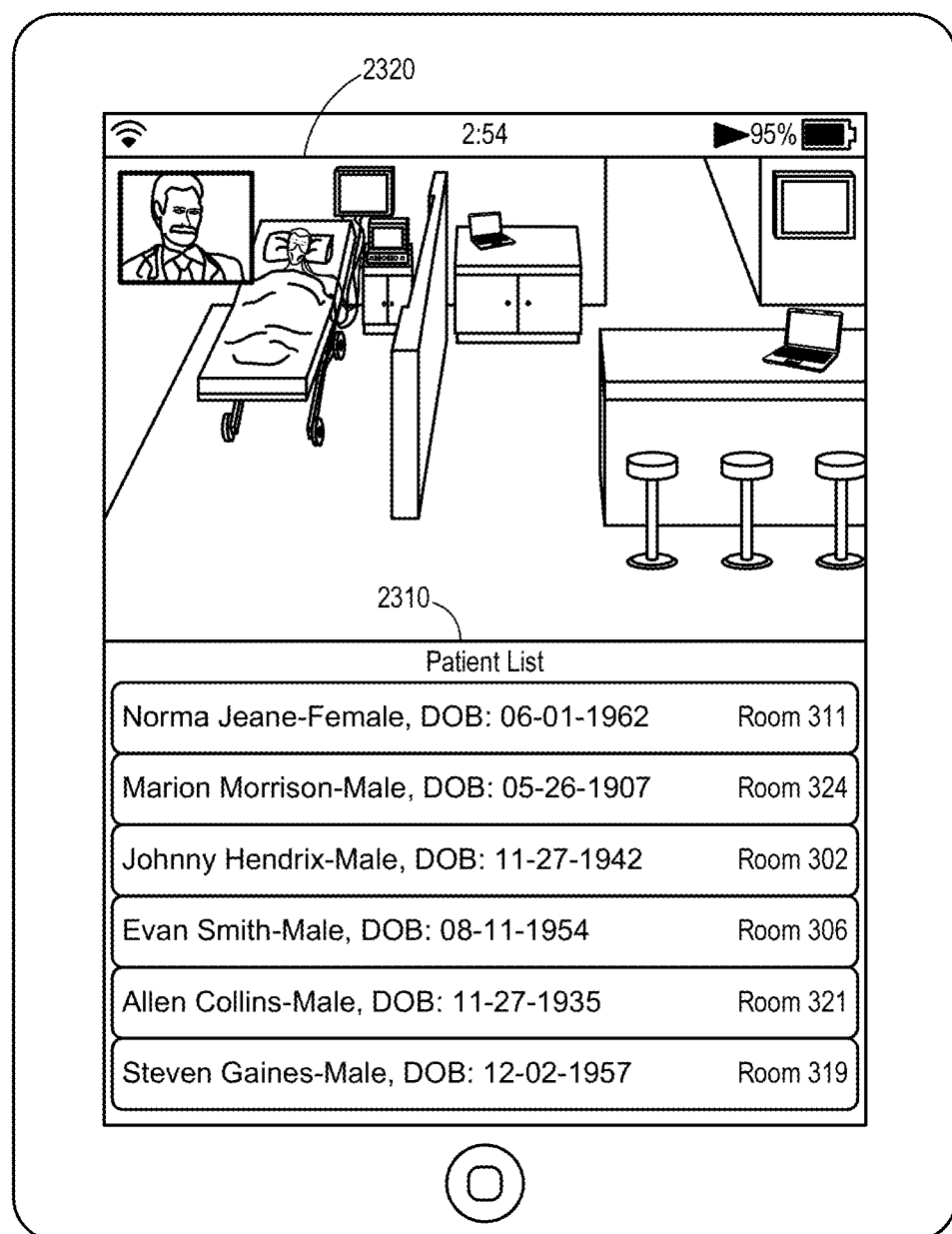
FIG. 23 illustrates a selectable destination patient list that can be used within an RPI to navigate a telepresence device.

FIG. 23 illustrates an embodiment 2300 of an RPI including a panel 2320 displaying a live feed from a telepresence device. A lower panel 2310 may display a list of patients. A user may select a patient on the patient list to direct the telepresence device to navigate to the selected patient. Again, the telepresence device may be manually driven, autonomously navigate, or semi-autonomously navigate to the selected destination.

Figure 24:
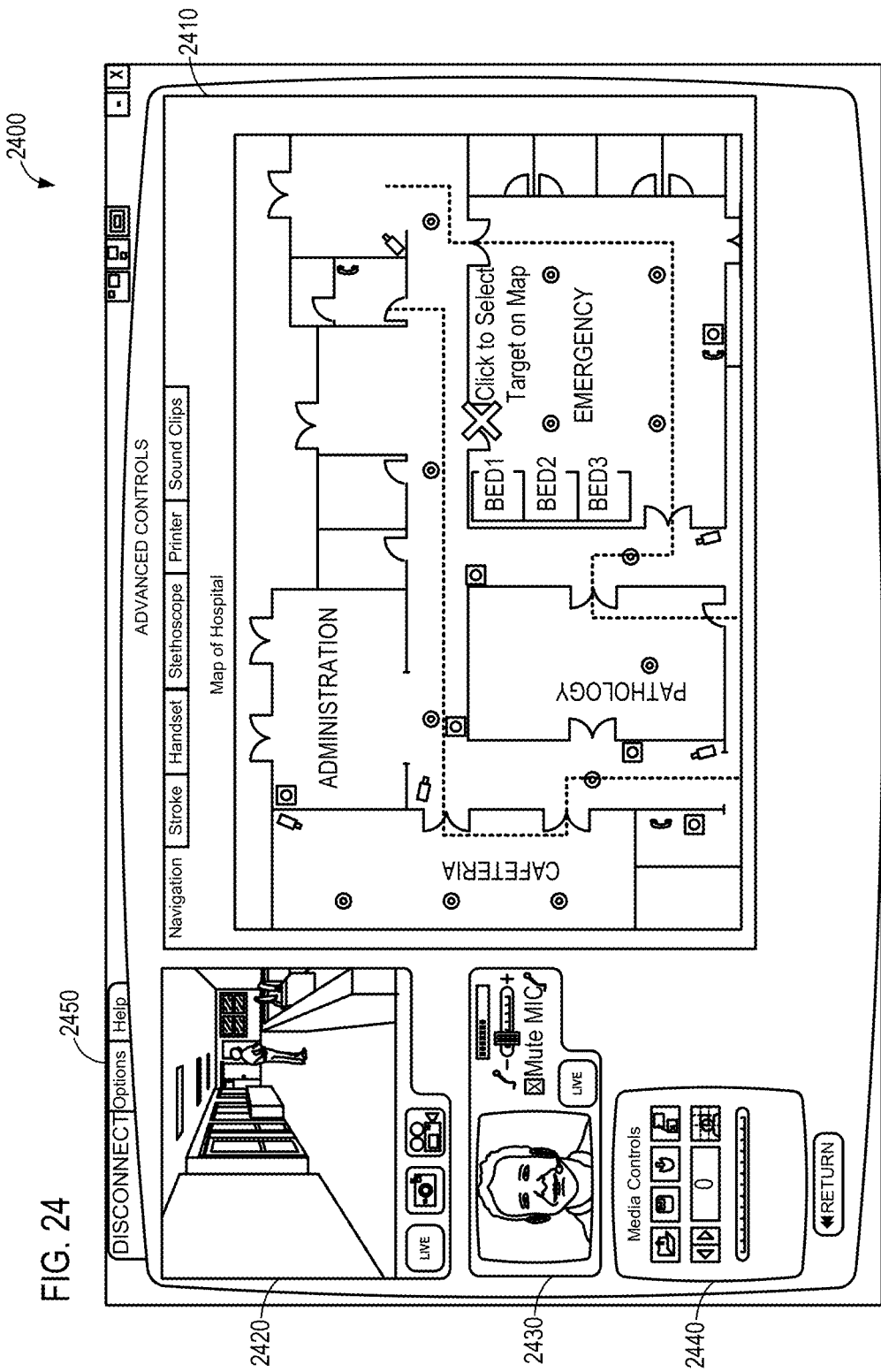
FIG. 24 illustrates an RPI configured to utilize map-based navigational modes for navigating a telepresence device.

FIG. 24 illustrates an embodiment 2400 of an RPI including panel 2410 of a plan view map allowing for map-based navigational modes for navigating a telepresence device. As illustrated, the map-based navigational mode may be part of an advanced control panel including multiple tabs. The size of the panel 2410 may be adapted to suit a particular need and may be user-selectable. Media controls 2440 may allow a user to capture audio and/or visual information from the live video feed in panel 2420. A panel 2430 may display the current image captured by a camera of a PED running the RPI. As illustrated the panel 2430 displaying the current image captured by the camera of the PED may include integrated settings controls. Various tabs 2450 may provide access to additional features, options, help, and/or navigation within the RPI.

Figure 25:
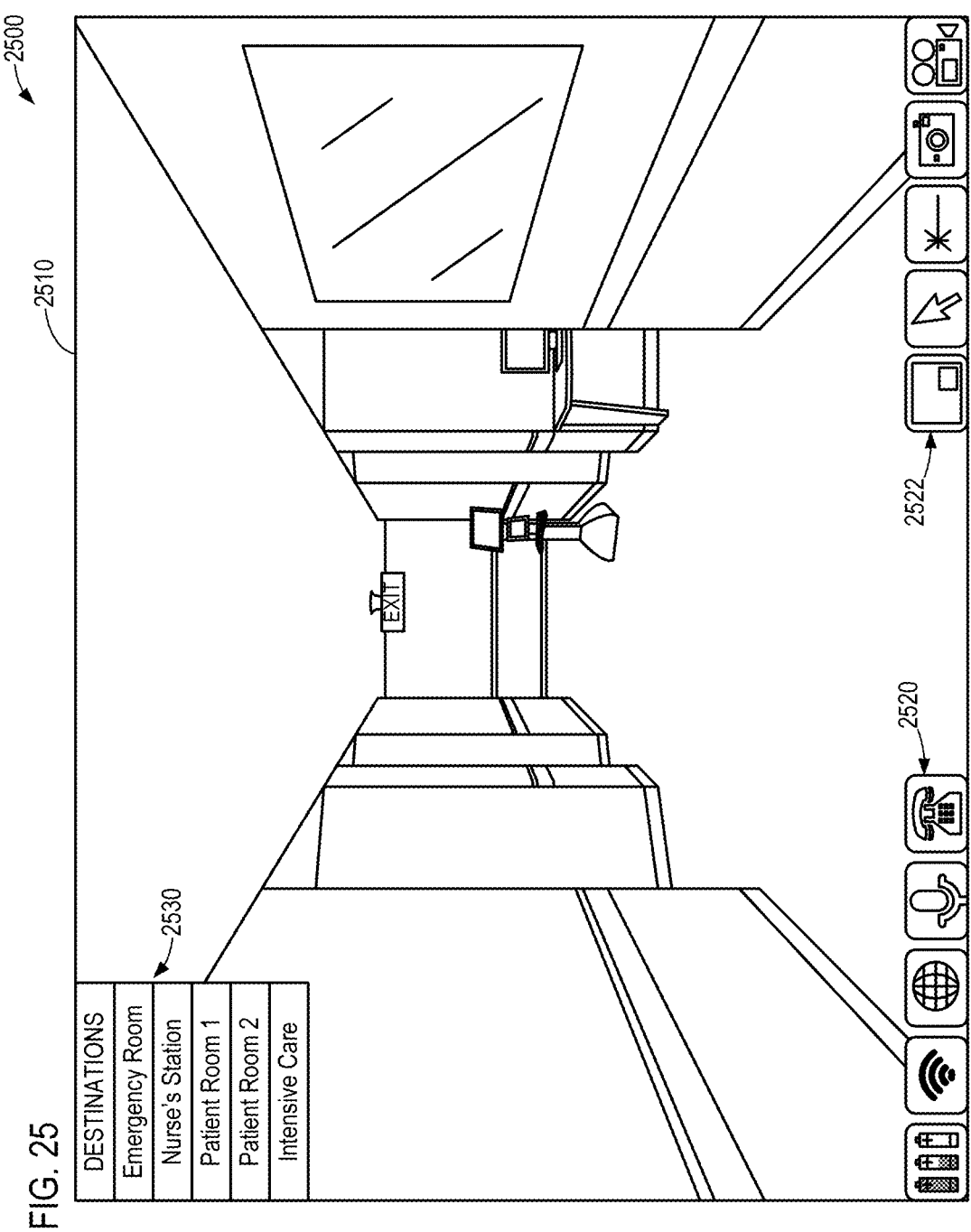
FIG. 25 illustrates a full-screen view of a hallway from a telepresence device as visualized on a PED via an RPI.

FIG. 25 illustrates an embodiment 2500 of a full-screen view of a hallway from a telepresence device as visualized on a PED via an RPI. The panel 2510 may display a live video feed from a telepresence device. Icons 2520 and 2522 may be overlaid on the video feed and may provide access to various controls or settings. A destination panel 2530 may also be overlaid on the video feed and allow a user to select a destination. As in previous embodiments, the RPI may communicate a selected destination to the telepresence device, which may autonomously or semi-autonomously navigate to the selected destination.

Figure 26:
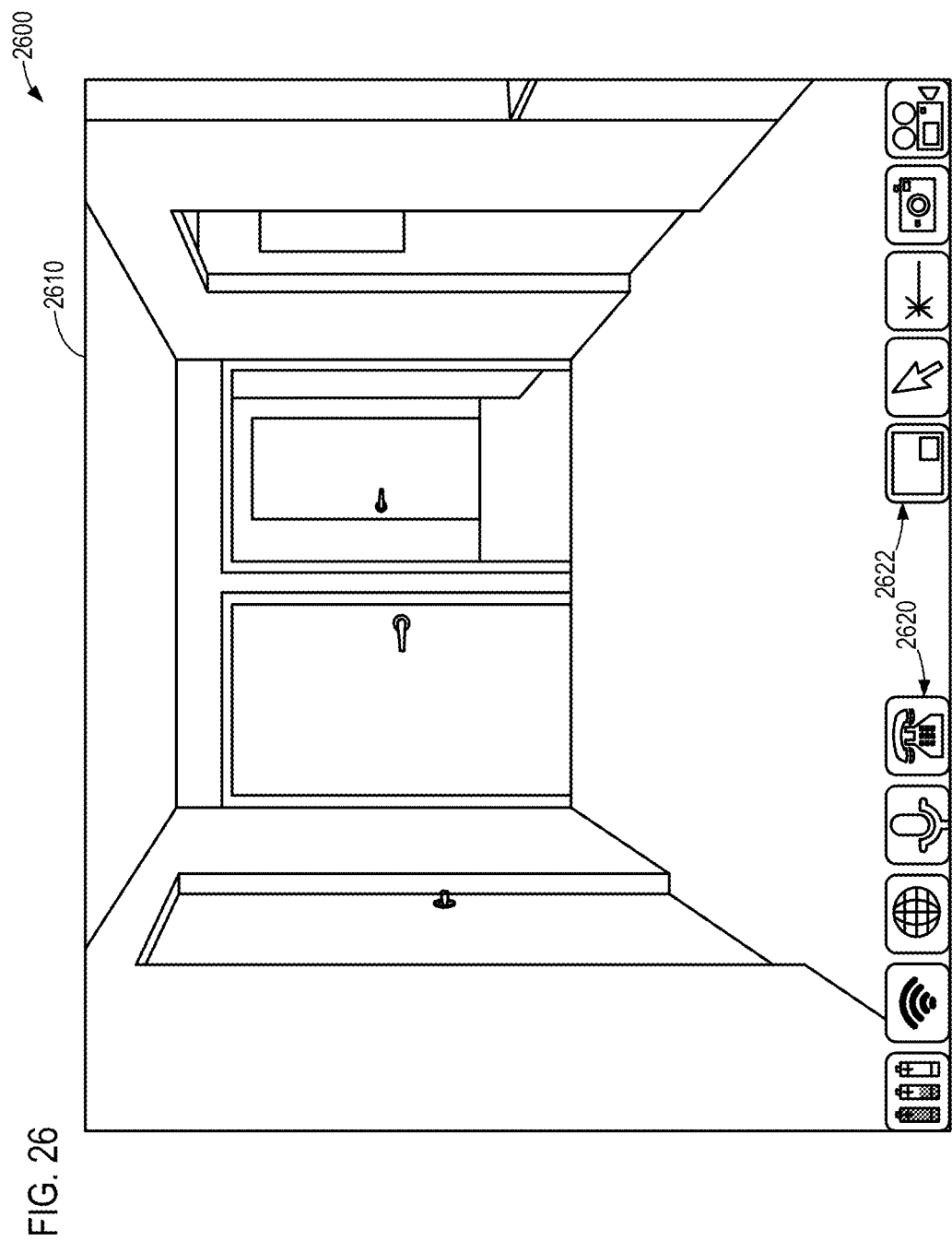
FIG. 26 illustrates a full-screen view of various doorways in a healthcare facility, as visualized on a PED via an RPI.

FIG. 26 illustrates an embodiment 2600 of a full-screen view of a live video feed from a telepresence device as may be displayed via an RPI. Various icons 2620 and 2622 may provide access to various features, settings, options, and/or other aspects of the RPI. The icons 2620 and 2622 may be overlaid on the live video feed or a separate panel may be displayed containing icons 2620 and 2622.

Figure 27A:
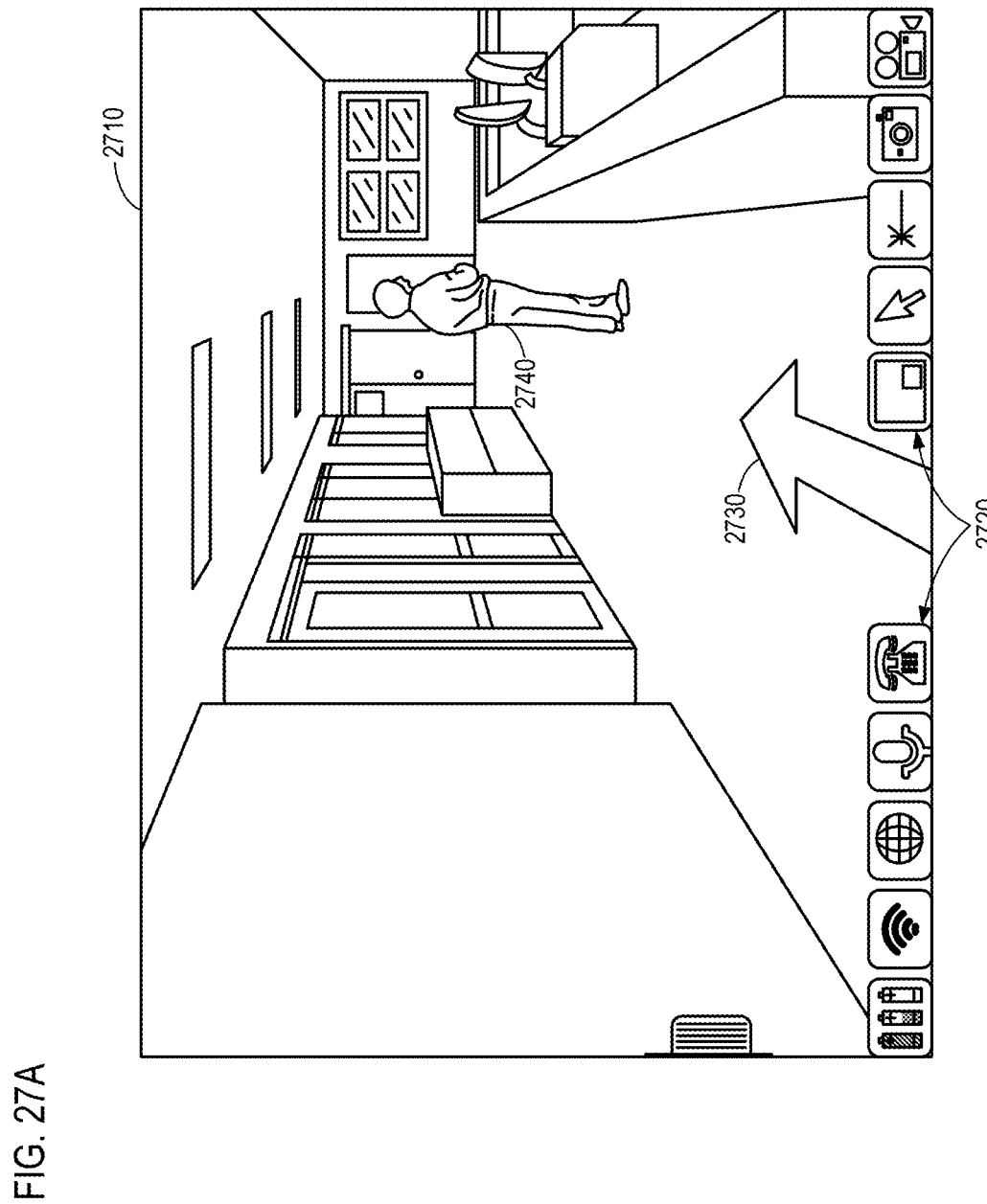
FIG. 27A illustrates an intended or directed navigation path of a telepresence device as visualized on a PED via an RPI.

FIG. 27A illustrates another embodiment 2710 of a live video feed from a telepresence device, as may be displayed via an RPI. An arrow 2730 may be overlaid on the video feed as a navigation input to indicate an intended or desired navigation path of a telepresence device. The arrow may be drawn by the RPI after receiving the live video feed or by the telepresence device prior to sending the live video feed. In some embodiments, the user may draw the arrow 2730 to indicate a desired direction of travel. The arrow 2730 may then be translated by the RPI or by the telepresence device into directional commands to navigate the telepresence device. Again, various icons 2720 may provide access to various features, settings, options, and/or other aspects of the RPI. The icons 2720 may be overlaid on the live video feed or a separate panel may be displayed containing icons 2720. The arrow 2730 may be a vector quantity describing both the direction and the velocity (current, planned, or directed) of the telepresence device.

The arrow 2730, provided as a navigation input, may be used to generate navigation instructions that are transmitted to a remote telepresence device. As illustrated, the navigation input may be in the form of a vector (arrow 2730) drawn as either a final endpoint selection or as a vector including a beginning point and an end point. The end point of the vector may represent the location to which the telepresence device should navigate. Accordingly, navigation instructions may be generated based on the current location of the telepresence device and the endpoint of the vector within the live video feed. In some embodiments, the vector's image pixel endpoint may be mapped via a lookup table to one or more translate and rotate commands to cause the telepresence device to navigate to the selected location. In some embodiments, the length of the vector may correspond to the desired distance to move the telepresence device, a desired acceleration of the telepresence device, and/or a desired velocity of the telepresence device.

As previously described, a navigation input may direct a telepresence device to navigate forward (with respect to the live video feed) 3 meters and to the right 2 meters. Any of a wide variety of navigation instructions may be possible to correctly navigate the telepresence device. For instance, the navigation instructions may direct the telepresence device to navigate approximately 3.6 meters at a 34 degree angle relative to the video feed. Alternatively, the navigation instructions may direct the telepresence device to navigate 3 meters forward and then 2 meters to the right. As will be appreciated, any number of navigations routes and corresponding navigation instructions may be possible. The navigation input may be translated into navigation instructions as a plurality of drive forward commands coupled with rotate commands.

In some embodiments, the live video feed may be delayed slightly due to network and/or processing limitations. This video latency may result in inaccurate navigation instructions. Accordingly, the navigation input may be adjusted based on the known video latency and the current or past velocity and direction of the robot. For example, the selection of a location within the video feed may be translated into navigation instructions that compensate for the latency of the video feed. For instance, if an end point (endpoint pixel) of a vector drawn on the video feed maps to a position 1 meter forward and 0.5 meters to the right relative to the current location of the telepresence device, and the telepresence device has moved 0.2 meters forward since the video frame on which the vector was drawn was captured, or since the associated command was issued, a lookup table entry for 0.8 meters forward and 0.5 meters to the right may be used to determine and/or adjust the navigation instructions. Video latency calculation and command compensation may be performed at the telepresence device, at a remote interface device, and/or at any networked computing device. In some embodiments, the navigation instructions may be generated to compensate for the video latency. In other embodiments, the telepresence device and/or other computing device may adjust the navigation instructions to compensate for the video latency.

Figure 27B:
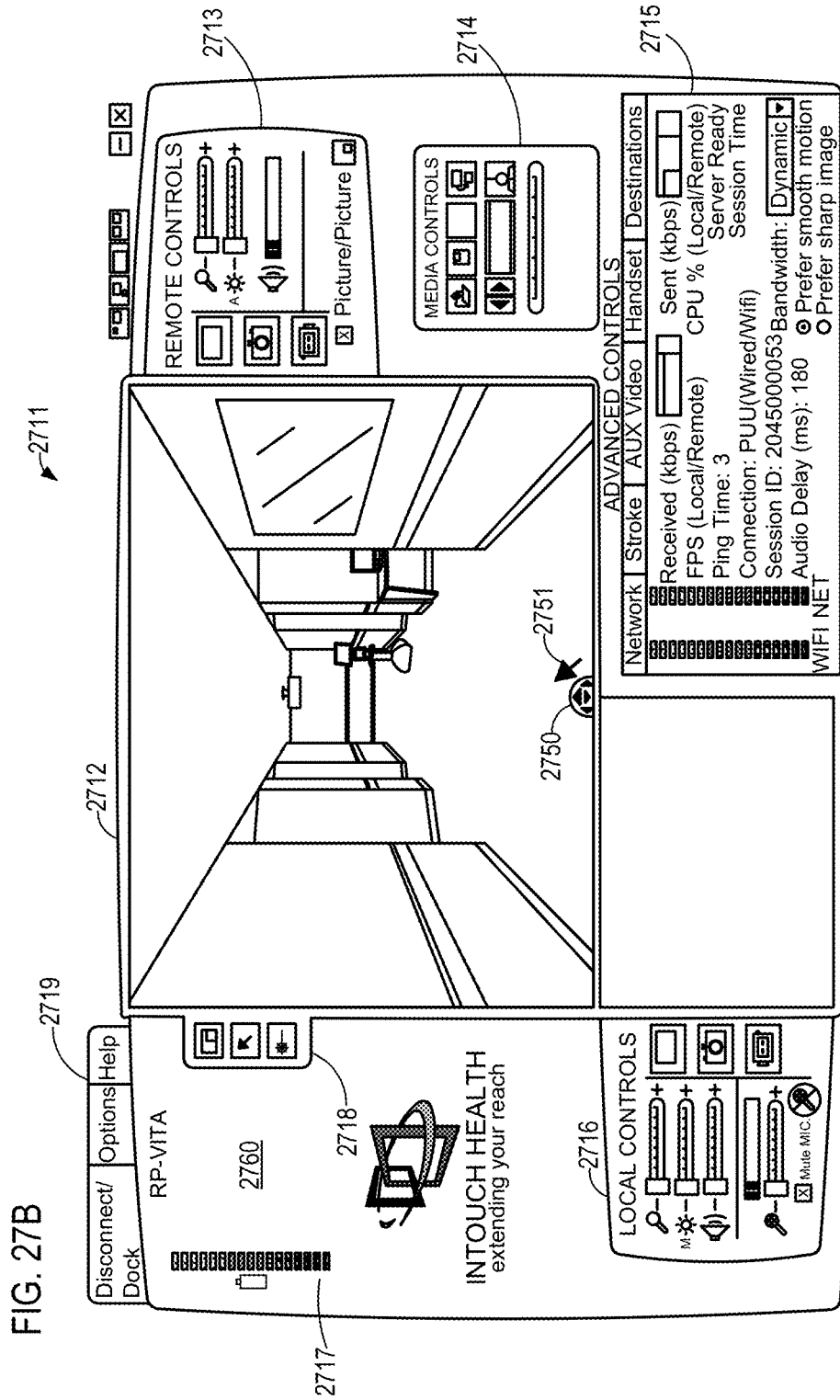
FIG. 27B illustrates a mouse-based driving interface for navigating a telepresence device via an RPI.

FIGS. 27B-27H illustrate various aspects of a mouse-based driving interface 2711 of an RPI for manually or semi-autonomously controlling a telepresence device. As illustrated in FIG. 27B, the mouse-based driving interface 2711 for navigating a telepresence device via an RPI may be presented within a live video feed 2712 from the telepresence device. A four way controller 2750 may be overlaid on the live video feed. According to various embodiments, the arrows of the four way controller 2750 may be selected by a finger or stylus on a touch screen device or via a pointer 2751 on a touch screen device or as controlled by a peripheral device (e.g., a keyboard or mouse). For instance, a user may operator a mouse to control the pointer 2751 and click on one of the arrows on the four way controller 2750.

In some embodiments, the live video feed 2712 and the four way controller 2750 may be displayed in a full-screen or expanded mode. In other embodiments and/or modes, various additional panels, icons, tabs, and/or other objects 2713, 2714, 2715, 2716, 2717, 2718, and 2719 simultaneously with the mouse-based driving interface. For example, a remote controls panel 2713 may allow a user to control various settings of the remote telepresence device, such as the audio and video settings. A media control panel 2714 may allow a user to open, play, record, and/or otherwise manipulate the current live video (or audio) feed 2712, network-accessible audiovisual material, remotely (at the telepresence device) stored audiovisual material, and/or locally stored audiovisual material.

An advanced controls panel 2715 may allow a user (or select users based on account privileges) to modify various aspects of the connection or session settings, access external or peripheral applications (e.g., StrokeRESPOND), and/or control other aspects of the remote telepresence session. A local controls panel 2716 may allow a user to control various settings of the RPI, the PED, and/or other local peripheral devices, such as the audio and video settings associated with the telepresence session. A battery life indicator 2717 may provide information regarding the current battery life and/or expected battery life based on current or past consumption rates. Various additional icons and tabs 2718 and 2719 may provide additional controls and/or options within the RPI and/or associated with the remote telepresence device.

Figure 27C:
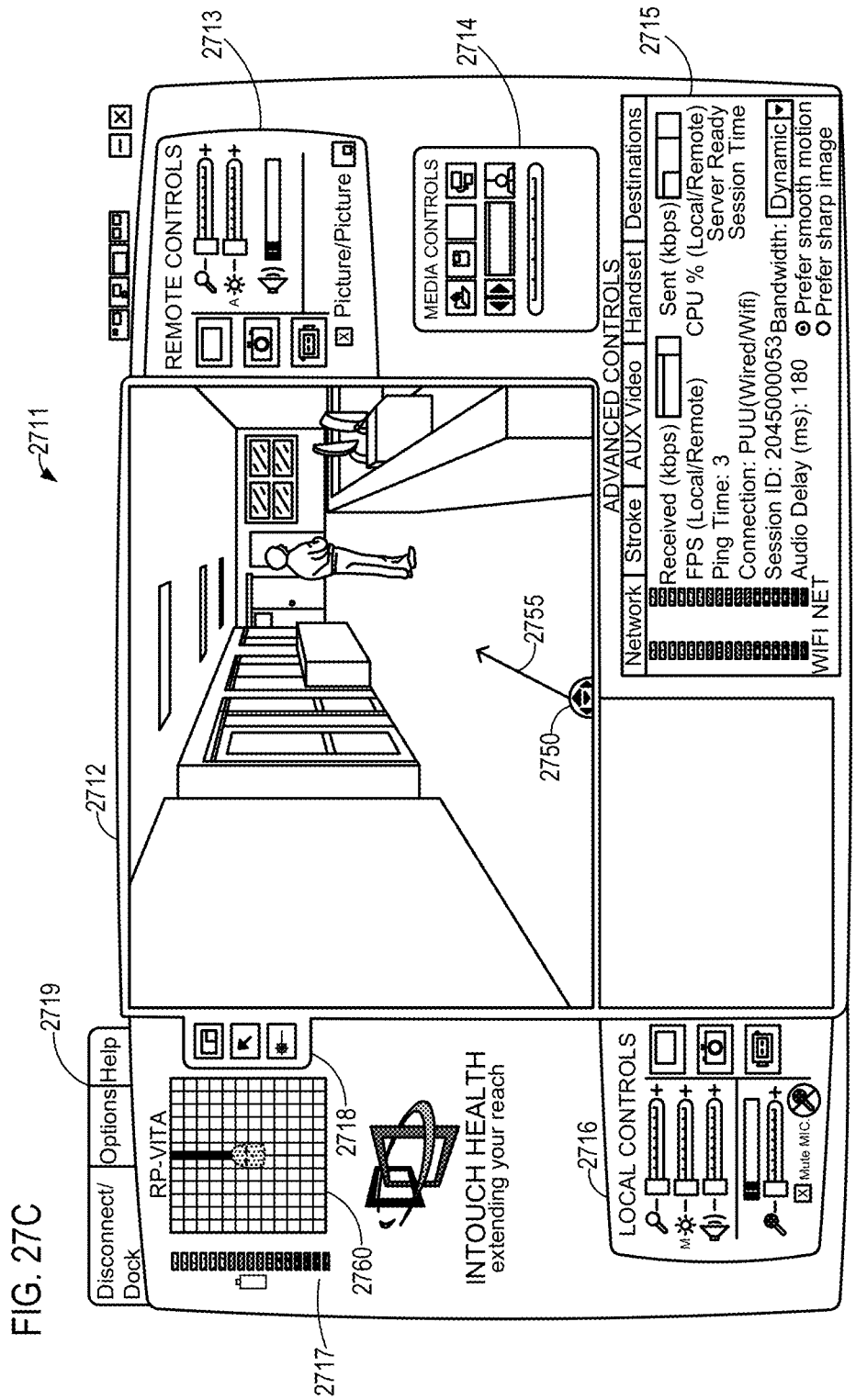
FIG. 27C illustrates the mouse-based driving interface with long drive vector drawn on the video feed to indicate a direction and a relatively fast velocity.

FIG. 27C illustrates the mouse-based driving interface 2711 with long drive vector 2755 drawn on the video feed to indicate a direction and a relatively fast velocity. According to various embodiments, the direction of the vector may be associated with an intended, directed (as directed by the user of the RPI), and/or current direction of travel. In various embodiments, a user may click the uppermost arrow of the four way controller 2750 and then drag a vector to describe a desired direction of travel. The length (magnitude) of the vector may correspond to the velocity and/or acceleration of the telepresence device. Additionally, a grid display 2760 may illustrated the current direction of travel and/or the velocity (magnitude) of the telepresence device on a grid. The grid may correspond and/or display travel angles (e.g., in degrees, radians, with respect to north, etc.) and/or a velocity as a numeric or descriptive value. For example, the length of the dark line on the grid display 2760 may be aligned with numbers between 1 and 10 or descriptive terms like "slow," "medium," and "fast."

Figure 27D:
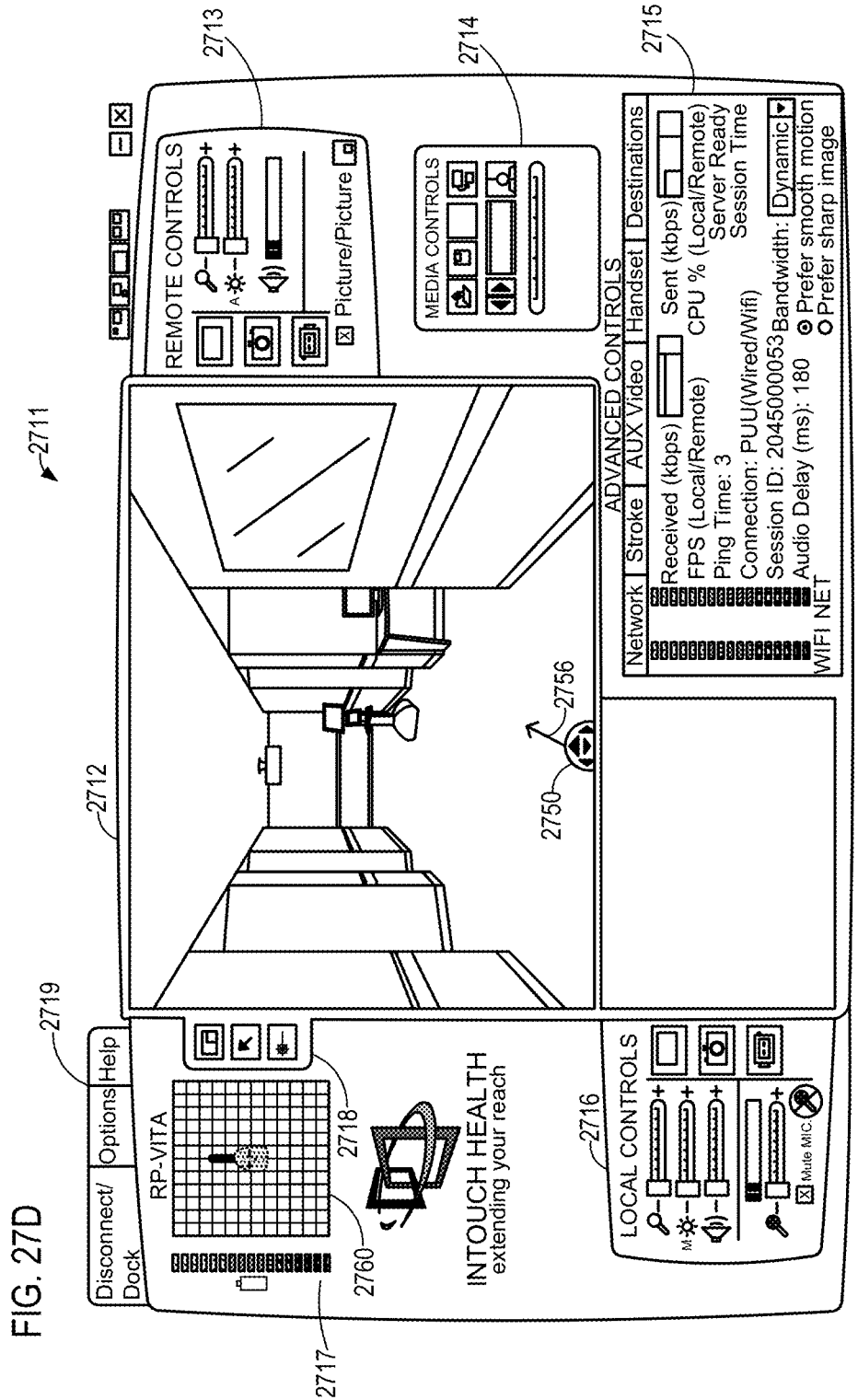
FIG. 27D illustrates the mouse-based driving interface with a short drive vector drawn on the video feed to indicate a direction and a relatively slow velocity.

FIG. 27D illustrates the mouse-based driving interface 2711 with a short drive vector 2756 drawn on the video feed to indicate a direction and a relatively slow velocity. A corresponding display of a short line may be displayed in the grid display 2760.

In various embodiments, a navigation input in the form of a vector provided in a mouse-based vector input mode may be translated into navigation instructions through the use of a lookup table. In some embodiments, the lookup table may include values that compensate for latency. That is, the navigation instructions returned by the lookup table may be based on the navigation input and the current or recent average video latency, as described herein.

Figure 27E:
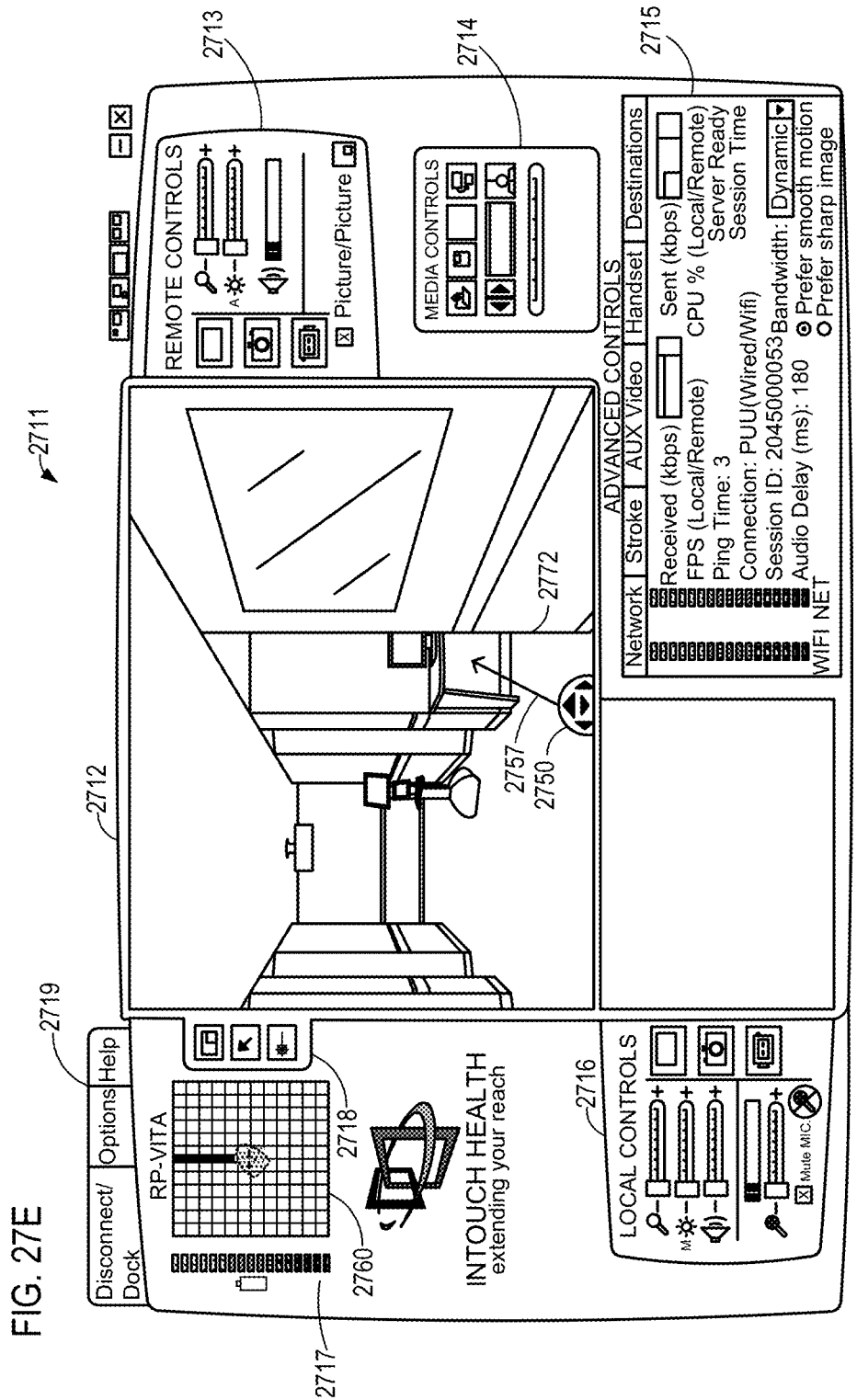
FIG. 27E illustrates the mouse-based driving interface with a vector for rounding a corner within the RPI.

FIG. 27E illustrates the mouse-based driving interface 2711 with a vector 2757 for rounding a corner 2772 within the RPI. According to various embodiments, the RPI and/or telepresence device may detect objects such as the walls to determine passable hallways and corridors. Alternatively or additionally, the RPI and/or telepresence device may utilize maps to determine that a vector 2757 is intended to direct a telepresence device to turn down a different hallway or round a corner. As illustrated, the vector 2757 in FIG. 27E may be intended to round corner 2772. In some embodiments, the user may draw a rounded or curved vector 2757. In other embodiments, the RPI and/or telepresence device may interpret a straight vector 2757 as intended to direct the telepresence device down the hallway.

Figure 27F:
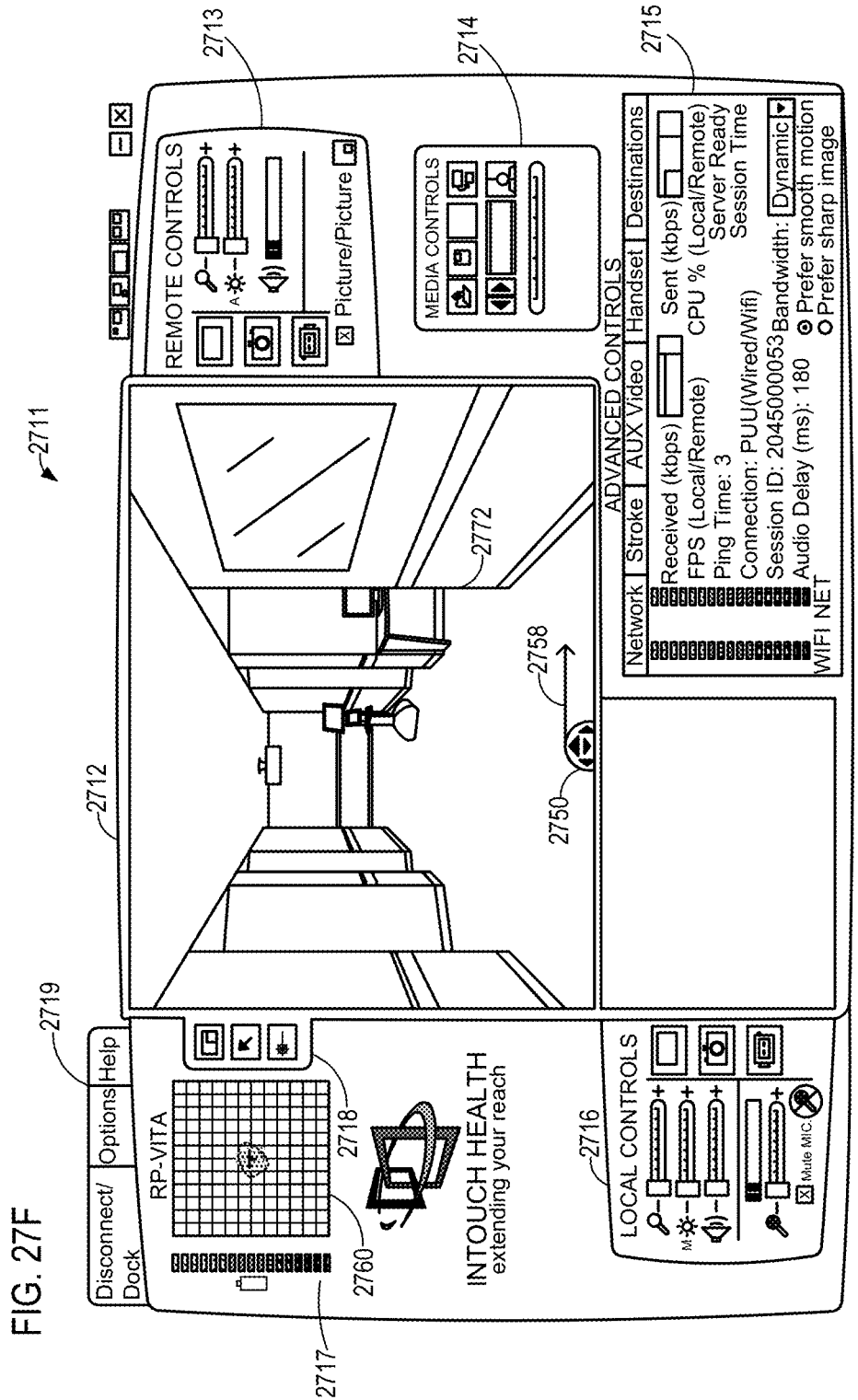
FIG. 27F illustrates the mouse-based driving interface with a vector drawn to cause the telepresence device to spin in place.

FIG. 27F illustrates the mouse-based driving interface 2711 with a vector 2758 drawn to cause the telepresence device to spin in place. According to various embodiments, a horizontal vector 2758 (relative to the live video feed 2712) may be used to direct the telepresence device to spin in place either clockwise or counterclockwise depending on the direction of the horizontal vector 2758.

Figure 27G:
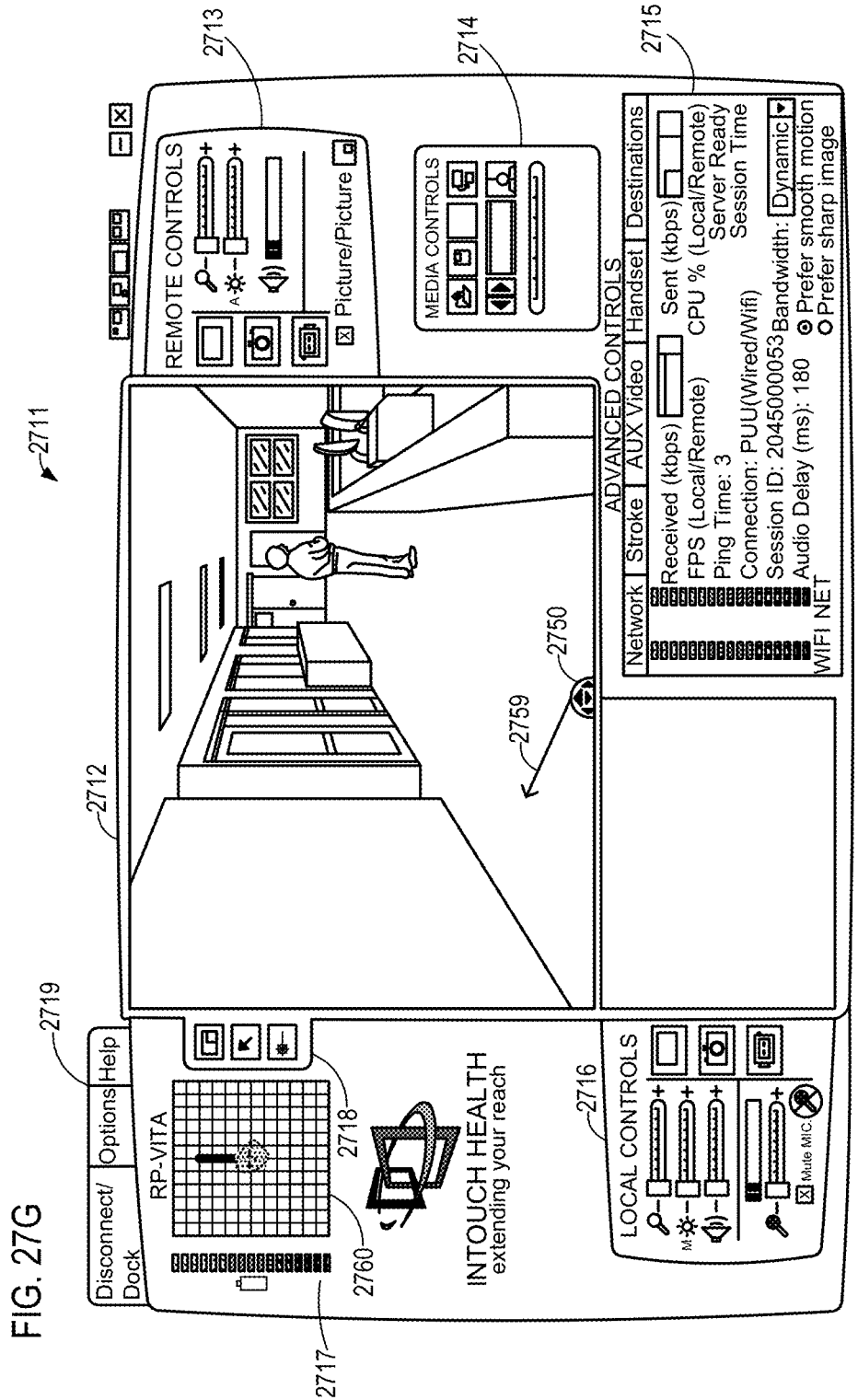
FIG. 27G illustrates the mouse-based driving interface with a vector drawn towards an object.

FIG. 27G illustrates the mouse-based driving interface 2711 with a vector 2759 drawn towards an object (a wall). According to various embodiments, the mouse-based driving interface may prevent the telepresence device from colliding with objects (such as walls, people, and other objects). As previously described, an obstacle detection/obstacle avoidance (ODOA) system may prevent such collisions. In some embodiments, a user may deactivate the ODOA system, such that the user may operate in a "nudge mode" and continue to slowly move the telepresence device despite the telepresence being in contact with or close proximity to another object. This mechanism may automatically time-out such that the ODOA system is re-engaged after a period of inactivity.

Placing the telepresence device in nudge mode may cause a camera of the telepresence device to be automatically positioned to look down around the body of the telepresence device and either in the direction of drive command issued by the user or in the direction of an object closest to or in contact with the telepresence device (so that the user may see what obstacle he or she is commanding the telepresence device to nudge). Alternatively, the ODOA system may be entirely deactivated. In one embodiment, the ODOA system may be deactivated so long as the telepresence device is driven or moved below a specified velocity.

Figure 27H:
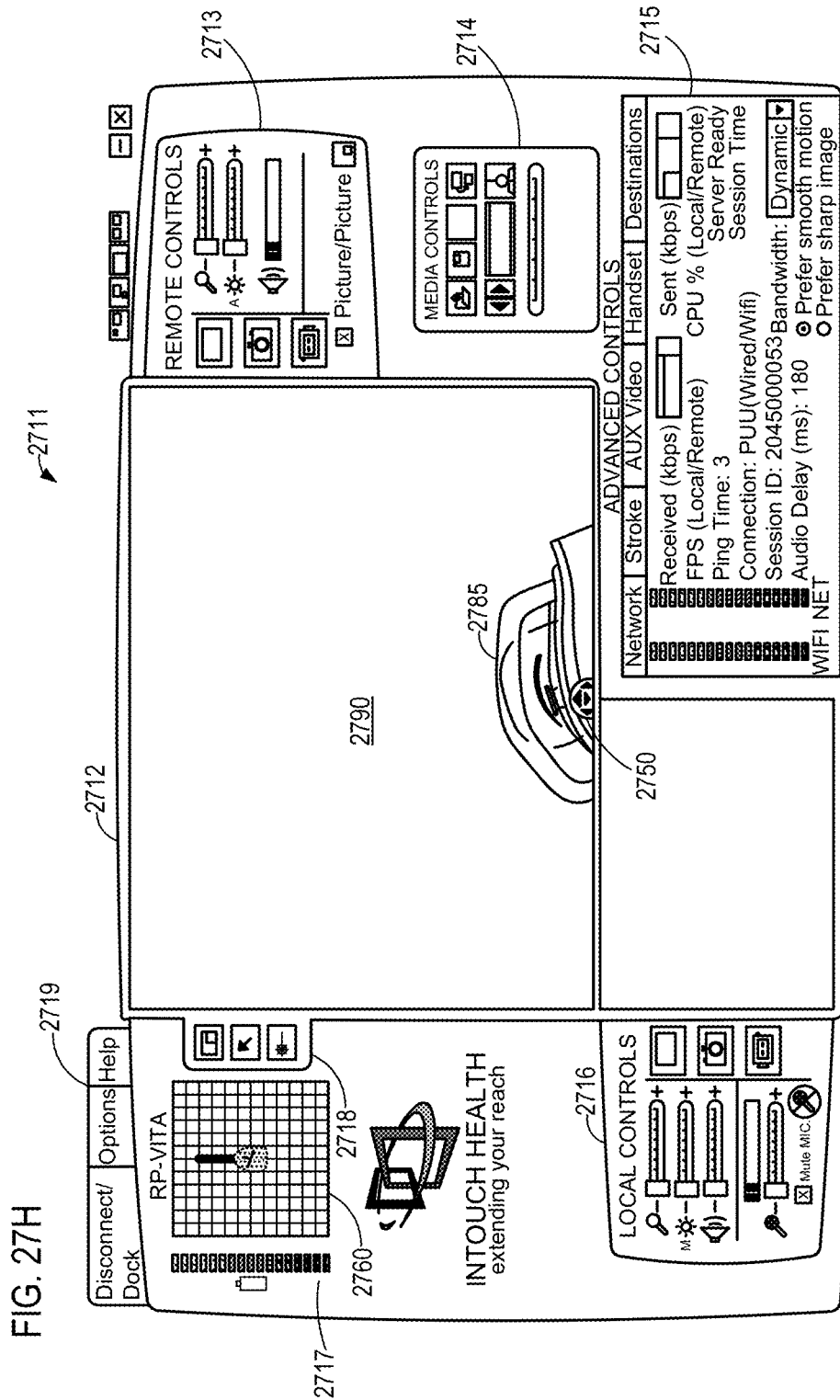
FIG. 27H illustrates the mouse-based driving interface used to reverse the telepresence device with a camera of the telepresence device oriented in reverse and slightly downward.

FIG. 27H illustrates the mouse-based driving interface 2711 used to reverse the telepresence device 2785 with a camera of the telepresence device (or other associated camera) oriented in reverse and slightly downward toward the floor 2790. In some embodiments, by selecting (touch or mouse click) the bottom arrow of the four way controller 2750, the telepresence device 2785 may be reversed. The reverse mode may allow for vector controls (direction and velocity) or may alternatively reverse straight back and at a constant velocity. In some embodiments, a rear camera may be displayed on the live video feed 2712 to show the direction of travel and help prevent the telepresence device 2785 from colliding with objects. In other embodiments, a head portion of the telepresence device may be rotated to the direction of travel (reverse) and/or inclined slightly downward to facilitate the reverse navigation.

In various embodiments of the mouse-based driving interface, the controls and vectors may be "drawn" as overlays on the live video feed (e.g., via a click and hold of a mouse button or a tap and hold via a stylus or finger). In other embodiments, a panel or peripheral device may be used to "draw" the vectors to control the velocity and/or direction of travel. In some embodiments, the velocity selected by the length of the vector may be overridden based on other factors (such as obstacle detection, congestion, human presence, etc.).

According to various embodiments, a head portion and/or the camera of the telepresence device may be re-centered via an icon within the mouse-based driving interface 2711 or via a keyboard (or other peripheral device) selection. In some embodiments, the selection of any of the arrows within the four way controller 2750 may orient or re-orient the head portion of the telepresence device.

Figure 28:
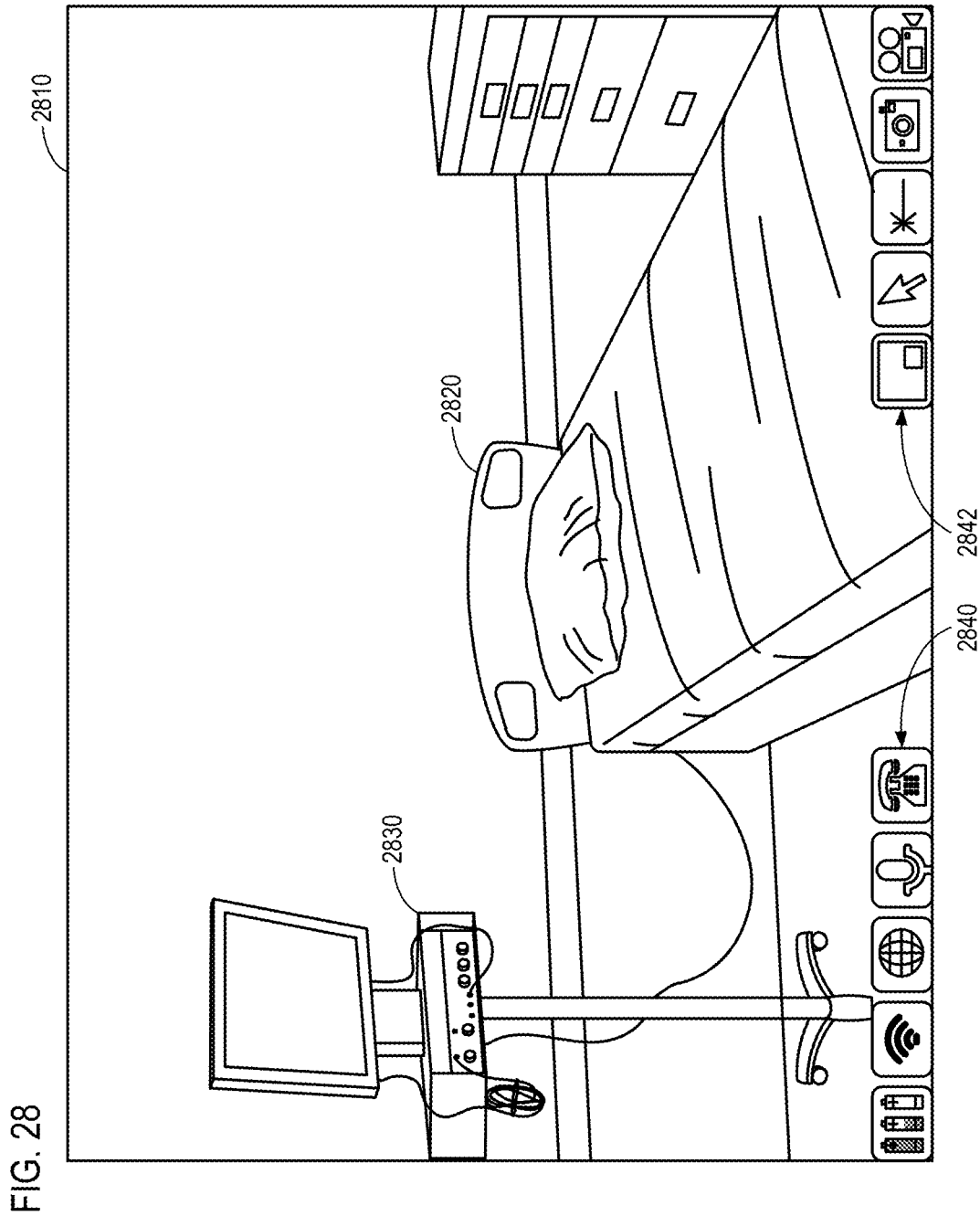
FIG. 28 illustrates a bedside view of a patient bed and an associated patient monitor, as visualized on a PED via an RPI.

FIG. 28 illustrates an embodiment 2810 of full-screen live video feed from a telepresence device including a bedside view of a patient bed 2820 and an associated patient monitor 2830. As illustrated, the live video feed may be able to visualize a patient in a patient bed 2820 as well as a patient monitor. In some embodiments, the RPI and/or the telepresence device may detect a refresh rate of the patient monitor 2830 and dynamically match the refresh rate to reduce scrolling bars and/or flickering. In other embodiments, the live video feed of the patient monitor 2830 may be digitally enhanced to reduce the flickering and/or scrolling bars.

Figure 29:
FIG. 29 illustrates a click-to-zoom feature of an RPI that can be used when medical practitioners and/or other users visualize a patient on a PED via an RPI.

FIG. 29 illustrates an embodiment 2910 of an RPI including a click-to-zoom feature 2925. The click-to-zoom feature 2925 may be used to zoom in on a specific area of a live video feed, a captured video feed, or a still image. The box defining the click-to-zoom feature 2925 may be drawn as a box, or by dragging one or more corners. Depending on the PED used, the RPI may receive the click-to-zoom box using any of a wide variety of input devices, such as via a touch, a stylus, or a mouse pointer.

FIG. 29 also illustrates a multi-party session. In the illustrated embodiments, multiple users are shown in a session guests panel 2930. The session guests panel 2930 may include images captured by PEDs associated with each of the guests. Accordingly, multiple users may participate simultaneously. In such embodiments, one or more of the users may have limited access and/or control of the telepresence device. As in previous embodiments, control and options icons 2940 and 2942 may be overlaid and provide access to various features of the RPI.

Figure 30:
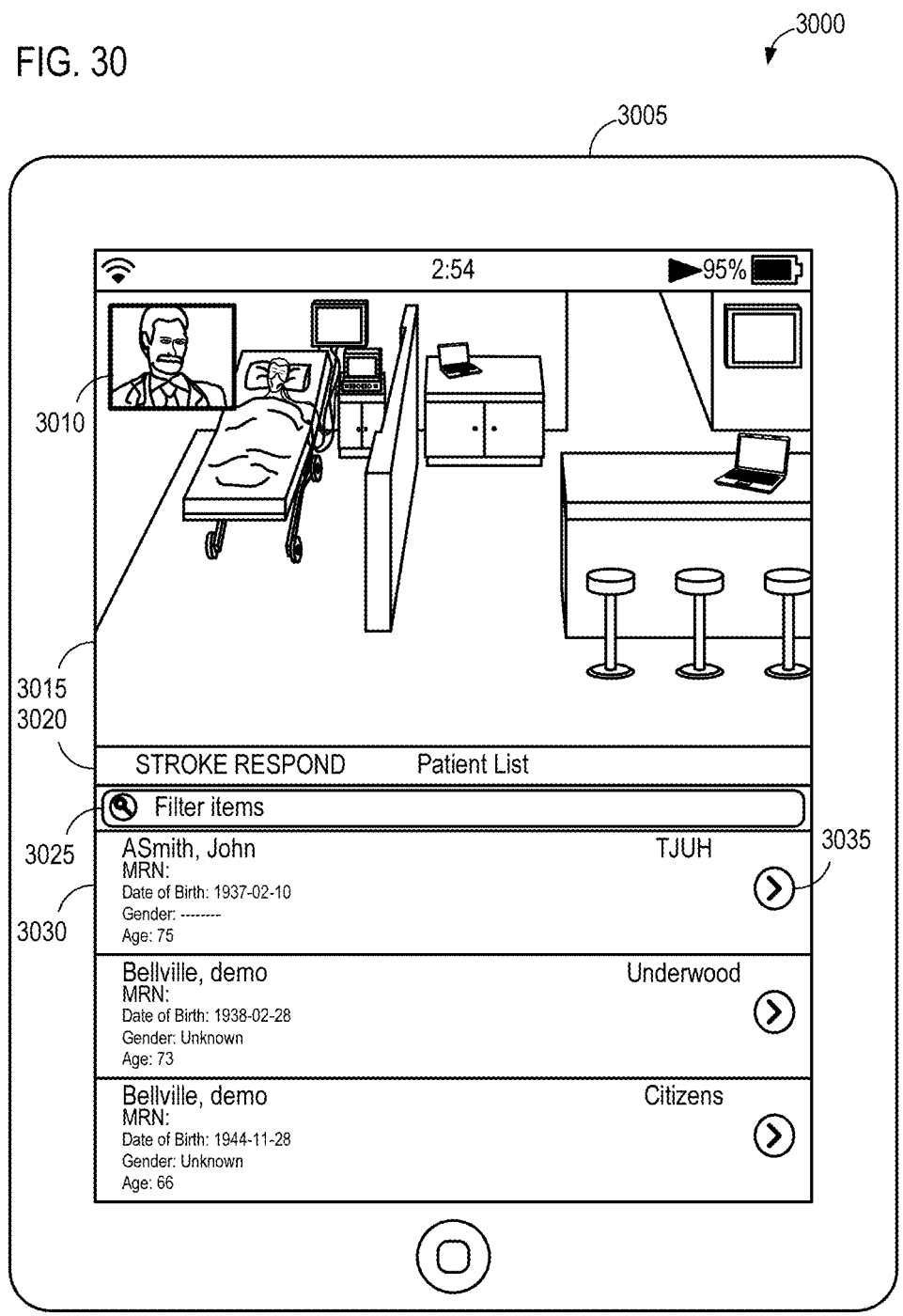
FIG. 30 illustrates a StrokeRESPOND application for accessing a telepresence device that may be a separate application or integrated within an RPI.

FIG. 30 illustrates an embodiment 3000 of a PED running an RPI configured to display a live video feed in an upper panel 3015 along with a current image window 3010. As illustrated, the RPI may incorporate sub-applications and/or provide access to related applications, such as a StrokeRESPOND application (in a lower panel 3020) configured to provide one or more functions and/or workflow processes associated with strokes. The StrokeRESPOND application may display various patient names 3030, which may be filterable, at 3025, and allow a user to select them, at 3035, in order to see more details. The RPI may allow for any number of sub-routines, sub-applications, and/or other applications to run within the RPI or be launched from the RPI. As other examples, the RPI may provide access to a dictionary, a medical text, an internet search engine, and/or any other external or integrated application.

In some embodiments, while an application is open in the lower panel 3020, the user may switch to viewing the application in full-screen mode by grabbing the upper part of the application window and dragging upward toward the upper panel 3010. The user may return to the two-pane view by dragging downward from the top of the upper panel 3010. The full-screen application view may include a picture-in-picture of the live video feed from the telepresence device so that the user may continue to monitor the remote environment. Some applications (and/or the RPI) may continue to run in the background, even when not displayed.

Figure 31:
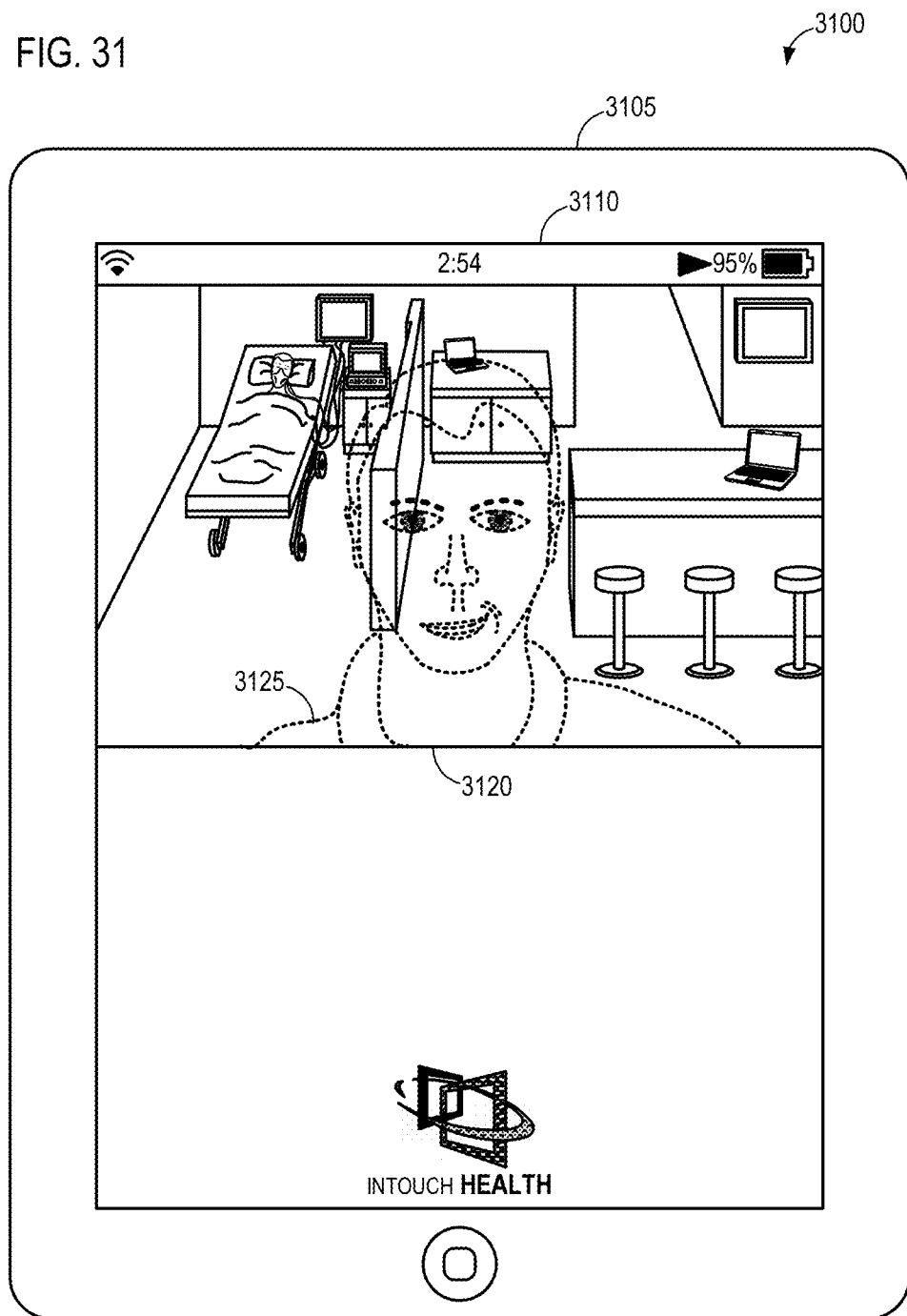
FIG. 31 illustrates a transparent user image overlaid on an image generated by a telepresence device.

FIG. 31 illustrates an embodiment 3100 of an RPI on a PED 3105, in which an image 3125 captured by a camera of the PED 3105 is displayed as a transparent image overlaid on a live video feed 3110 originating from a telepresence device. The transparent image 3125 may alternatively be displayed in a lower panel 3120.

Figure 32:
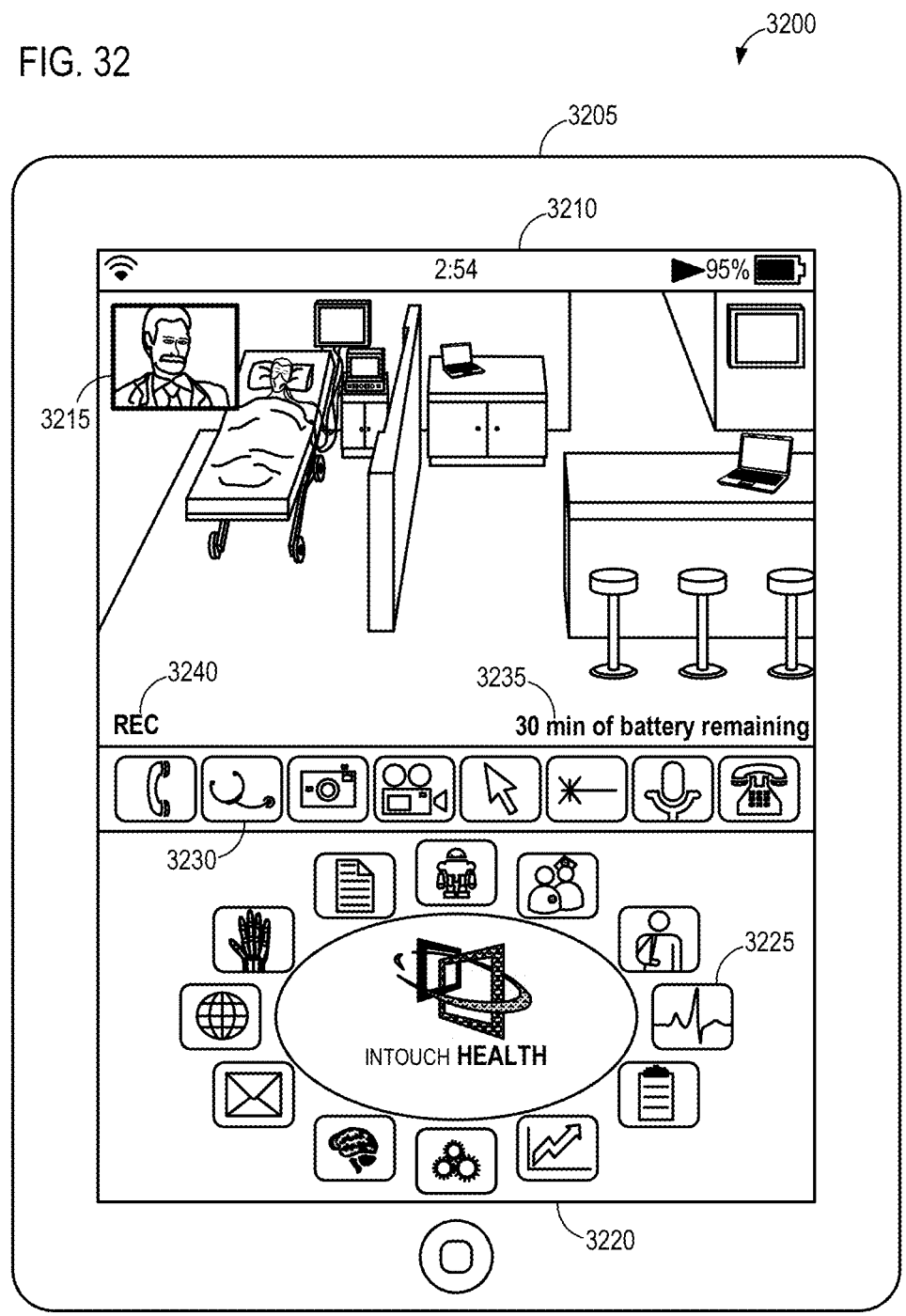
FIG. 32 illustrates a toolbar for managing modules and control operations available via an RPI, while simultaneously displaying a video feed from a telepresence device.

FIG. 32 illustrates an embodiment 3200 of an RPI on a PED 3205, including a toolbar 3225 in a lower panel 3220. The toolbar may provide quick access to any of a wide variety of settings and/or features of the RPI. A user may select an icon using any of a wide variety of methods depending on the PED. For instance, a user may touch an icon to select it. Settings and/or features of the RPI may be accessed simultaneously while a live video feed is shown in the upper panel 3210. A media management toolbar 3230 (selectively enabled) may allow for the video feed in upper panel 3210 to be recorded, at 3240. A notification 3235 may alert a user of the PED 3205 that the battery on the telepresence device is nearly depleted. As in previous embodiments, a window 3215 may display the image currently being captured by a camera on the PED 3205 or managing modules and control operations available via an RPI, while simultaneously displaying a video feed from a telepresence device.

According to various embodiments, the toolbar 3225 may provide access to a handset, a stethoscope, a camera, a video, a live cursor, a laser pointer, microphone settings, a map, navigational options, a disconnect button, and/or other features, options or settings. The toolbar 3225 may provide access to various other functions or applications, such as StrokeRESPOND, SureNotes, a media manager, patient data, lab results, image data, and/or team communication.

Figure 33:
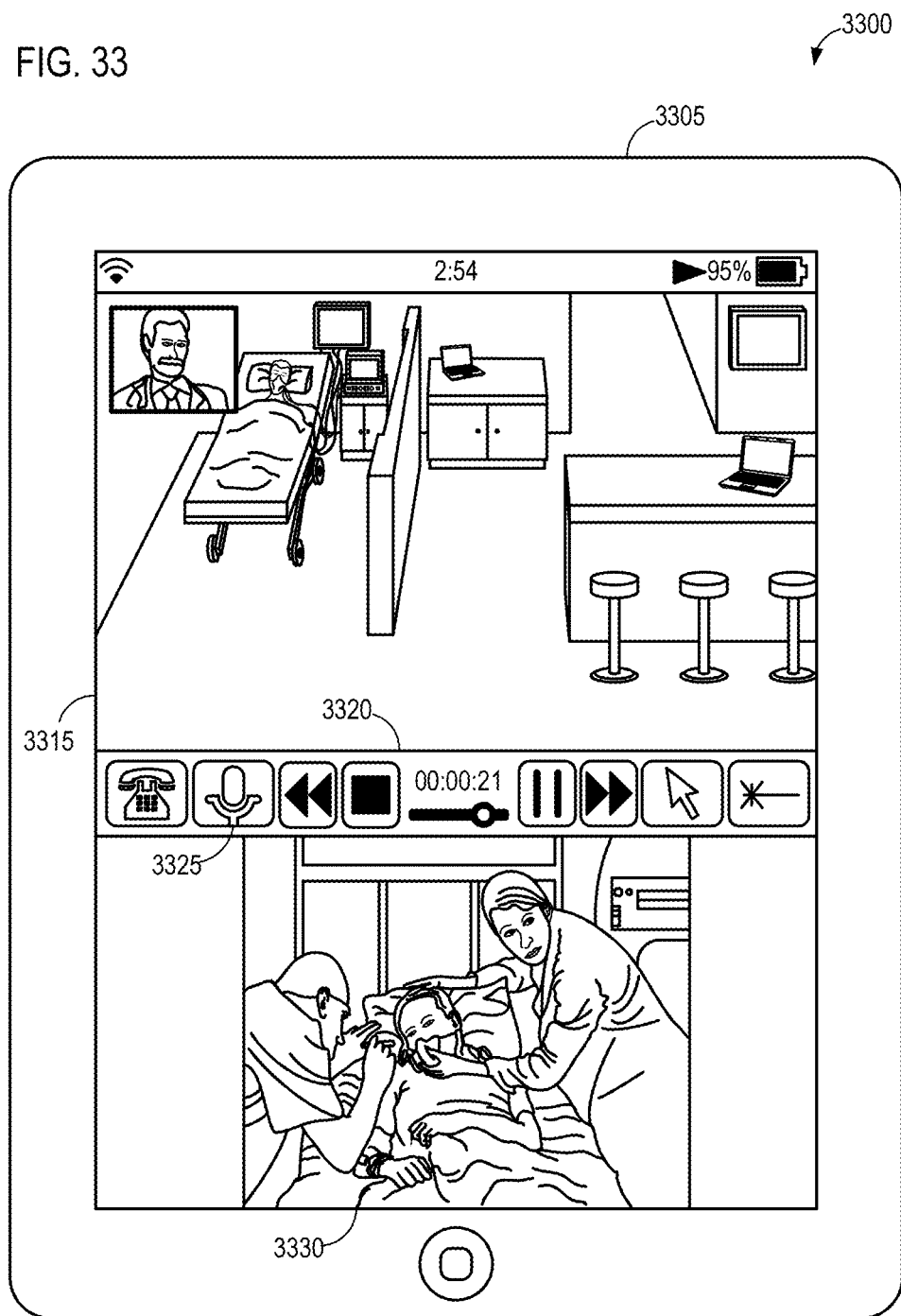
FIG. 33 illustrates a toolbar associated with a media management module of an RPI.

FIG. 33 illustrates an embodiment 3300 of an RPI on a PED 3305 that includes a media management toolbar 3325 associated with a media management window 3330 in a lower panel 3320 of the PED 3305. As illustrated, an upper panel 3315 may include a live video feed of a patient. The user of the RPI may access stored videos, images, audio, and/or telemetry data associated with the patient via the media management toolbar 3325.

Figure 34:
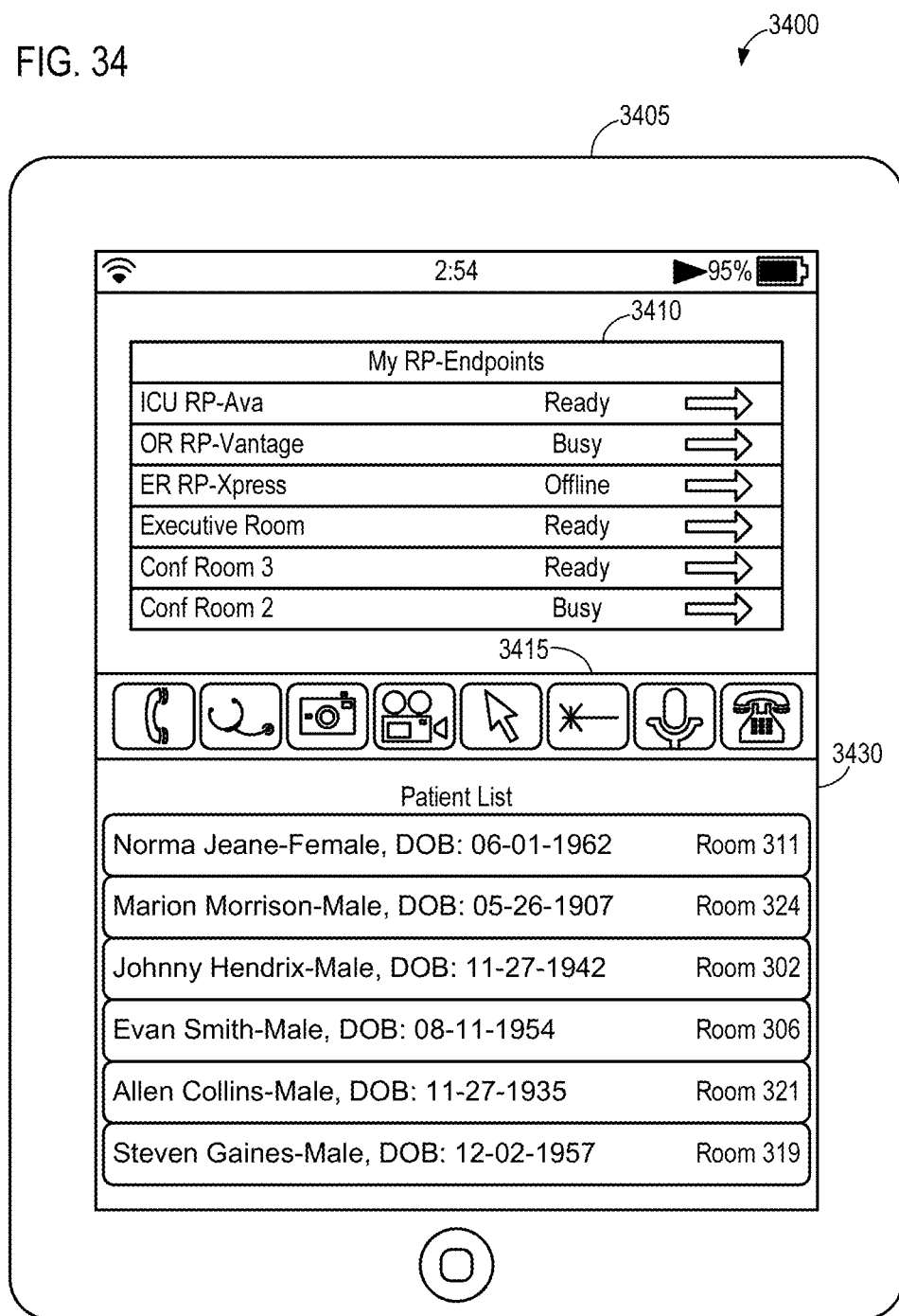
FIG. 34 illustrates a toolbar separating an endpoint list and a patient list in an RPI, allowing for quick user selection of various possible permutations.

FIG. 34 illustrates an embodiment 3400 of an RPI on a PED 3405 including a video window 3410 displaying a list of telepresence devices to which the user has access, a work space window 3430 displaying a list of patients, and a toolbar 3415 as a tool belt dividing the display. In various embodiments, the selection of a telepresence device via video window 3410 will display a live video feed from the selected telepresence device and initiate a communication session with the telepresence device to allow the user of the RPI on PED 3405 to control the telepresence device and/or join in a multi-user experience with the telepresence device. The selection of a patient via work space window 3430 may automatically select an associated telepresence device based on availability, proximity, and/or other preferences. Alternatively, the user of the RPI on the PED 3405 may additionally select a telepresence device. The selection of a patient via work space window 3430 may also direct a telepresence robot to navigate to the location of the patient.

Figure 35:
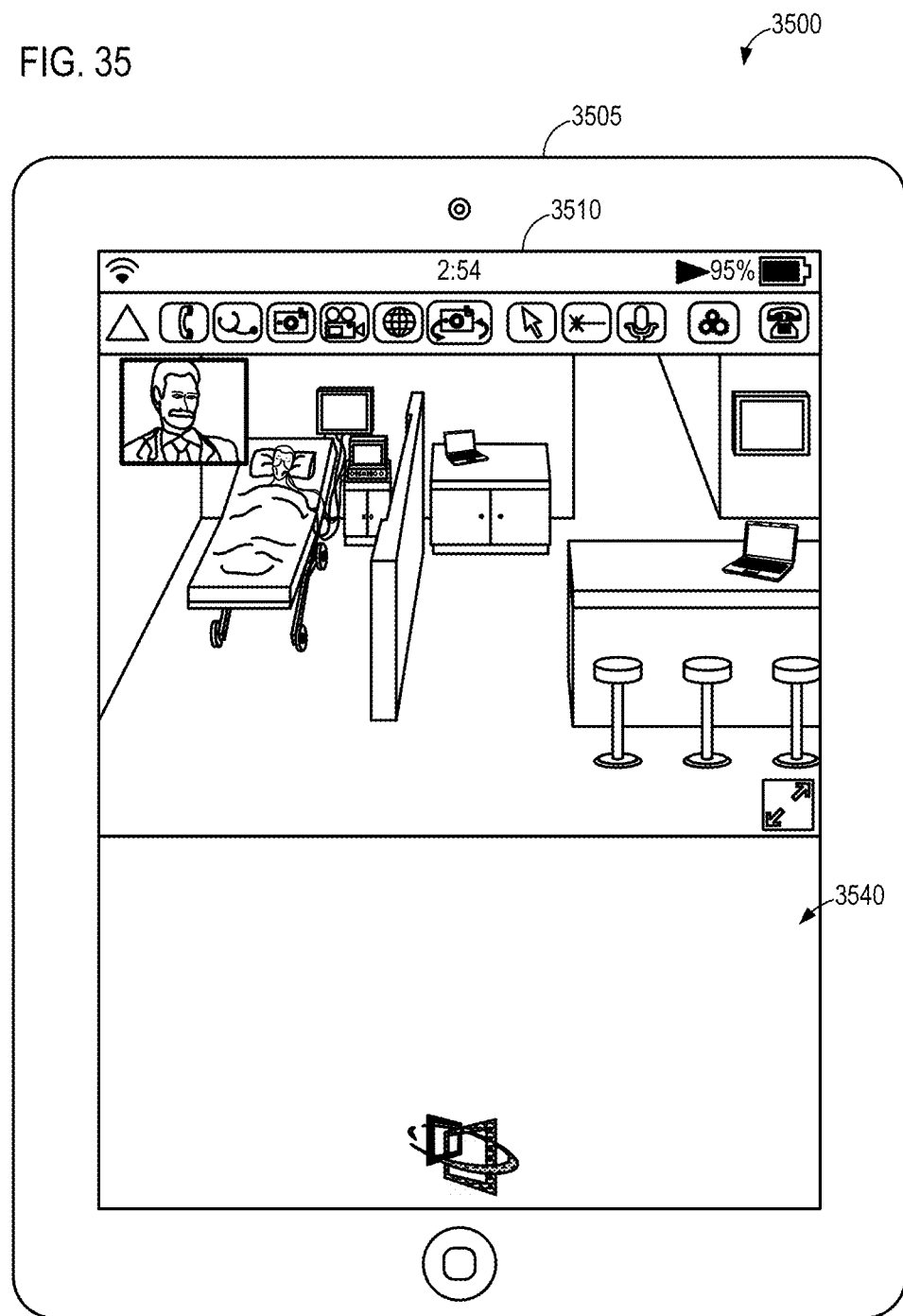
FIG. 35 illustrates a view of a touch pad control pane for navigating a telepresence device while displaying a video feed from a telepresence device in an upper window.

FIG. 35 illustrates an embodiment 3500 of an RPI on a PED 3505 including a touch pad control pane 3540 for navigating a telepresence device while displaying a video feed from a telepresence device in an upper panel 3510. According to various embodiments, a one finger tap in the upper panel 3510 may be used to control the direction in which a head portion of a telepresence device is oriented. A single finger press and drag may draw a click-to-zoom box. Other touch controls, such as pinch to zoom, mouse-based driving, and/or swiping to move the telepresence device may also be available in upper panel 3510. In some embodiments, a four way controller (illustrated in FIGS. 27B-27H) may be overlaid within the live video feed in the upper panel 3510. The touch pad control pane 3540 may incorporate various touch controls. For example, a user may swipe left to gain access to local controls/settings of the PED 3505, swipe right to access controls/settings from the telepresence device, swipe down to access a toolbar, and use multiple fingers to drive the telepresence device, such as by defining a vector with a magnitude and direction.

Figure 36:
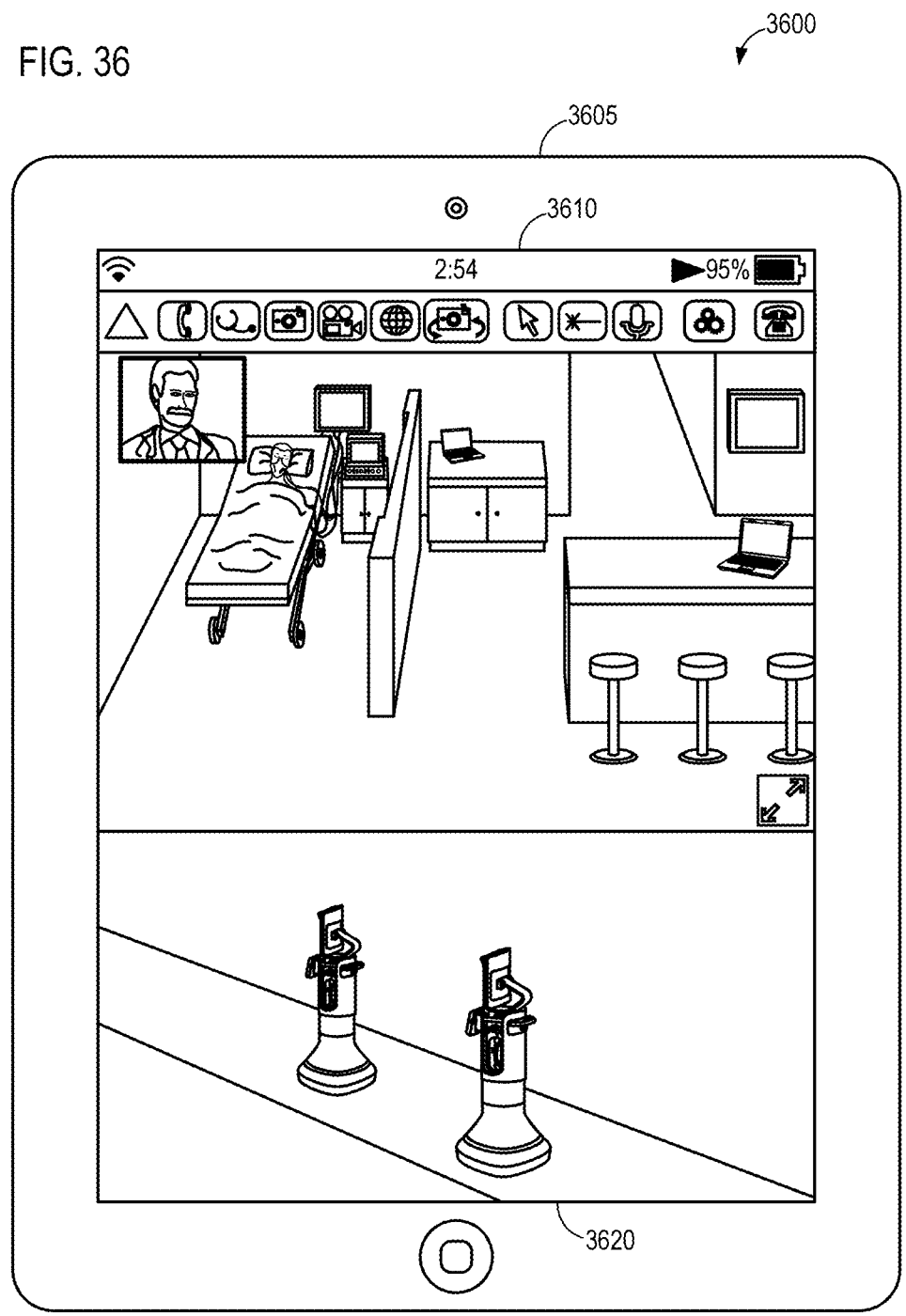
FIG. 36 illustrates an avatar display of telepresence devices in a lower window and a video feed from a telepresence device in an upper window.

FIG. 36 illustrates an embodiment 3600 of an RPI on a PED 3605, including an avatar display of telepresence devices in a lower panel 3620 and a video feed from a telepresence device in an upper panel 3610. In various embodiments, tapping a camera icon may capture an image. The image may then appear within a media manager in the lower panel 3620. Drag and drop availability may be available in order for the user to customize the telepresence device, such as by adding avatars or special effects to the video feed and/or images.

Figure 37:
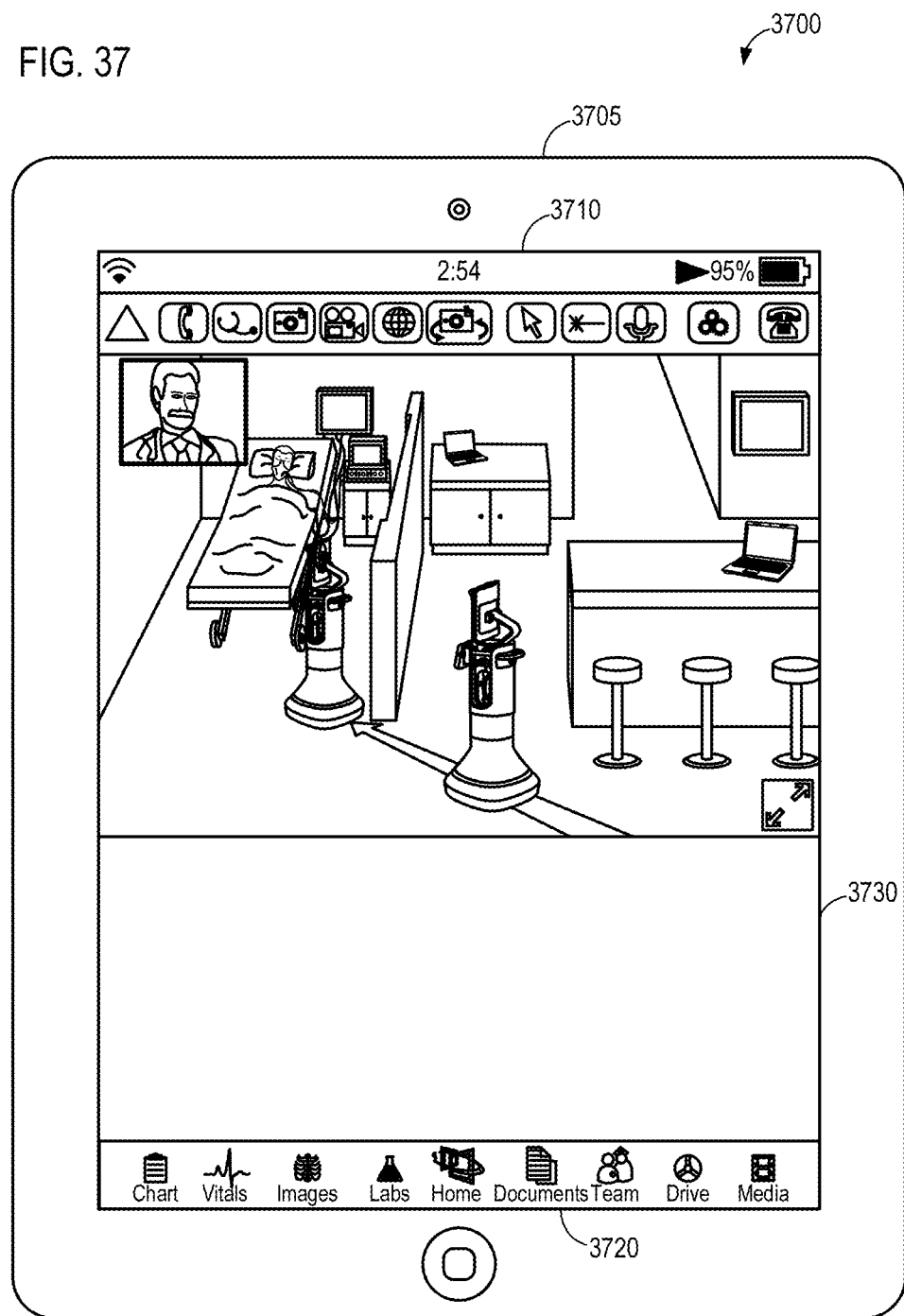
FIG. 37 illustrates a visualization of a telepresence device overlaid on a video feed from a telepresence device that may be useful for navigation of the telepresence device.

FIG. 37 illustrates an embodiment 3700 of an RPI on a PED 3705 including a visualization of a telepresence device overlaid on a video feed from a telepresence device in an upper panel 3710. As illustrated, the user may place the chess-piece telepresence devices within the video feed in the upper panel 3710 in order to control movement of the actual telepresence device. A lower panel 3730 may allow a user to provide other navigational inputs as well. A lower toolbar 3720 may provide access to various settings and/or function to the RPI.

Figure 38:
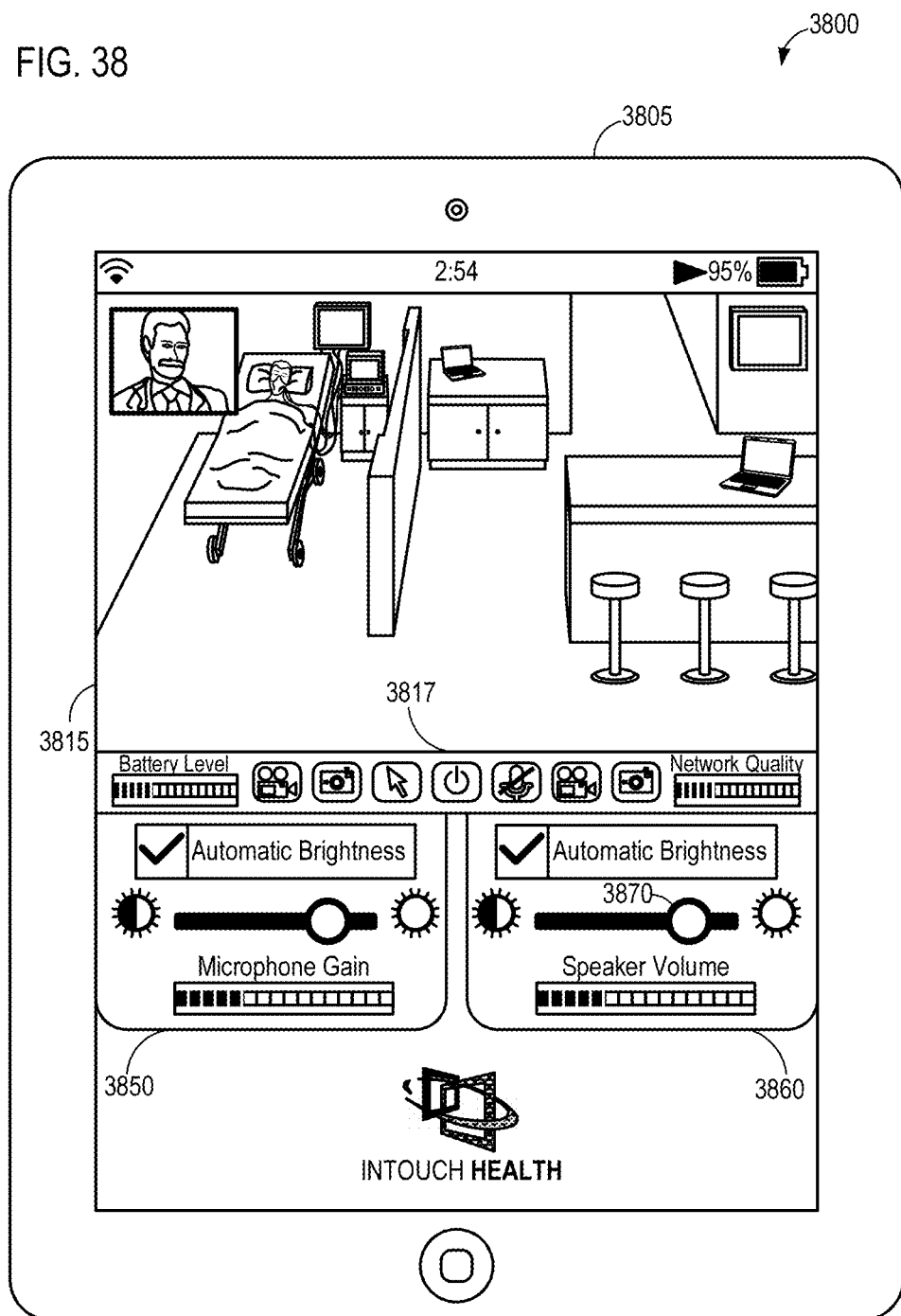
FIG. 38 illustrates a toolbar of an RPI associated with a settings manager for managing settings on a local PED and/or a telepresence device.

FIG. 38 illustrates another embodiment 3800 of an RPI on a PED 3805 including a live video feed in an upper panel 3815, a toolbar belt including various media management icons 3817, and settings manager toolbars 3850 and 3860 for the PED 3805 and a telepresence device, respectively.

Figure 39:
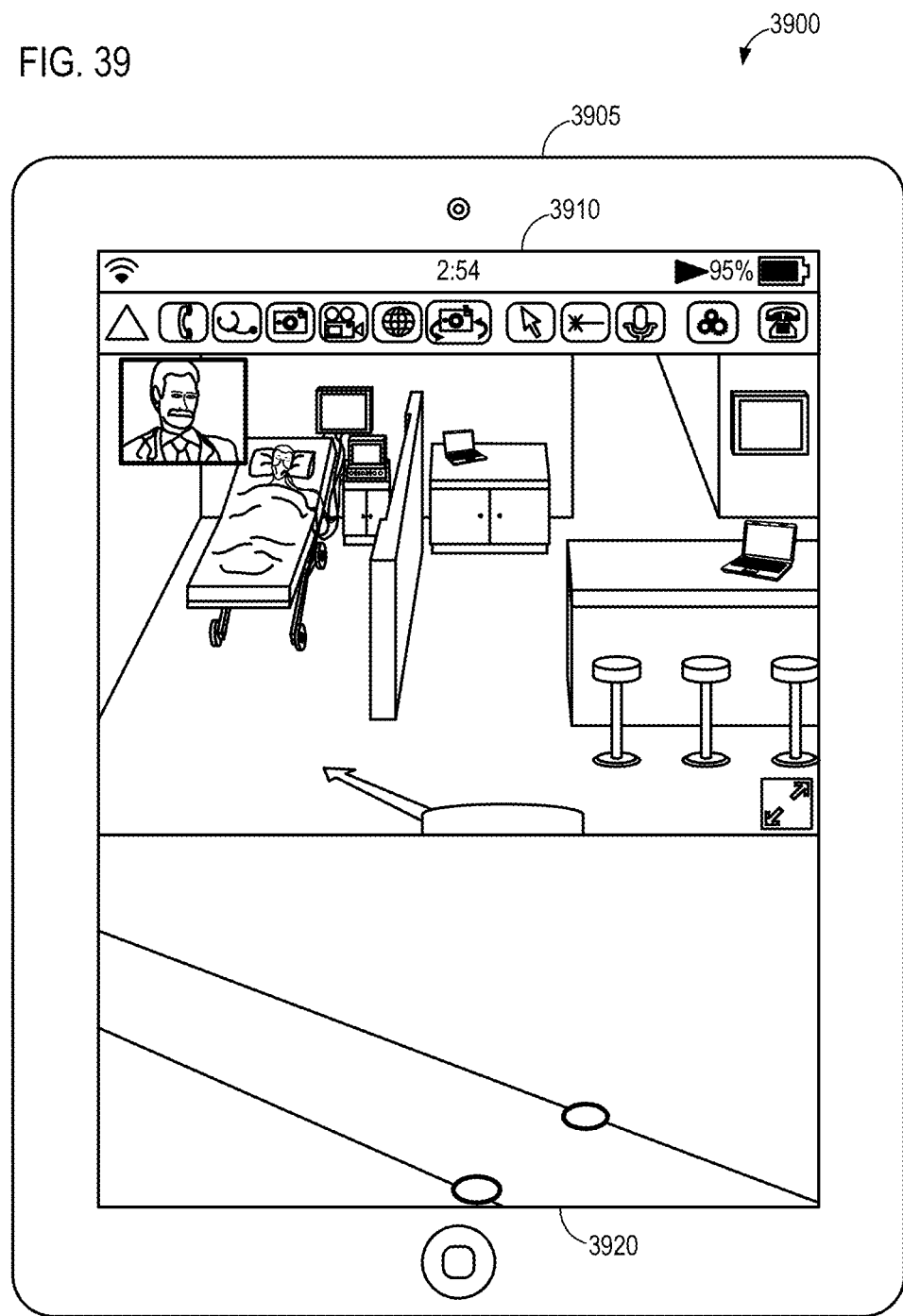
FIG. 39 illustrates a navigational mode including a landing strip navigational panel allowing a user to specify a direction of a telepresence device.

FIG. 39 illustrates an embodiment 3900 of an RPI on a PED 3905 that includes a landing strip navigational panel 3920. A user may provide an intended navigation path that can be displayed on the upper panel 3910 and/or the lower panel 3920. The landing strip navigational panel 3920 may be used to display an intended navigational path, a directed navigational path (i.e. a path provided by a user to direct the telepresence device), or a current navigation path on the upper panel 3910 as a vector and/or within the lower panel 3920 as a vector and/or as an avatar or rendered image of the telepresence device.

Figure 40:
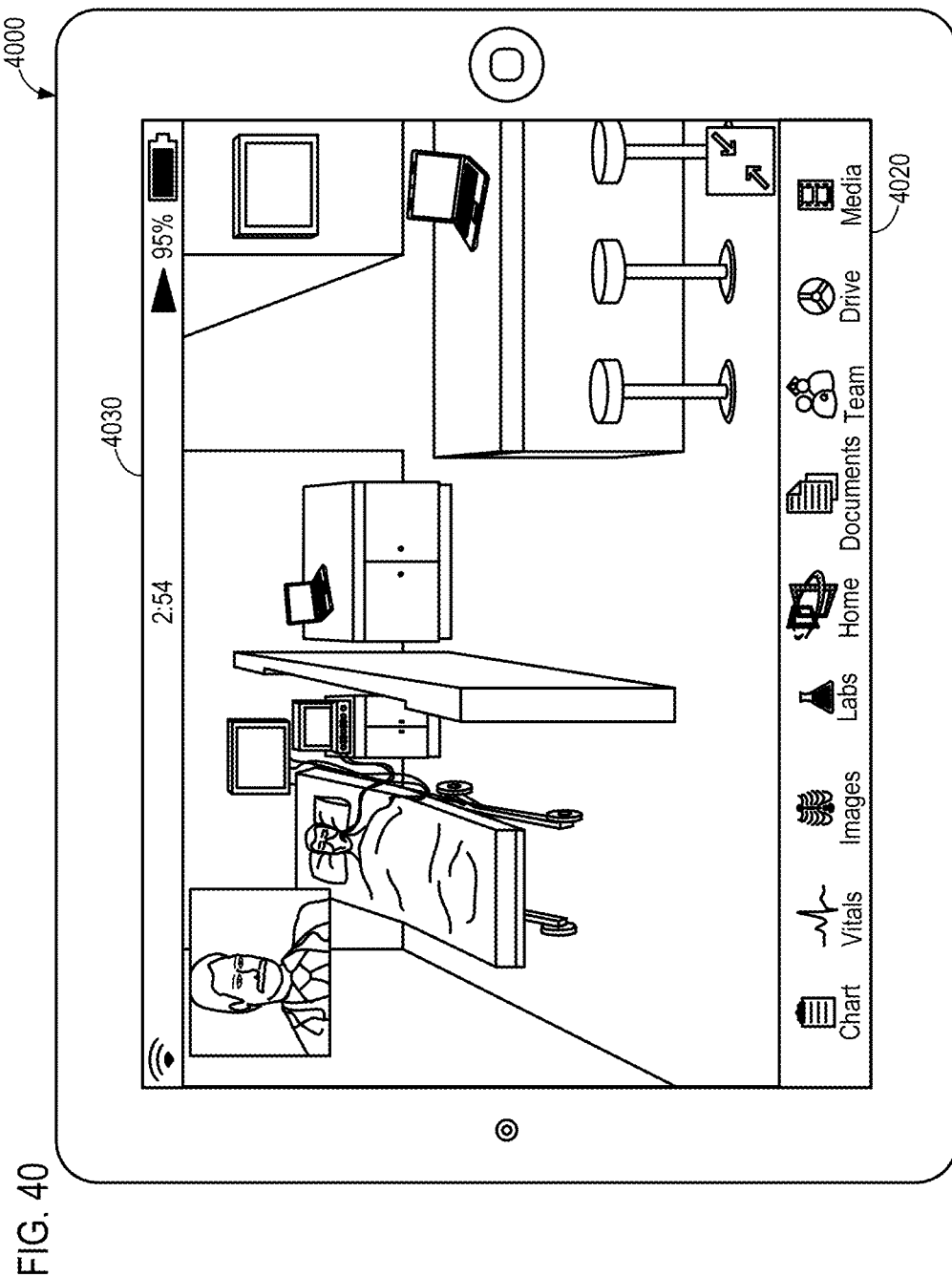
FIG. 40 illustrates a full-screen video feed from a telepresence device, including an overlaid toolbar.

FIG. 40 illustrates an embodiment of an RPI on a PED 4000 including a landscape orientation of a full-screen video feed 4030 from a telepresence device. In addition, a toolbar may be overlaid and/or included in a separate lower panel 4020.

Figure 41:
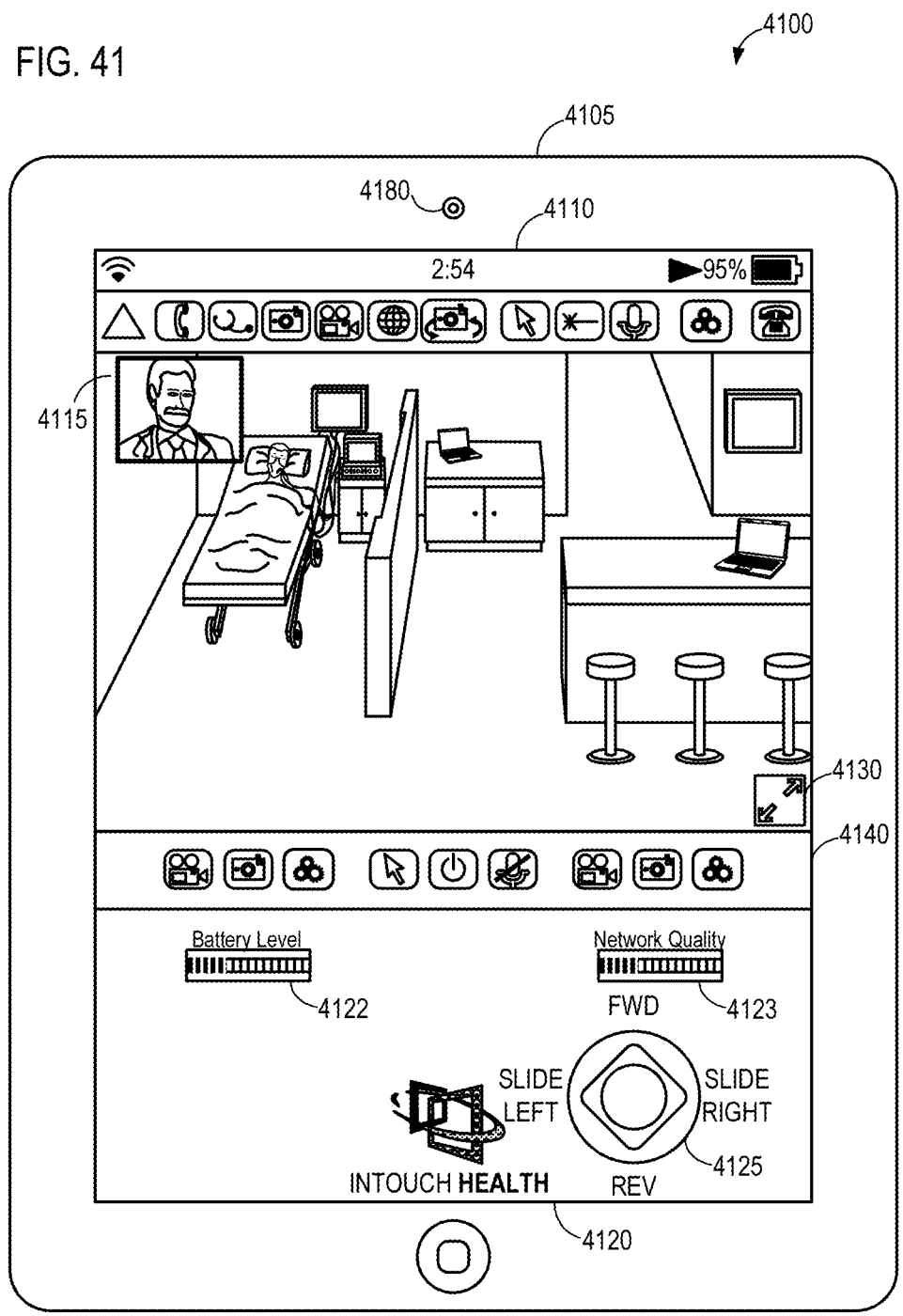
FIG. 41 illustrates a joystick-style control on a touch interface of a PED for controlling a telepresence device via an RPI.

FIG. 41 illustrates an embodiment 4100 of an RPI on a PED 4105 including a joystick-style control 4125 on a touch interface of a lower panel 4120 of the PED 4105. The lower panel 4120 may also include information icons relating to battery level 4122 and/or network quality 4123. A toolbar 4140 may provide access to various settings, features, and/or controls. A full-screen icon 4130 may allow the live video feed in the upper panel 4110 to be maximized to a full-screen mode. A window 4115 may be overlaid in the upper panel 4110 to show the current image captured by a camera 4180 of the PED 4105.

Figure 42:
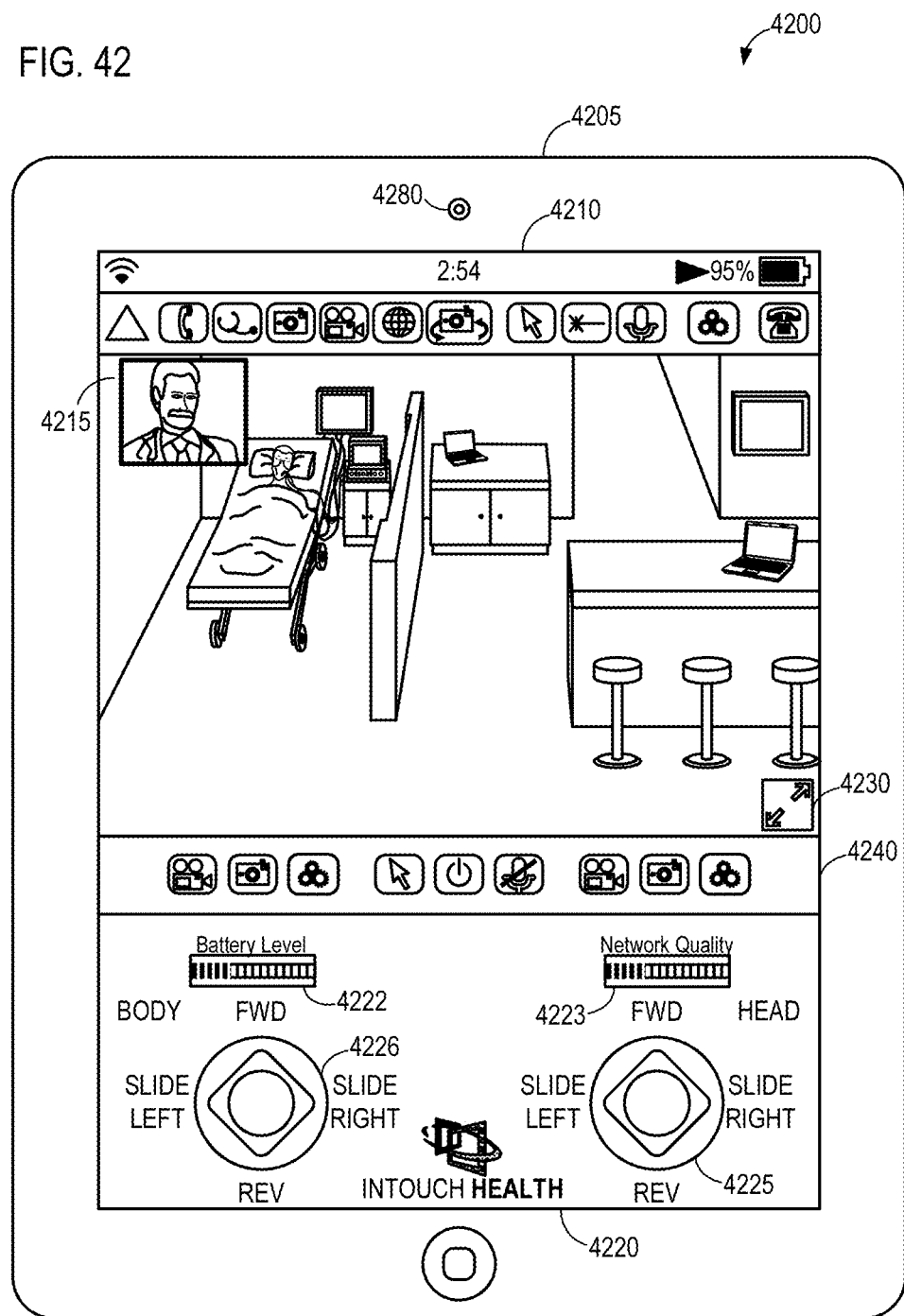
FIG. 42 illustrates a dual joystick-style control on a touch interface of a PED for controlling a telepresence device via an RPI.

FIG. 42 illustrates an embodiment 4200 of an RPI on a PED 4205 including dual joystick-style controls 4225 and 4226 on a touch interface of a lower panel 4220 of the PED 4205. The lower panel 4220 may also include information icons relating to battery level 4222 and/or network quality 4223. A toolbar 4240 may provide access to various settings, features, and/or controls. A full-screen icon 4230 may allow the live video feed in upper panel 4210 to be maximized to a full-screen mode. A window 4215 may be overlaid in the upper panel 4210 to show the current image captured by a camera 4280 of the PED 4205.

In the illustrated embodiment, the left joystick 4226 may be configured to control movement of the base or body of the telepresence device. The right joystick 4225 may be configured to control movement of a head or upper portion of the telepresence device. The portion of the telepresence device controlled by each joystick 4225 and 4226 may be user-selectable and/or reversed.

Figure 43:
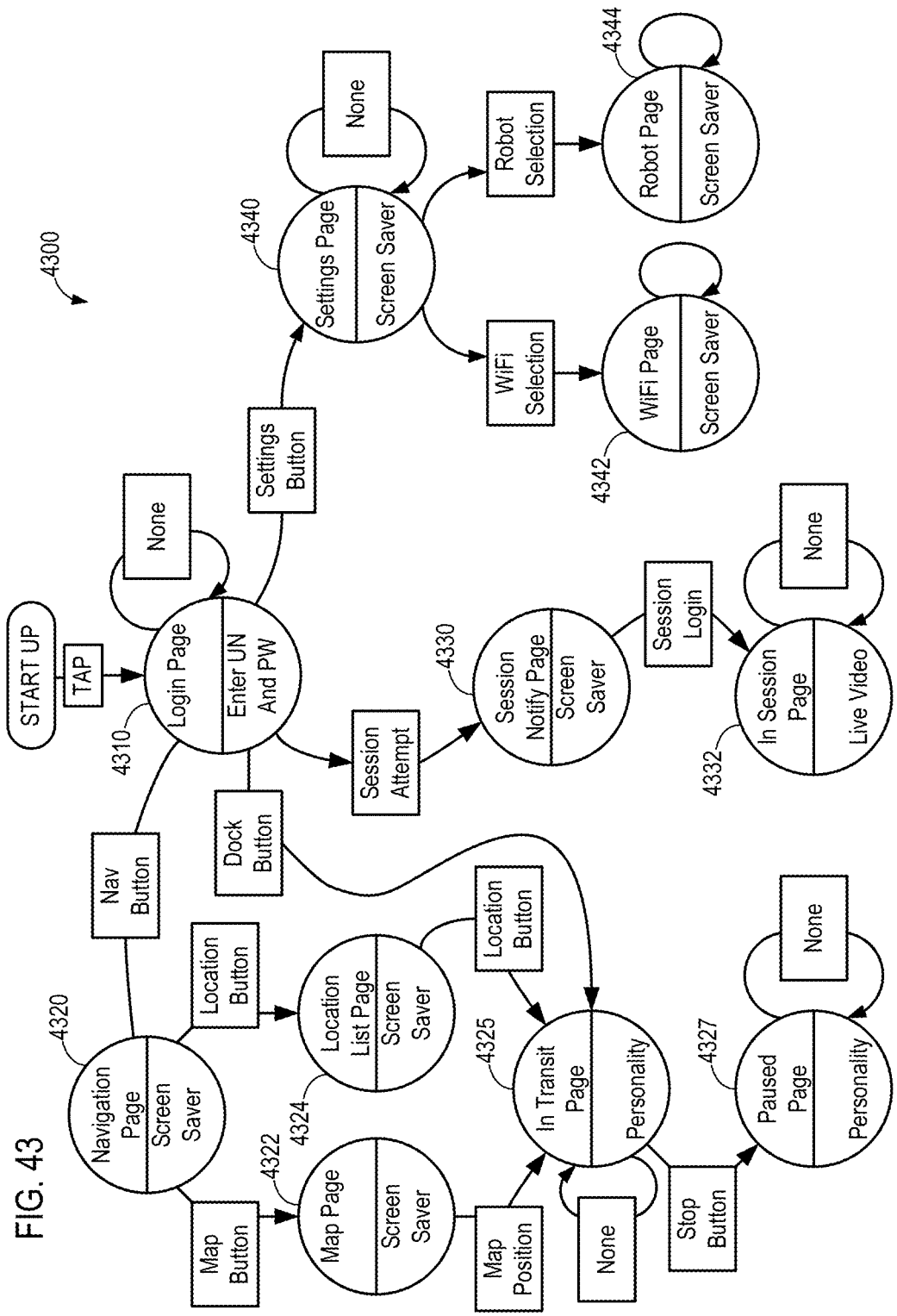
FIG. 43 illustrates a state diagram for an RPI for use on a PED.

FIG. 43 illustrates a state diagram 4300 for an RPI for use on a PED. As illustrated, following startup, a login page 4310 may be displayed. After a username and password are entered, a session notify page 4330 may be displayed indicating the network and communication status. A successful login may result in an in-session page being displayed 4332 with a live video feed. A dock button may be selected, causing the telepresence device to display an in-transit page 4325 while it navigates to a docking station. A stop button may cause the page to pause 4327.

From the login page, potentially after successfully logging in, a navigation button may display a navigation page 4320. The navigation page 4320 may allow a user to select between various navigation modes, such as a map button to result in a map page 4322, or a location button to display a list of locations 4324. Again, once a destination is selected, the in-transit page 4325 may be displayed as the telepresence device navigates to the selected location.

A settings page 4340 may be displayed allowing a user to select from any number of settings. For example, a WiFi selection may result in a WiFi page 4342 being displayed. A robot selection may result in a robot page 4344 being displayed. The state diagram 4300 illustrated in FIG. 43 is a simplified state diagram and intentionally omits numerous possible states and connections between states for clarity. Each and every panel, icon, setting, application, option, tab, selection, input, and the like described herein may be represented as a separate state, entry action, transition condition, transition, exit action, and/or other component of a complex state diagram. As will be appreciated by one of skill in the art, each of the various aspects, functions, operations, control panels, icons, objects, buttons, display panels, display windows, etc., described herein may be described and/or implemented in terms of software, hardware, and/or firmware and could potentially be described as a complex state machine.

Figure 44:
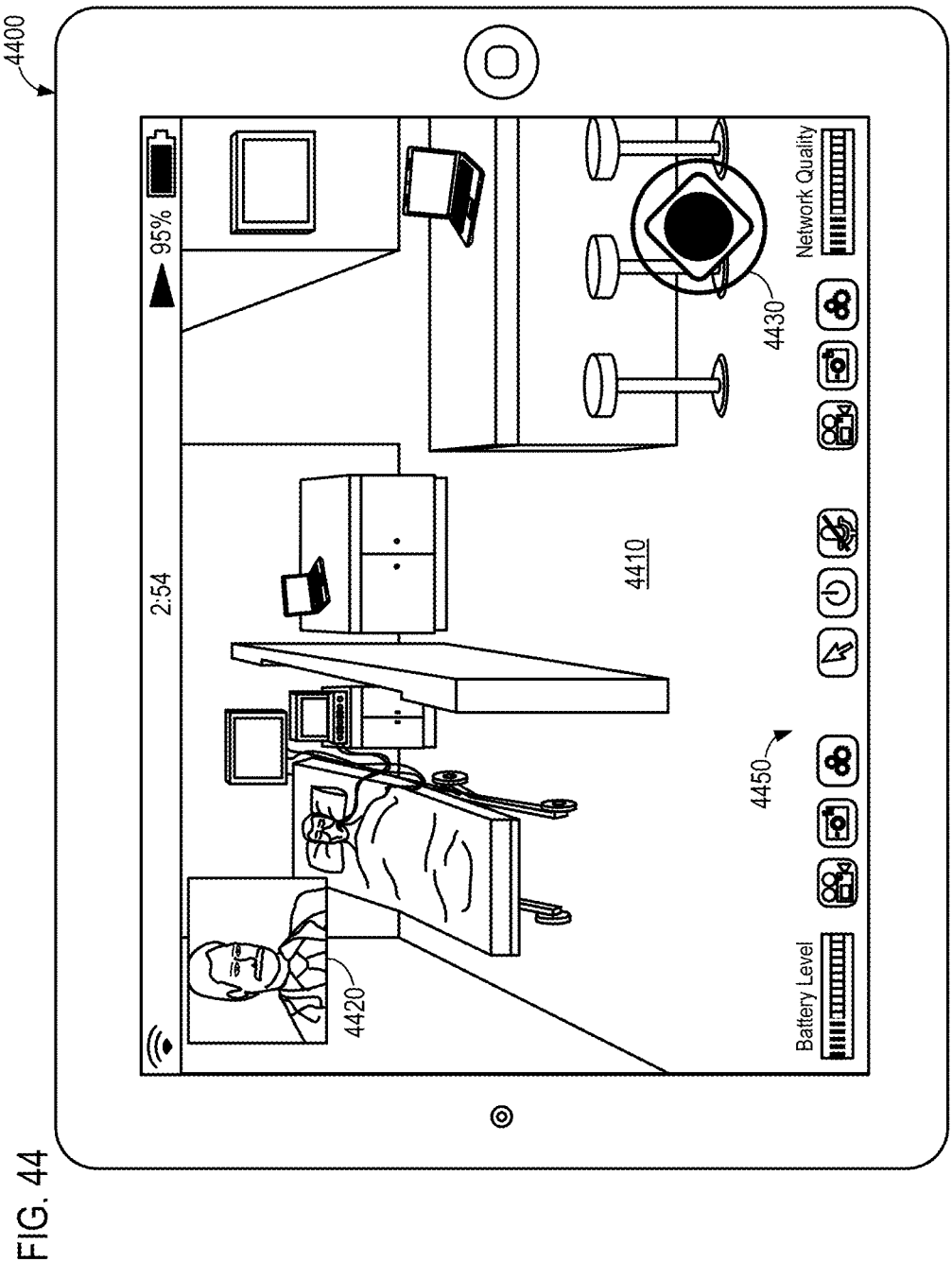
FIG. 44 illustrates a full-screen video feed from a telepresence device, including an overlaid toolbar and joystick control.

FIG. 44 illustrates an embodiment of an RPI on a PED 4400 including a full-screen video feed 4410 from a telepresence device. A toolbar 4450 and a navigational joystick 4430 are overlaid on the full-screen video feed 4410. A user may touch, click, or otherwise manipulate the joystick in order to navigate the telepresence device. A dual joystick overlay may be employed to provide navigational control over a head portion of a telepresence device. In some embodiments, clicking a location within the live video feed 4410 may control the head movement of the telepresence device while the joystick 4430 is intended to control the body movement of the telepresence device. Similarly, a mouse-based driving interface (illustrated in FIGS. 27B-27H) may be overlaid on the full-screen video feed 4410 instead of or in addition to the joystick 4430.

Figure 45:
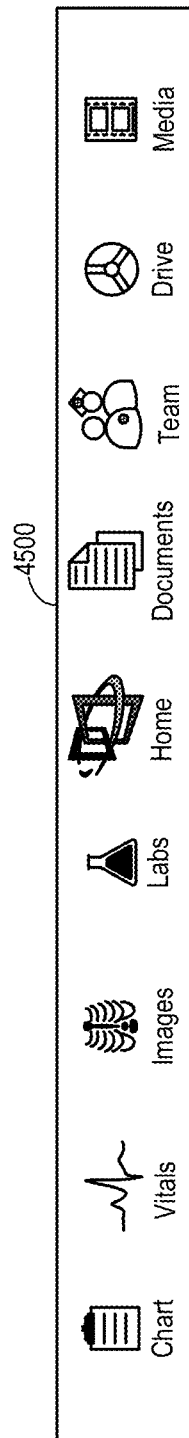
FIG. 45 illustrates an exemplary toolbar of icons that may be overlaid within an RPI.

FIG. 45 illustrates an exemplary toolbar 4500 of icons that may be overlaid within a page of an RPI and/or inserted as a separate panel within a page of an RPI. The icons within toolbar 4500 may provide access to charts, vitals, telemetry data, images, lab results, a home page of the RPI, documents, notes, associated healthcare practitioners, navigation options and features, multimedia control panels, and the like. Each page with the RPI may include context-based toolbars and/or general toolbars. The toolbar 4500 may be positioned at a bottom, top, edge, and/or other location with respect to the RPI or a pane or panel within the RPI. In some embodiments, the toolbar 4500 may be configured to vanish and selectively reappear, such as, for example, upon a mouseover, swipe, or other action.

Figure 46:
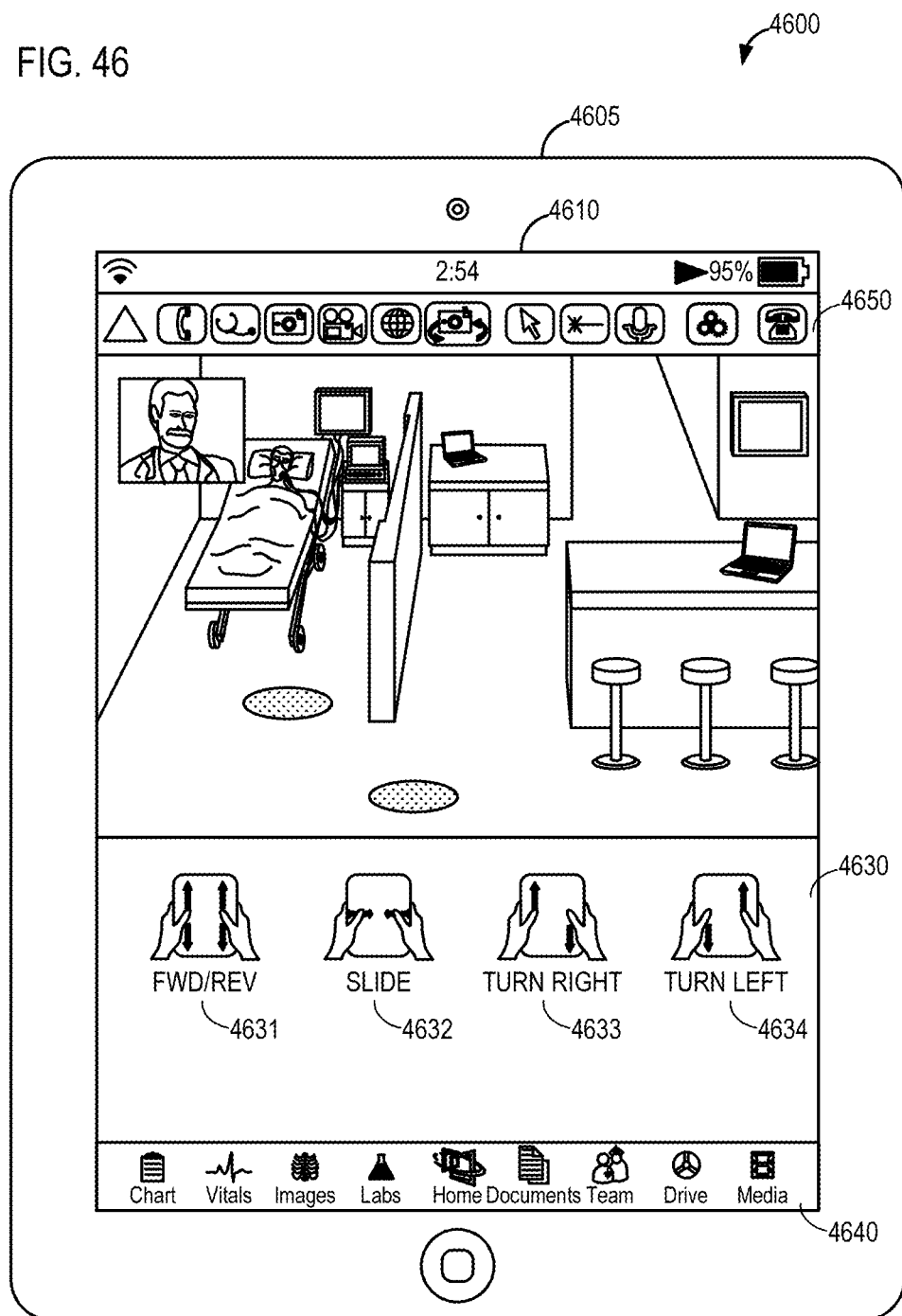
FIG. 46 illustrates an overlaid instructional panel associated with driving a telepresence device via an RPI on a PED.

FIG. 46 illustrates an embodiment 4600 of an RPI on a PED 4605 including an overlaid instructional panel 4630 describing how a user may manually drive a telepresence device. As in previous embodiments, an upper panel 4610 may include a live video feed from the telepresence device. A toolbar 4650 may provide access to various settings, controls, and/or functions. For example, the toolbar 4650 may provide access to a headset, stethoscope, camera, video, navigation, local camera, point, laser, mute, settings for local and remote devices, and/or a disconnect (end) button.

The instructional panel 4630 may provide instructions for finger swipes to move the telepresence device forward and reverse 4631, slide the telepresence device side to side 4632, rotate the telepresence device to the right 4633, and rotate the telepresence device to the left 4634. Separate control of a head portion of the telepresence device may be available using multiple fingers, using a toggle button (software or hardware), or by tapping within the live video feed 4610. A lower toolbar 4640 may provide access to various other functions, features, and/or settings of the RPI, such as those described herein and especially in conjunction with FIG. 45. In some embodiments, the RPI may include instructional or demonstrational videos for any of the various embodiments or functions described herein.

Figure 47:
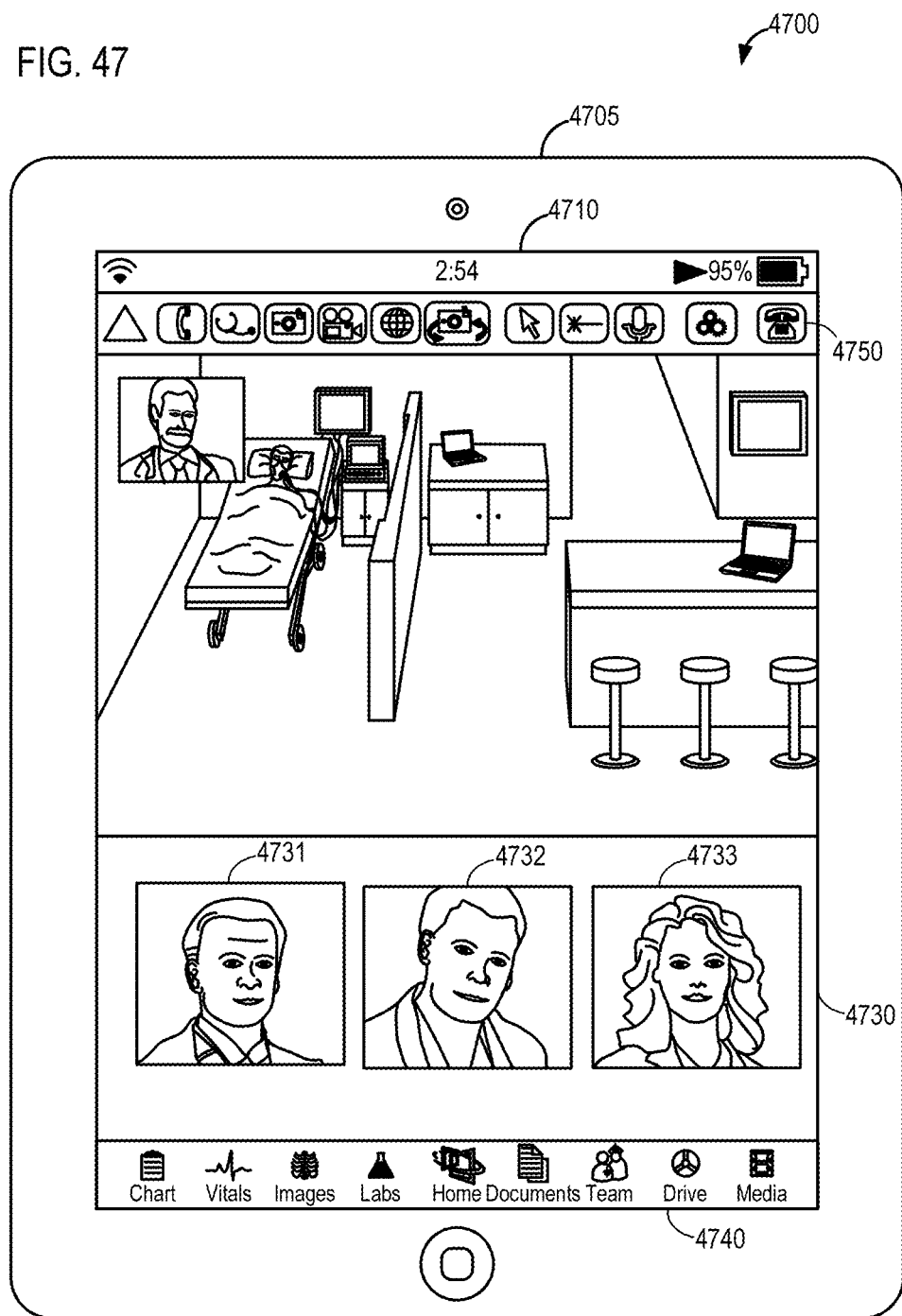
FIG. 47 illustrates a multi-participant telepresence session conducted via an RPI on a PED.

FIG. 47 illustrates an embodiment 4700 of an RPI on a PED 4705 during a multi-participant telepresence session. As illustrated, a live video feed of a patient may be displayed in an upper panel 4710 of the PED 4705. A toolbar 4750 (and/or 4740) may provide access to various related functions, settings, and/or controls. A lower panel 4730 may include video feeds 4731, 4732, and 4733 from each of three participants in the multi-participant telepresence session. Each of the three participants may be using an RPI on a PED and see a similar image of the video feed of the patient in the upper panel 4710. Any number of participants may participate. In some embodiments, each participant may be able to control the telepresence device. In other embodiments, only one, or only a select few, of the participants may have control of the telepresence device.

Figure 48:
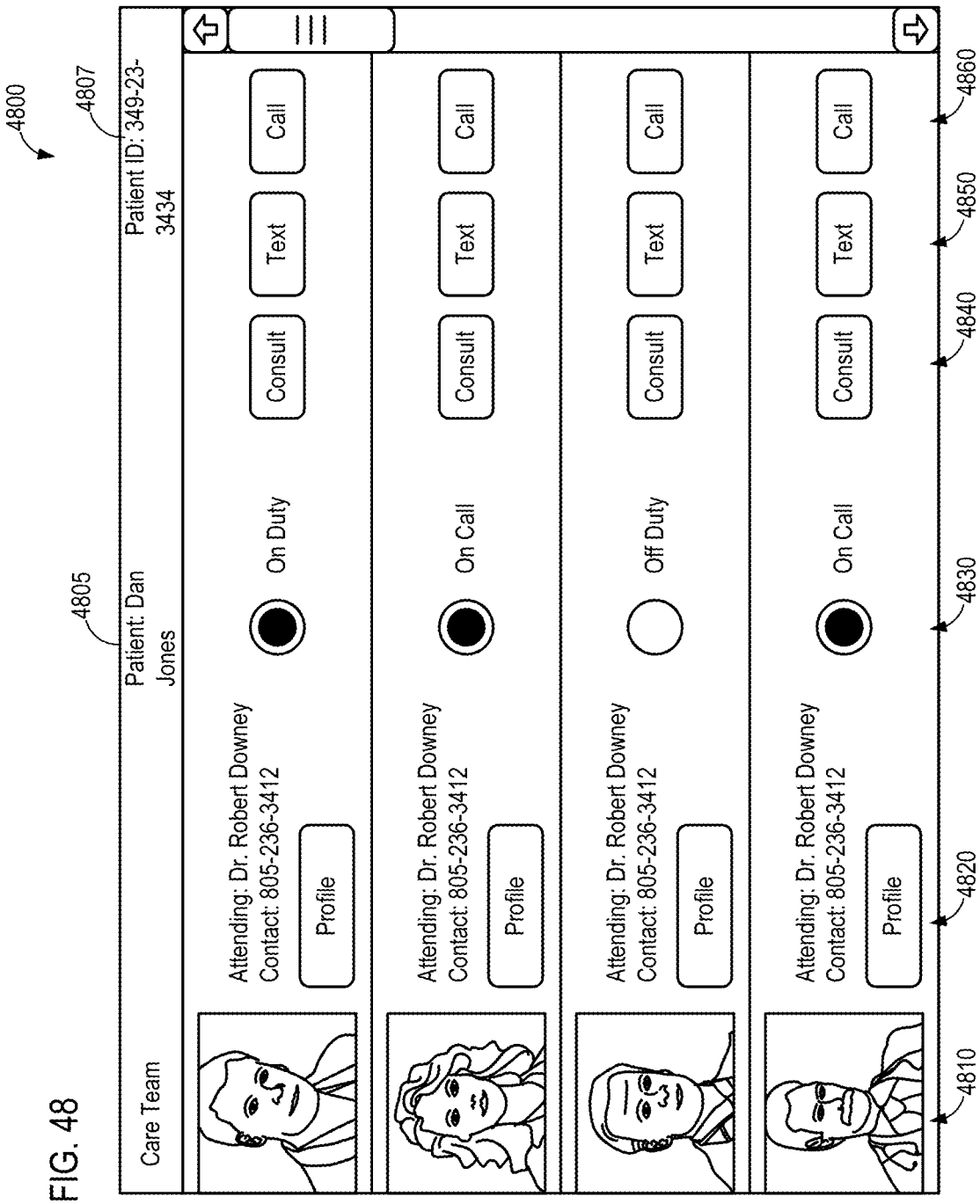
FIG. 48 illustrates a window accessible via an RPI on a PED providing access to a care team of a particular patient.

FIG. 48 illustrates a window or panel 4800 accessible via an RPI on a PED providing access to a care team of a particular patient. The care team panel 4800 may be presented in a full-screen mode and/or as a panel within a display of multiple panels, such as illustrated in FIG. 17. The care team panel 4800 may identify the relevant patient by name 4805 and/or an identification number 4807. The care team panel 4800 may include a column of healthcare practitioners 4810 associated with the patient 4805. A column of healthcare practitioner data 4820 may describe each of the healthcare practitioners 4810 associated with the patient 4805. Whether each healthcare practitioner 4810 is on duty or off duty may be displayed in a third column 4830. A user may also select icons via the RPI to consult 4840, text (e.g., an SMS or email) 4850, and/or call 4860 the associated healthcare practitioner 4810. In various embodiments, the RPI interface may utilize inputs provided via panel 4800 to perform one or more functions via the telepresence device and/or a related telepresence system.

Figure 49:
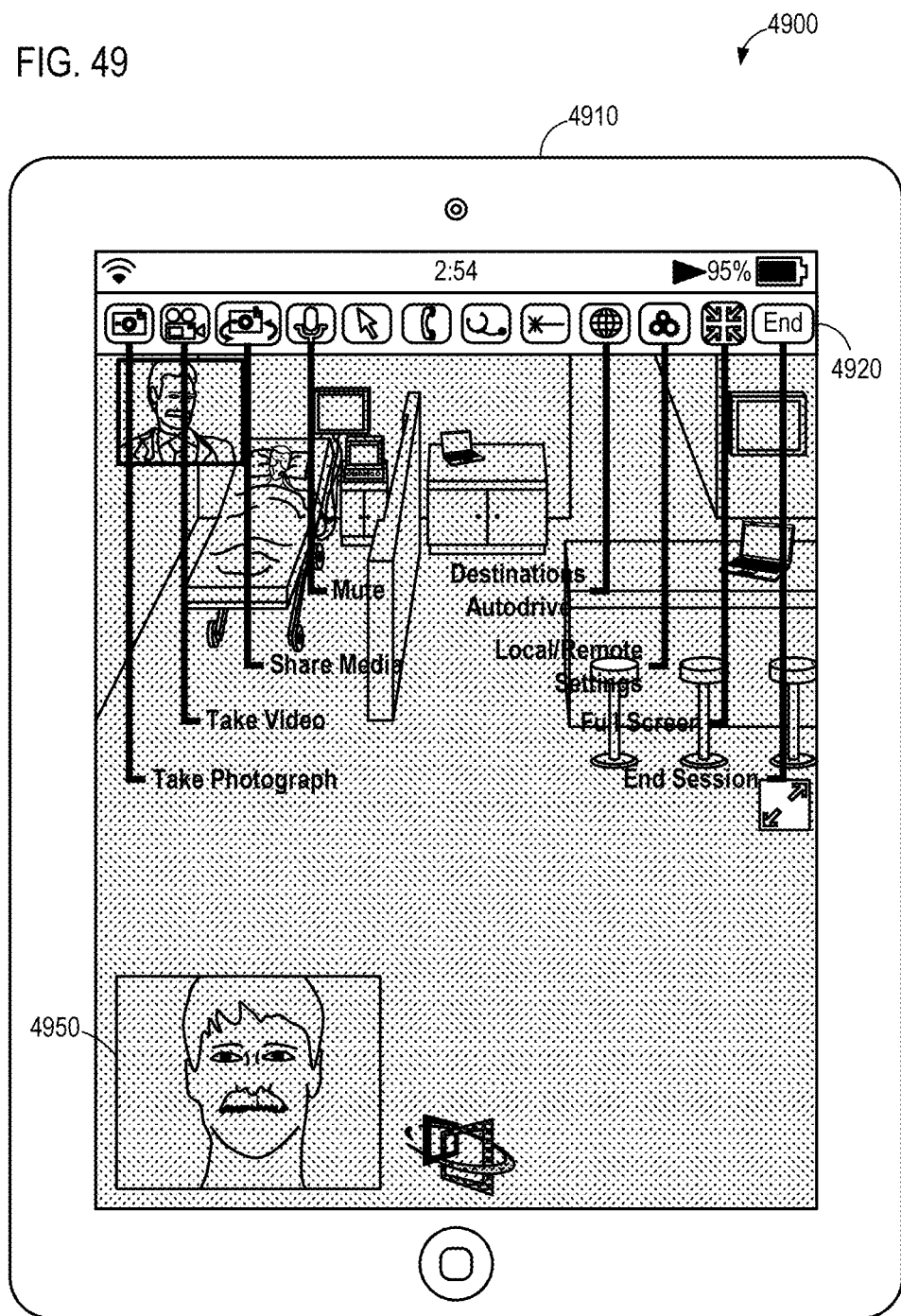
FIG. 49 illustrates an exemplary overlay help screen accessible within the RPI on a PED to provide instructions regarding available functions on any given screen.

FIG. 49 illustrates an exemplary overlay help screen 4900 accessible within the RPI on a PED to provide instructions regarding available functions on any given screen. In the illustrated example, a user may have selected a "help" icon or be in a training mode in order to be presented with instruction on how to use a particular interface or toolbar within a screen of the RPI. In the illustrated embodiment, a window 4950 may display what is currently being captured by a camera of the PED and displayed remotely on a display interface of a telepresence device. A full-screen image of a live video feed 4910 from a telepresence device may be displayed. In addition, a toolbar 4920 may be displayed on a top edge (or other location) of the full-screen display of the live video feed 4910. The toolbar may be pulled down from a hidden state and/or vanish and reappear, as described herein.

During training, initial use, or after indicating help is needed, the live video feed 4910 and/or the window 4950 may be dimmed and/or otherwise less obtrusive. A help screen overlay may provide instructions and/or guidance with how-to toolbars and/or other interface options. As illustrated in FIG. 49, the overlay may comprise text descriptions of the toolbar icons connected by lines to each icon. In some embodiments, instructions and/or guidance for camera controls and/or driving controls for the telepresence device may be illustrated as an overlay as well. For example, instructions on how to use the joysticks 4225 and 4226 in FIG. 42 may be provided in a help screen overlay. Similarly, the gestures 4631, 4632, 4633, and 4634 in FIG. 46 may be provided in an instructional or help screen overlay. In some embodiments, the instructional overlay may be in the form of moving or video instructions overlaid on an existing display. For example, the overlay may demonstrate the gestures 4631, 4632, 4633, and 4634 in FIG. 46.

According to various embodiments, an RPI may be configured with all or some of the features and embodiments described herein. For example, an RPI may include any number of the features and embodiments described herein as selectively displayed and/or selectively functional options. An explicit enumeration of all possible permutations of the various embodiments is not included herein; however, it will be apparent to one of skill in the art that any of the variously described embodiments may be selectively utilized, if not at the same time, in a single RPI.

This disclosure has been made with reference to various exemplary embodiments, including the best mode. However, those skilled in the art will recognize that changes and modifications may be made to the exemplary embodiments without departing from the scope of the present disclosure. While the principles of this disclosure have been shown in various embodiments, many modifications may be made to adapt the RPI for a specific environment and/or to satisfy particular operating requirements without departing from the principles and scope of this disclosure. These and other changes or modifications are intended to be included within the scope of the present disclosure. This disclosure includes all possible permutations of the independent claims and their dependent claims.

What is claimed is:

1. A non-transitory computer-readable storage medium storing instructions that, when executed by a processor, are configured to cause the processor to perform operations comprising:
   retrieving a list of patients;
   selectively displaying the list of patients;
   receiving a selection of a patient from the patient list;
   automatically selecting a remote presence device from a plurality of remote presence devices, wherein automatically selecting comprises:
      connecting to an admissions, discharges, and transfers (ADT) data source for a facility;
      determining using the ADT data source a current location of the selected patient within the facility; and
      selecting a remote presence device nearest the current location of the selected patient within the facility;
   communicatively connecting an electronic device to the selected remote presence device;
   displaying a live video feed from a camera of the remote presence device in a video panel on an electronic display of the electronic device; and
   updating the live video feed as the selected remote presence device moves to the selected destination.

2. The non-transitory computer-readable storage medium of claim 1, the operations further comprising:
   receiving a selection of a patient from the patient list;
   displaying an endpoint list including a plurality of remote presence devices and their respective connectivity states, wherein the endpoint list is text searchable and includes one or more persons who are currently or scheduled for a period of time to be associated with the selected patient;
   communicatively connecting an electronic device to a selected remote presence device;
   displaying a live video feed from a camera of the remote presence device in a video panel on an electronic display of the electronic device; and
   updating the live video feed as the selected remote presence device moves to the selected destination.

3. The non-transitory computer-readable storage medium of claim 2, wherein the operation of communicatively connecting an electronic device to a remote presence device is responsive to receiving a selection of a remote presence device from the endpoint list.

4. The non-transitory computer-readable storage medium of claim 2, wherein the connectivity states include at least two of ready state, a busy state, and an offline state.

5. The non-transitory computer-readable storage medium of claim 2, wherein the endpoint list is filterable based on a filtering parameter.

6. The non-transitory computer-readable storage medium of claim 5, wherein the filtering parameter includes at least one of endpoint type, manufacturer, status, facility, building, floor, room, customer, and group.

7. The non-transitory computer-readable storage medium of claim 2, wherein the endpoint list includes a name of a person.

8. The non-transitory computer-readable storage medium of claim 2, wherein the destination list includes at least one of a room name or a room number.

9. The non-transitory computer-readable storage medium of claim 2, wherein the endpoint list includes a name of a person that is scheduled for a period of time to be associated with the selected patient.

10. The non-transitory computer-readable storage medium of claim 1, the operations further comprising:
   receiving a selection of a patient from the patient list;
   automatically selecting a remote presence device from a plurality of remote presence devices in proximity to the selected patient while minimizing travel to the selected patient through an area of poor wireless connectivity;
   communicatively connecting an electronic device to the selected remote presence device;
   displaying a live video feed from a camera of the remote presence device in a video panel on an electronic display of the electronic device; and
   updating the live video feed as the remote presence device moves to the selected destination.

11. The non-transitory computer-readable storage medium of claim 1, wherein a remote presence device within a same room as the selected patient is automatically selected.

12. The non-transitory computer-readable storage medium of claim 1, wherein a remote presence device on a same floor as the selected patient is automatically selected.

13. The non-transitory computer-readable storage medium of claim 1, wherein the automatically selected remote presence device is a remote presence device that has been previously assigned to the selected patient.

* * * * *